US009150620B2

(12) United States Patent
Wu et al.

(10) Patent No.: US 9,150,620 B2
(45) Date of Patent: *Oct. 6, 2015

(54) VACCINE AGAINST MULTITYPES OF AVIAN INFLUENZA VIRUSES AND USES THEREOF

(71) Applicant: National Tsing Hua University, Hsinchu (TW)

(72) Inventors: Suh-Chin Wu, Hsinchu (TW); Shih-Chang Lin, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/219,000

(22) Filed: Mar. 19, 2014

(65) Prior Publication Data

US 2014/0193448 A1    Jul. 10, 2014

Related U.S. Application Data

(63) Continuation-in-part of application No. 13/449,654, filed on Apr. 18, 2012, now Pat. No. 8,889,147.

(51) Int. Cl.
| | | |
|---|---|---|
| *C07K 14/005* | (2006.01) | |
| *A61K 39/145* | (2006.01) | |
| *A61K 39/12* | (2006.01) | |
| *A61K 39/00* | (2006.01) | |

(52) U.S. Cl.
CPC ............ *C07K 14/005* (2013.01); *A61K 39/12* (2013.01); *A61K 39/145* (2013.01); *A61K 2039/5256* (2013.01); *A61K 2039/5258* (2013.01); *A61K 2039/53* (2013.01); *A61K 2039/545* (2013.01); *A61K 2039/55505* (2013.01); *A61K 2039/55516* (2013.01); *C07K 2319/33* (2013.01); *C07K 2319/60* (2013.01); *C12N 2760/16122* (2013.01); *C12N 2760/16123* (2013.01); *C12N 2760/16134* (2013.01); *C12N 2799/022* (2013.01); *C12N 2799/026* (2013.01)

(58) Field of Classification Search
None
See application file for complete search history.

(56) References Cited

U.S. PATENT DOCUMENTS

2009/0208531 A1 *    8/2009    Nabel et al. ............... 424/209.1

OTHER PUBLICATIONS

Wei CJ, Boyington JC, McTamney PM, Kong WP, Pearce MB et al. (2010) Induction of broadly neutralizing H1N1 influenza antibodies by vaccination. Science 329: 1060-1064.
Lin SC, Huang MH, Tsou PC, Huang LM, Chong P et al. (2011) Recombinant trimeric HA protein immunogenicity of H5N1 avian influenza viruses and their combined use with inactivated or adenovirus vaccines. PLoS One 6: e20052.
Laursen NS, Wilson IA (2013) Broadly neutralizing antibodies against influenza viruses. Antiviral Res 98: 476-483.
Kanekiyo M, Wei CJ, Yassine HM, McTamney PM, Boyington JC et al. (2013) Self-assembling influenza nanoparticle vaccines elicit broadly neutralizing H1N1 antibodies. Nature. 499(7456): 102-6.
Yang ZY, Wei CJ, Kong WP, Wu L, Xu L et al. (2007) Immunization by avian H5 influenza hemagglutinin mutants with altered receptor binding specificity. Science 317: 825-828.
Okuno Y, Isegawa Y, Sasao F, Ueda S (1993) A common neutralizing epitope conserved between the hemagglutinins of influenza A virus H1 and H2 strains. J Virol 67: 2552-2558.
Throsby M, van den Brink E, Jongeneelen M, Poon LL, Alard P et al. (2008) Heterosubtypic neutralizing monoclonal antibodies cross-protective against H5N1 and H1N1 recovered from human IgM+ memory B cells. PLoS One 3: e3942.
Corti D, Voss J, Gamblin SJ, Codoni G, Macagno A et al. (2011) A neutralizing antibody selected from plasma cells that binds to group 1 and group 2 influenza A hemagglutinins. Science 333: 850-856.

* cited by examiner

*Primary Examiner* — Agnieszka Boesen
(74) *Attorney, Agent, or Firm* — Hannah M. Tien

(57) ABSTRACT

The present invention relates to a recombinant DNA molecule encoding a mutated hemagglutinin protein, wherein the mutated hemagglutinin protein consists of the amino acid sequence of SEQ ID NO: 2 with one or more mutations at amino acid residue selecting from the group consisting of residue 83, 127, 138 and the combination thereof. The present invention also relates to a composition comprising the recombinant DNA molecule as described above and a pharmaceutically or veterinarily acceptable carrier, excipient, adjuvant, or vehicle. The present invention further relates to a kit for prime-boost vaccination, comprising at least a composition comprising a recombinant DNA molecule as described above and at least a composition for the boost-vaccination comprising a recombinant hemagglutiinin protein or a virus-like particle, wherein the recombinant hemagglutiinin protein is the corresponding hemagglutiinin protein encoded by the recombinant DNA molecule. The present invention still further relates to a method of vaccinating a subject susceptible to avian influenza comprising administrating to the subject an effective amount of the composition as described above. The present invention still further relates to a recombinant hemagglutinin protein consisting of the amino acid sequence of SEQ ID NO: 2 with one or more mutations at amino acid residue selecting from the group consisting of residue 83, 127, 138, and the combination thereof.

19 Claims, 35 Drawing Sheets

KAN-1 (clade 1)

B

Indonesia (clade 2.1)

Qinghai (clade 2.2)

D

Anhui (clade 2.3.4)

SEQUENCE LISTING

<160> NUMBER OF SEQ ID NOS: 41

<210> SEQ ID NO 1
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 1

| | | | | | | | | | | | | | | | | |
|---|---|---|---|---|---|---|---|---|---|---|---|---|---|---|---|---|
| atg | gag | aaa | att | gtc | ctg | ctg | ttc | gcc | att | gtc | tca | ctg | gtc | aaa | tcc | 48 |
| Met | Glu | Lys | Ile | Val | Leu | Leu | Phe | Ala | Ile | Val | Ser | Leu | Val | Lys | Ser | |
| 1 | | | | 5 | | | | | 10 | | | | | 15 | | |

| gat | cag | atc | tgt | att | ggc | tac | cac | gcc | aac | aat | agc | act | gaa | cag | gtc | 96 |
|---|---|---|---|---|---|---|---|---|---|---|---|---|---|---|---|---|
| Asp | Gln | Ile | Cys | Ile | Gly | Tyr | His | Ala | Asn | Asn | Ser | Thr | Glu | Gln | Val | |
| | | | 20 | | | | | 25 | | | | | 30 | | | |

| gac | act | att | atg | gaa | aaa | aac | gtg | acc | gtc | aca | cat | gct | cag | gat | att | 144 |
|---|---|---|---|---|---|---|---|---|---|---|---|---|---|---|---|---|
| Asp | Thr | Ile | Met | Glu | Lys | Asn | Val | Thr | Val | Thr | His | Ala | Gln | Asp | Ile | |
| | | 35 | | | | | 40 | | | | | 45 | | | | |

| ctc | gaa | aaa | acc | cac | aac | ggg | aaa | ctc | tgt | gat | ctc | gac | gga | gtg | aaa | 192 |
|---|---|---|---|---|---|---|---|---|---|---|---|---|---|---|---|---|
| Leu | Glu | Lys | Thr | His | Asn | Gly | Lys | Leu | Cys | Asp | Leu | Asp | Gly | Val | Lys | |
| 50 | | | | | 55 | | | | | 60 | | | | | | |

| cca | ctc | att | ctg | aga | gac | tgt | agc | gtc | gct | gga | tgg | ctc | ctc | ggc | aat | 240 |
|---|---|---|---|---|---|---|---|---|---|---|---|---|---|---|---|---|
| Pro | Leu | Ile | Leu | Arg | Asp | Cys | Ser | Val | Ala | Gly | Trp | Leu | Leu | Gly | Asn | |
| 65 | | | | | 70 | | | | | 75 | | | | | 80 | |

| cca | atg | tgt | gat | gag | ttc | atc | aac | gtc | ccc | gaa | tgg | tca | tac | atc | gtg | 288 |
|---|---|---|---|---|---|---|---|---|---|---|---|---|---|---|---|---|
| Pro | Met | Cys | Asp | Glu | Phe | Ile | Asn | Val | Pro | Glu | Trp | Ser | Tyr | Ile | Val | |
| | | | | 85 | | | | | 90 | | | | | 95 | | |

| gag | aag | gcc | aac | cct | gtg | aac | gat | ctc | tgt | tac | cct | ggc | gac | ttc | aac | 336 |
|---|---|---|---|---|---|---|---|---|---|---|---|---|---|---|---|---|
| Glu | Lys | Ala | Asn | Pro | Val | Asn | Asp | Leu | Cys | Tyr | Pro | Gly | Asp | Phe | Asn | |
| | | | 100 | | | | | 105 | | | | | 110 | | | |

| gat | tac | gag | gaa | ctg | aaa | cat | ctg | ctg | agt | agg | atc | aat | cac | ttt | gaa | 384 |
|---|---|---|---|---|---|---|---|---|---|---|---|---|---|---|---|---|
| Asp | Tyr | Glu | Glu | Leu | Lys | His | Leu | Leu | Ser | Arg | Ile | Asn | His | Phe | Glu | |
| | | 115 | | | | | 120 | | | | | 125 | | | | |

| aaa | att | cag | att | atc | ccc | aaa | tct | tcc | tgg | tcc | tcc | cat | gag | gca | tct | 432 |
|---|---|---|---|---|---|---|---|---|---|---|---|---|---|---|---|---|
| Lys | Ile | Gln | Ile | Ile | Pro | Lys | Ser | Ser | Trp | Ser | Ser | His | Glu | Ala | Ser | |
| 130 | | | | | 135 | | | | | 140 | | | | | | |

| ctg | ggc | gtg | tca | tct | gcc | tgt | cca | tac | cag | agg | aaa | tcc | tca | ttc | ttc | 480 |
|---|---|---|---|---|---|---|---|---|---|---|---|---|---|---|---|---|
| Leu | Gly | Val | Ser | Ser | Ala | Cys | Pro | Tyr | Gln | Arg | Lys | Ser | Ser | Phe | Phe | |
| 145 | | | | | 150 | | | | | 155 | | | | | 160 | |

| cgg | aac | gtg | gtg | tgg | ctc | atc | aaa | aaa | aac | tcc | acc | tac | ccc | acc | atc | 528 |
|---|---|---|---|---|---|---|---|---|---|---|---|---|---|---|---|---|
| Arg | Asn | Val | Val | Trp | Leu | Ile | Lys | Lys | Asn | Ser | Thr | Tyr | Pro | Thr | Ile | |
| | | | | 165 | | | | | 170 | | | | | 175 | | |

| aaa | cgc | tct | tac | aac | aac | aca | aat | cag | gag | gat | ctg | ctg | gtc | ctc | tgg | 576 |
|---|---|---|---|---|---|---|---|---|---|---|---|---|---|---|---|---|
| Lys | Arg | Ser | Tyr | Asn | Asn | Thr | Asn | Gln | Glu | Asp | Leu | Leu | Val | Leu | Trp | |
| | | | 180 | | | | | 185 | | | | | 190 | | | |

| gga | att | cat | cac | ccc | aat | gat | gcc | gcc | gag | cag | aca | aaa | ctg | tac | cag | 624 |
|---|---|---|---|---|---|---|---|---|---|---|---|---|---|---|---|---|
| Gly | Ile | His | His | Pro | Asn | Asp | Ala | Ala | Glu | Gln | Thr | Lys | Leu | Tyr | Gln | |
| | | 195 | | | | | 200 | | | | | 205 | | | | |

| aac | cct | acc | aca | tac | att | tct | gtg | ggc | acc | tct | aca | ctg | aat | cag | agg | 672 |
|---|---|---|---|---|---|---|---|---|---|---|---|---|---|---|---|---|
| Asn | Pro | Thr | Thr | Tyr | Ile | Ser | Val | Gly | Thr | Ser | Thr | Leu | Asn | Gln | Arg | |
| 210 | | | | | 215 | | | | | 220 | | | | | | |

| ctg | gtg | cct | aga | att | gcc | act | agg | agt | aaa | gtc | aac | ggc | cag | tcc | ggc | 720 |
|---|---|---|---|---|---|---|---|---|---|---|---|---|---|---|---|---|
| Leu | Val | Pro | Arg | Ile | Ala | Thr | Arg | Ser | Lys | Val | Asn | Gly | Gln | Ser | Gly | |
| 225 | | | | | 230 | | | | | 235 | | | | | 240 | |

| cgg | atg | gaa | ttc | ttt | tgg | acc | atc | ctc | aaa | ccc | aac | gat | gct | atc | aac | 768 |
|---|---|---|---|---|---|---|---|---|---|---|---|---|---|---|---|---|
| Arg | Met | Glu | Phe | Phe | Trp | Thr | Ile | Leu | Lys | Pro | Asn | Asp | Ala | Ile | Asn | |
| | | | | 245 | | | | | 250 | | | | | 255 | | |

| ttc | gag | tca | aac | ggc | aac | ttt | atc | gcc | cct | gaa | tac | gcc | tac | aaa | atc | 816 |
|---|---|---|---|---|---|---|---|---|---|---|---|---|---|---|---|---|
| Phe | Glu | Ser | Asn | Gly | Asn | Phe | Ile | Ala | Pro | Glu | Tyr | Ala | Tyr | Lys | Ile | |

```
                    260              265                 270
gtg aaa aag ggc gac tcc act atc atg aaa tcc gag ctg gag tac gga    864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca   1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att   1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac   1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag   1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa   1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag   1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat   1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga   1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc   1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc   1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac   1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga   1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att   1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg   1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc   1680
Val Ala Gly Leu Ser Leu Trp Met Cys Ser Asn Gly Ser Leu Gln Cys
545                 550                 555                 560 cgg atc tgt atc tag                                                1695
Arg Ile Cys Ile

<210> SEQ ID NO 2
```

-continued

```
<211> LENGTH: 548
<212> TYPE: PRT
<213> ORGANISM: Avian influenza virus
<220> FEATURE:
<221> NAME/KEY: mat_peptide
<222> LOCATION: (1)..(548)

<400> SEQUENCE: 2
```

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Arg Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys

```
                    370                 375                 380
Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
            435                 440                 445

Arg Leu Gln Leu Arg Asp Asn Ala Lys Glu Leu Gly Asn Gly Cys Phe
        450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Ile Tyr Gln Ile
                500                 505                 510

Leu Ser Ile Tyr Ser Thr Val Ala Ser Ser Leu Ala Leu Ala Ile Met
        515                 520                 525

Val Ala Gly Leu Ser Leu Trp Met Cys Ser Asn Gly Ser Leu Gln Cys
    530                 535                 540

Arg Ile Cys Ile
545

<210> SEQ ID NO 3
<211> LENGTH: 1695
<212> TYPE: DNA
<213> ORGANISM: Avian Avian influenza virus
<220> FEATURE:
<221> NAME/KEY: CDS
<222> LOCATION: (1)..(1695)

<400> SEQUENCE: 3 atg gag aaa att gtc ctg ctg ttc gcc att gtc tca ctg gtc aaa tcc      48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc      96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att     144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa     192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat     240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg     288
Pro Met Cys Asp Glu Phe Ile Asn Val Pro Glu Trp Ser Tyr Ile Val
                85                  90                  95 gag aag aac aac acc gtg aac gat ctc tgt tac cct ggc gac ttc aac     336
Glu Lys Asn Asn Thr Val Asn Asp Leu Cys Tyr Pro Gly Asp Phe Asn
            100                 105                 110 gat tac gag gaa ctg aaa cat ctg ctg agt agg atc aat cac ttt gaa     384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct     432
```

```
Lys Ile Gln Ile Ile Pro Lys Ser Ser Trp Ser Ser His Glu Ala Ser
130                 135                 140 ctg ggc gtg tca tct gcc tgt cca tac cag agg aaa tcc tca ttc ttc    480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc    528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg    576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag    624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg    672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc    720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac    768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc    816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga    864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca   1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att   1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac   1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag   1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa   1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag   1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat   1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga   1344
Val Trp Thr Tyr Asn Ala Glu Leu Leu Val Leu Met Glu Asn Glu Arg
        435                 440                 445
```

```
acc ctg gac ttc cac gac tca aac gtg aaa aac ctg tac gac aaa gtc    1392
Thr Leu Asp Phe His Asp Ser Asn Val Lys Asn Leu Tyr Asp Lys Val
450                 455                 460 cgg ctc cag ctg agg gat aat gcc aag gaa ctc gga aat ggc tgc ttc    1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac    1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
500                 505                 510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
            515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560 cgg atc tgt atc tag                                                1695
Arg Ile Cys Ile <210> SEQ ID NO 4
<211> LENGTH: 548
<212> TYPE: PRT
<213> ORGANISM: Avian influenza virus
<220> FEATURE:
<221> NAME/KEY: mat_peptide
<222> LOCATION: (1)..(548)

<400> SEQUENCE: 4

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Thr His Asn Gly Lys Leu Cys Asp Leu Asp Gly Val Lys
            35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Asn Asn Thr Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Arg Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
```

195                 200                 205
Leu Val Pro Arg Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Ile Tyr Gln Ile
            500                 505                 510

Leu Ser Ile Tyr Ser Thr Val Ala Ser Ser Leu Ala Leu Ala Ile Met
        515                 520                 525

Val Ala Gly Leu Ser Leu Trp Met Cys Ser Asn Gly Ser Leu Gln Cys
    530                 535                 540

Arg Ile Cys Ile
545

<210> SEQ ID NO 5
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 5

```
atg gag aaa att gtc ctg ctg ttc gcc att gtc tca ctg gtc aaa tcc        48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc        96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att       144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa       192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat       240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg       288
Pro Met Cys Asp Glu Phe Ile Asn Val Pro Glu Trp Ser Tyr Ile Val
                85                  90                  95 gag aag gcc aac cct aac aac acc ctc tgt tac cct ggc gac ttc aac       336
Glu Lys Ala Asn Pro Asn Asn Thr Leu Cys Tyr Pro Gly Asp Phe Asn
            100                 105                 110 gat tac gag gaa ctg aaa cat ctg ctg agt agg atc aat cac ttt gaa       384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct       432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc       480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc       528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg       576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag       624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg       672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc       720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac       768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc       816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga       864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct       912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa       960
Met Pro Phe His Asn Ile His Pro Leu Thr Ile Gly Glu Cys Pro Lys
305                 310                 315                 320
```

```
tac gtc aaa tca aac cgg ctc gtg ctg gct act ggg ctg aga aac tca      1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att      1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac      1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag      1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa      1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag      1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat      1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga      1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc      1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc      1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac      1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga      1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att      1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg      1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc      1680
Val Ala Gly Leu Ser Leu Trp Met Cys Ser Asn Gly Ser Leu Gln Cys
545                 550                 555                 560 cgg atc tgt atc tag                                                  1695
Arg Ile Cys Ile <210> SEQ ID NO 6
<211> LENGTH: 564
<212> TYPE: PRT
<213> ORGANISM: Avian influenza virus

<400> SEQUENCE: 6

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
```

```
                35                  40                  45
Leu Glu Lys Thr His Asn Gly Lys Leu Cys Asp Leu Asp Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Asn Asn Thr Leu Cys Tyr Pro Gly Asp Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Ser His Glu Ala Ser
            130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
            355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
            435                 440                 445

Thr Leu Asp Phe His Asp Ser Asn Val Lys Asn Leu Tyr Asp Lys Val
450                 455                 460
```

```
Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
            485                 490                 495

Gly Thr Tyr Asp Tyr Pro Gln Tyr Ser Glu Glu Ala Arg Leu Lys Arg
        500                 505                 510

Glu Glu Ile Ser Gly Val Lys Leu Glu Ser Ile Gly Ile Tyr Gln Ile
            515                 520                 525

Leu Ser Ile Tyr Ser Thr Val Ala Ser Ser Leu Ala Leu Ala Ile Met
530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 7
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 7 atg gag aaa att gtc ctg ctg ttc gcc att gtc tca ctg gtc aaa tcc     48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc     96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att    144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa    192
Leu Glu Lys Thr His Asn Gly Lys Leu Cys Asp Leu Asp Gly Val Lys
50                  55                  60 cca ctc att ctg aga gac tgt agc gtc gct gga tgg ctc ctc ggc aat    240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg    288
Pro Met Cys Asp Glu Phe Ile Asn Val Pro Glu Trp Ser Tyr Ile Val
                85                  90                  95 gag aag gcc aac cct gtg aac gat ctc tgt tac cct ggc aac ttc acc    336
Glu Lys Ala Asn Pro Val Asn Asp Leu Cys Tyr Pro Gly Asn Phe Thr
            100                 105                 110 gat tac gag gaa ctg aaa cat ctg ctg agt agg atc aat cac ttt gaa    384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct    432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc    480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc    528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg    576
Lys Arg Ser Tyr Asn Asn Thr Asn Gln Glu Asp Leu Leu Val Leu Trp
            180                 185                 190
```

```
gga att cat cac ccc aat gat gcc gcc gag cag aca aaa ctg tac cag      624
Gly Ile His His Pro Asn Asp Ala Ala Glu Gln Thr Lys Leu Tyr Gln
            195                 200                 205 aac cct acc aca tac att tct gtg ggc acc tct aca ctg aat cag agg      672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc      720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac      768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc      816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga      864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct      912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa      960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca     1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att     1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac     1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag     1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa     1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag     1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat     1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga     1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc     1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc     1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac     1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga     1536
Gly Thr Tyr Asp Tyr Pro Gln Tyr Ser Glu Glu Ala Arg Leu Lys Arg
```

```
                        500                 505                 510
gag gag atc tct ggc gtc aaa ctg gag tct atc gga atc tac cag att       1584
Glu Glu Ile Ser Gly Val Lys Leu Glu Ser Ile Gly Ile Tyr Gln Ile
            515                 520                 525 ctg tcc atc tac tct act gtg gct tct tca ctg gct ctg gcc atc atg       1632
Leu Ser Ile Tyr Ser Thr Val Ala Ser Ser Leu Ala Leu Ala Ile Met
530                 535                 540 gtc gct ggg ctg tct ctg tgg atg tgc tca aat gga tca ctc cag tgc       1680
Val Ala Gly Leu Ser Leu Trp Met Cys Ser Asn Gly Ser Leu Gln Cys
545                 550                 555                 560 cgg atc tgt atc tag                                                   1695
Arg Ile Cys Ile <210> SEQ ID NO 8
<211> LENGTH: 564
<212> TYPE: PRT
<213> ORGANISM: Avian influenza virus

<400> SEQUENCE: 8

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asn Phe Thr
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser His Glu Ala Ser
    130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285
```

```
Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 9
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 9 atg gag aaa att gtc ctg ctg ttc gcc att gtc tca ctg gtc aaa tcc    48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc    96
Asp Gln Ile Cys Ile Gly Tyr His Ala Asn Asn Ser Thr Glu Gln Val
                20                  25                  30 gac act att atg gaa aaa aac gtg acc gtc aca cat gct cag gat att   144
Asp Thr Ile Met Glu Lys Asn Val Thr Val Thr His Ala Gln Asp Ile
            35                  40                  45 ctc gaa aaa acc cac aac ggg aaa ctc tgt gat ctc gac gga gtg aaa   192
Leu Glu Lys Thr His Asn Gly Lys Leu Cys Asp Leu Asp Gly Val Lys
        50                  55                  60
```

```
cca ctc att ctg aga gac tgt agc gtc gct gga tgg ctc ctc ggc aat      240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg      288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac      336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa      384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag aac tct      432
Lys Ile Gln Ile Ile Pro Lys Ser Ser Trp Ser Ser His Glu Asn Ser
130                 135                 140 tct ggc gtg tca tct gcc tgt cca tac cag agg aaa tcc tca ttc ttc      480
Ser Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc      528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg      576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag      624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg      672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc      720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac      768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc      816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga      864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct      912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa      960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca     1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att     1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac     1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag     1152
Ser Asn Glu Gln Gly Ser Gly Tyr Ala Ala Asp Lys Glu Ser Thr Gln
```

```
                370             375             380
aaa gca atc gat ggc gtc acc aac aaa gtc aat tca atc atc gac aaa    1200
Lys Ala Ile Asp Gly Val Thr Asn Lys Val Asn Ser Ile Ile Asp Lys
385             390             395             400 atg aac acc cag ttc gag gct gtg gga cga gag ttc aat aac ctg gag    1248
Met Asn Thr Gln Phe Glu Ala Val Gly Arg Glu Phe Asn Asn Leu Glu
            405             410             415 cgg aga atc gaa aac ctg aac aaa aaa atg gag gac ggc ttc ctc gat    1296
Arg Arg Ile Glu Asn Leu Asn Lys Lys Met Glu Asp Gly Phe Leu Asp
        420             425             430 gtg tgg acc tac aat gct gaa ctg ctg gtg ctc atg gaa aac gag aga    1344
Val Trp Thr Tyr Asn Ala Glu Leu Leu Val Leu Met Glu Asn Glu Arg
    435             440             445 acc ctg gac ttc cac gac tca aac gtg aaa aac ctg tac gac aaa gtc    1392
Thr Leu Asp Phe His Asp Ser Asn Val Lys Asn Leu Tyr Asp Lys Val
450             455             460 cgg ctc cag ctg agg gat aat gcc aag gaa ctc gga aat ggc tgc ttc    1440
Arg Leu Gln Leu Arg Asp Asn Ala Lys Glu Leu Gly Asn Gly Cys Phe
465             470             475             480 gag ttc tac cac aaa tgt gac aac gag tgt atg gag tct gtc cga aac    1488
Glu Phe Tyr His Lys Cys Asp Asn Glu Cys Met Glu Ser Val Arg Asn
            485             490             495 gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
        500             505             510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
    515             520             525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
530             535             540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545             550             555             560 cgg atc tgt atc tag                                                1695
Arg Ile Cys Ile <210> SEQ ID NO 10
<211> LENGTH: 548
<212> TYPE: PRT
<213> ORGANISM: Avian influenza virus
<220> FEATURE:
<221> NAME/KEY: mat_peptide
<222> LOCATION: (1)..(548)

<400> SEQUENCE: 10

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
            85                  90                  95

Asp Tyr Glu Glu Leu Lys His Leu Leu Ser Arg Ile Asn His Phe Glu
```

```
              100                 105                 110
Lys Ile Gln Ile Ile Pro Lys Ser Ser Trp Ser Ser His Glu Asn Ser
            115                 120                 125

Ser Gly Val Ser Ser Ala Cys Pro Tyr Gln Arg Lys Ser Ser Phe Phe
        130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Ile Tyr Gln Ile
            500                 505                 510

Leu Ser Ile Tyr Ser Thr Val Ala Ser Ser Leu Ala Leu Ala Ile Met
        515                 520                 525
```

-continued

```
Val Ala Gly Leu Ser Leu Trp Met Cys Ser Asn Gly Ser Leu Gln Cys
    530                 535                 540

Arg Ile Cys Ile
545

<210> SEQ ID NO 11
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 11 atg gag aaa att gtc ctg ctg ttc gcc att gtc tca ctg gtc aaa tcc      48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc      96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att     144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa     192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat     240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg     288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac     336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa     384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct     432
Lys Ile Gln Ile Ile Pro Lys Ser Ser Trp Ser Ser His Glu Ala Ser
    130                 135                 140 ctg ggc gtg tca tct gcc tgt cca tac aac agg acc tcc tca ttc ttc     480
Leu Gly Val Ser Ser Ala Cys Pro Tyr Asn Arg Thr Ser Ser Phe Phe
145                 150                 155                 160 cgg aac gtg gtg tgg ctc atc aaa aaa aac tcc acc tac ccc acc atc     528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg     576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag     624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg     672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc     720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac     768
```

|  |  |  |  |  |  |  |  |  |  |  |  |  |  |  |  |
|---|---|---|---|---|---|---|---|---|---|---|---|---|---|---|---|
| Arg | Met | Glu | Phe | Phe | Trp | Thr | Ile | Leu | Lys | Pro | Asn | Asp | Ala | Ile | Asn |
|  |  |  | 245 |  |  |  |  | 250 |  |  |  |  | 255 |  |  |

```
ttc gag tca aac ggc aac ttt atc gcc cct gaa tac gcc tac aaa atc    816
Phe Glu Ser Asn Gly Asn Phe Ile Ala Pro Glu Tyr Ala Tyr Lys Ile
        260                 265                 270 gtg aaa aag ggc gac tcc act atc atg aaa tcc gag ctg gag tac gga    864
Val Lys Lys Gly Asp Ser Thr Ile Met Lys Ser Glu Leu Glu Tyr Gly
            275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
        290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca    1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att    1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac    1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag    1152
Ser Asn Glu Gln Gly Ser Gly Tyr Ala Ala Asp Lys Glu Ser Thr Gln
370                 375                 380 aaa gca atc gat ggc gtc acc aac aaa gtc aat tca atc atc gac aaa    1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag    1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat    1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga    1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc    1392
Thr Leu Asp Phe His Asp Ser Asn Val Lys Asn Leu Tyr Asp Lys Val
450                 455                 460 cgg ctc cag ctg agg gat aat gcc aag gaa ctc gga aat ggc tgc ttc    1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac    1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
        530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560
```

```
cgg atc tgt atc tag                                                      1695
Arg Ile Cys Ile
```

<210> SEQ ID NO 12
<211> LENGTH: 564
<212> TYPE: PRT
<213> ORGANISM: Avian influenza virus

<400> SEQUENCE: 12

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Asn Arg Thr Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365
```

```
Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 13
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 13 atg gag aaa att gtc ctg ctg ttc gcc att gtc tca ctg gtc aaa tcc        48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc        96
Asp Gln Ile Cys Ile Gly Tyr His Ala Asn Asn Ser Thr Glu Gln Val
                20                  25                  30 gac act att atg gaa aaa aac gtg acc gtc aca cat gct cag gat att       144
Asp Thr Ile Met Glu Lys Asn Val Thr Val Thr His Ala Gln Asp Ile
            35                  40                  45 ctc gaa aaa acc cac aac ggg aaa ctc tgt gat ctc gac gga gtg aaa       192
Leu Glu Lys Thr His Asn Gly Lys Leu Cys Asp Leu Asp Gly Val Lys
        50                  55                  60 cca ctc att ctg aga gac tgt agc gtc gct gga tgg ctc ctc ggc aat       240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg       288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac       336
Glu Lys Ala Asn Pro Val Asn Asp Leu Cys Tyr Pro Gly Asp Phe Asn
                100                 105                 110 gat tac gag gaa ctg aaa cat ctg ctg agt agg atc aat cac ttt gaa       384
```

```
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct       432
Lys Ile Gln Ile Ile Pro Lys Ser Ser Trp Ser Ser His Glu Ala Ser
130                 135                 140 ctg ggc gtg tca tct gcc tgt cca tac cag agg aac tcc tca ttc ttc       480
Leu Gly Val Ser Ser Ala Cys Pro Tyr Gln Arg Asn Ser Ser Phe Phe
145                 150                 155                 160 cgg aac gtg gtg tgg ctc atc aaa aaa aac tcc acc tac ccc acc atc       528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg       576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag       624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg       672
Asn Pro Thr Thr Tyr Ile Ser Val Gly Thr Ser Thr Leu Asn Gln Arg
210                 215                 220 ctg gtg cct aga att gcc act agg agt aaa gtc aac ggc cag tcc ggc       720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac       768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc       816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga       864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct       912
Asn Cys Asn Thr Lys Cys Gln Thr Pro Met Gly Ala Ile Asn Ser Ser
290                 295                 300 atg ccc ttc cac aac atc cac cct ctc act atc ggc gaa tgc cca aaa       960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca      1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att      1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac      1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag      1152
Ser Asn Glu Gln Gly Ser Gly Tyr Ala Ala Asp Lys Glu Ser Thr Gln
370                 375                 380 aaa gca atc gat ggc gtc acc aac aaa gtc aat tca atc atc gac aaa      1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag      1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat      1296
Arg Arg Ile Glu Asn Leu Asn Lys Lys Met Glu Asp Gly Phe Leu Asp
            420                 425                 430
```

```
gtg tgg acc tac aat gct gaa ctg ctg gtg ctc atg gaa aac gag aga    1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc    1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc    1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac    1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560 cgg atc tgt atc tag                                                1695
Arg Ile Cys Ile <210> SEQ ID NO 14
<211> LENGTH: 564
<212> TYPE: PRT
<213> ORGANISM: Avian influenza virus

<400> SEQUENCE: 14

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Arg Asn Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190
```

Gly Ile His His Pro Asn Asp Ala Glu Gln Thr Lys Leu Tyr Gln
         195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
             245                 250                 255

Phe Glu Ser Asn Gly Asn Phe Ile Ala Pro Glu Tyr Ala Tyr Lys Ile
             260                 265                 270

Val Lys Lys Gly Asp Ser Thr Ile Met Lys Ser Glu Leu Glu Tyr Gly
         275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
             325                 330                 335

Pro Gln Arg Glu Thr Arg Gly Leu Phe Gly Ala Ile Ala Gly Phe Ile
             340                 345                 350

Glu Gly Gly Trp Gln Gly Met Val Asp Gly Trp Tyr Gly Tyr His His
         355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
             405                 410                 415

Arg Arg Ile Glu Asn Leu Asn Lys Lys Met Glu Asp Gly Phe Leu Asp
             420                 425                 430

Val Trp Thr Tyr Asn Ala Glu Leu Leu Val Leu Met Glu Asn Glu Arg
         435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
             485                 490                 495

Gly Thr Tyr Asp Tyr Pro Gln Tyr Ser Glu Glu Ala Arg Leu Lys Arg
             500                 505                 510

Glu Glu Ile Ser Gly Val Lys Leu Glu Ser Ile Gly Ile Tyr Gln Ile
         515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 15
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 15

```
atg gag aaa att gtc ctg ctg ttc gcc att gtc tca ctg gtc aaa tcc      48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc      96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att     144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa     192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat     240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg     288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac     336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa     384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct     432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc     480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc     528
Arg Asn Val Val Trp Leu Ile Lys Lys Asn Ser Thr Tyr Pro Thr Ile
                165                 170                 175 aac cgc tct tac aac aac aca aat cag gag gat ctg ctg gtc ctc tgg     576
Asn Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag     624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg     672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc     720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac     768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc     816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga     864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct     912
Asn Cys Asn Thr Lys Cys Gln Thr Pro Met Gly Ala Ile Asn Ser Ser
    290                 295                 300
```

```
atg ccc ttc cac aac atc cac cct ctc act atc ggc gaa tgc cca aaa      960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca     1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att     1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac     1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag     1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa     1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag     1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat     1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga     1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc     1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc     1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac     1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga     1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att     1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg     1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc     1680
Val Ala Gly Leu Ser Leu Trp Met Cys Ser Asn Gly Ser Leu Gln Cys
545                 550                 555                 560 cgg atc tgt atc tag                                                  1695
Arg Ile Cys Ile <210> SEQ ID NO 16
<211> LENGTH: 564
<212> TYPE: PRT
<213> ORGANISM: Avian influenza virus

<400> SEQUENCE: 16

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
```

```
                20                  25                  30
Asp Thr Ile Met Glu Lys Asn Val Thr Val Thr His Ala Gln Asp Ile
             35                  40                  45

Leu Glu Lys Thr His Asn Gly Lys Leu Cys Asp Leu Asp Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser His Glu Ala Ser
    130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Asn Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445
```

```
Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
                500                 505                 510

Glu Glu Ile Ser Gly Val Lys Leu Glu Ser Ile Gly Ile Tyr Gln Ile
            515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 17
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 17 atg gag aaa att gtc ctg ctg ttc gcc att gtc tca ctg gtc aaa tcc      48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc      96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att     144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa     192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat     240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg     288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac     336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa     384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct     432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc     480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc     528
Arg Asn Val Val Trp Leu Ile Lys Lys Asn Ser Thr Tyr Pro Thr Ile
                165                 170                 175
```

-continued

| | |
|---|---|
| aaa cgc tct tac aac aac aca aat cag gag gat ctg ctg gtc ctc tgg<br>Lys Arg Ser Tyr Asn Asn Thr Asn Gln Glu Asp Leu Leu Val Leu Trp<br>180              185             190 | 576 |
| gga att cat cac tct aat gat aca gcc gag cag aca aaa ctg tac cag<br>Gly Ile His His Ser Asn Asp Thr Ala Glu Gln Thr Lys Leu Tyr Gln<br>195             200            205 | 624 |
| aac cct acc aca tac att tct gtg ggc acc tct aca ctg aat cag agg<br>Asn Pro Thr Thr Tyr Ile Ser Val Gly Thr Ser Thr Leu Asn Gln Arg<br>210              215            220 | 672 |
| ctg gtg cct aga att gcc act agg agt aaa gtc aac ggc cag tcc ggc<br>Leu Val Pro Arg Ile Ala Thr Arg Ser Lys Val Asn Gly Gln Ser Gly<br>225              230           235            240 | 720 |
| cgg atg gaa ttc ttt tgg acc atc ctc aaa ccc aac gat gct atc aac<br>Arg Met Glu Phe Phe Trp Thr Ile Leu Lys Pro Asn Asp Ala Ile Asn<br>245              250           255 | 768 |
| ttc gag tca aac ggc aac ttt atc gcc cct gaa tac gcc tac aaa atc<br>Phe Glu Ser Asn Gly Asn Phe Ile Ala Pro Glu Tyr Ala Tyr Lys Ile<br>260             265            270 | 816 |
| gtg aaa aag ggc gac tcc act atc atg aaa tcc gag ctg gag tac gga<br>Val Lys Lys Gly Asp Ser Thr Ile Met Lys Ser Glu Leu Glu Tyr Gly<br>275              280           285 | 864 |
| aac tgt aac acc aaa tgc cag acc cct atg ggc gct atc aac tct tct<br>Asn Cys Asn Thr Lys Cys Gln Thr Pro Met Gly Ala Ile Asn Ser Ser<br>290              295           300 | 912 |
| atg ccc ttc cac aac atc cac cct ctc act atc ggc gaa tgc cca aaa<br>Met Pro Phe His Asn Ile His Pro Leu Thr Ile Gly Glu Cys Pro Lys<br>305              310           315           320 | 960 |
| tac gtc aaa tca aac cgg ctc gtg ctg gct act ggg ctg aga aac tca<br>Tyr Val Lys Ser Asn Arg Leu Val Leu Ala Thr Gly Leu Arg Asn Ser<br>325              330           335 | 1008 |
| cct cag cga gag act aga ggc ctg ttt ggc gcc att gct gga ttc att<br>Pro Gln Arg Glu Thr Arg Gly Leu Phe Gly Ala Ile Ala Gly Phe Ile<br>340              345           350 | 1056 |
| gag gga ggc tgg cag gga atg gtc gat ggc tgg tac gga tac cat cac<br>Glu Gly Gly Trp Gln Gly Met Val Asp Gly Trp Tyr Gly Tyr His His<br>355              360           365 | 1104 |
| tcc aat gag cag gga tct gga tac gct gcc gat aag gag tcc acc cag<br>Ser Asn Glu Gln Gly Ser Gly Tyr Ala Ala Asp Lys Glu Ser Thr Gln<br>370              375           380 | 1152 |
| aaa gca atc gat ggc gtc acc aac aaa gtc aat tca atc atc gac aaa<br>Lys Ala Ile Asp Gly Val Thr Asn Lys Val Asn Ser Ile Ile Asp Lys<br>385              390           395            400 | 1200 |
| atg aac acc cag ttc gag gct gtg gga cga gag ttc aat aac ctg gag<br>Met Asn Thr Gln Phe Glu Ala Val Gly Arg Glu Phe Asn Asn Leu Glu<br>405              410           415 | 1248 |
| cgg aga atc gaa aac ctg aac aaa aaa atg gag gac ggc ttc ctc gat<br>Arg Arg Ile Glu Asn Leu Asn Lys Lys Met Glu Asp Gly Phe Leu Asp<br>420              425           430 | 1296 |
| gtg tgg acc tac aat gct gaa ctg ctg gtg ctc atg gaa aac gag aga<br>Val Trp Thr Tyr Asn Ala Glu Leu Leu Val Leu Met Glu Asn Glu Arg<br>435              440           445 | 1344 |
| acc ctg gac ttc cac gac tca aac gtg aaa aac ctg tac gac aaa gtc<br>Thr Leu Asp Phe His Asp Ser Asn Val Lys Asn Leu Tyr Asp Lys Val<br>450              455           460 | 1392 |
| cgg ctc cag ctg agg gat aat gcc aag gaa ctc gga aat ggc tgc ttc<br>Arg Leu Gln Leu Arg Asp Asn Ala Lys Glu Leu Gly Asn Gly Cys Phe<br>465              470           475            480 | 1440 |
| gag ttc tac cac aaa tgt gac aac gag tgt atg gag tct gtc cga aac<br>Glu Phe Tyr His Lys Cys Asp Asn Glu Cys Met Glu Ser Val Arg Asn<br>485              490           495 | 1488 |

-continued

```
gga acc tac gac tac cct cag tac tct gag gag gct aga ctg aaa cga    1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att    1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg    1632
Leu Ser Ile Tyr Ser Thr Val Ala Ser Ser Leu Ala Leu Ala Ile Met
530                 535                 540 gtc gct ggg ctg tct ctg tgg atg tgc tca aat gga tca ctc cag tgc    1680
Val Ala Gly Leu Ser Leu Trp Met Cys Ser Asn Gly Ser Leu Gln Cys
545                 550                 555                 560 cgg atc tgt atc tag                                                 1695
Arg Ile Cys Ile <210> SEQ ID NO 18
<211> LENGTH: 564
<212> TYPE: PRT
<213> ORGANISM: Avian influenza virus

<400> SEQUENCE: 18

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Arg Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Ser Asn Asp Thr Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270
```

```
Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ala Arg Leu Lys Arg
            500                 505                 510

Glu Glu Ile Ser Gly Val Lys Leu Glu Ser Ile Gly Ile Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 19
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 19 atg gag aaa att gtc ctg ctg ttc gcc att gtc tca ctg gtc aaa tcc      48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc      96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att     144
Asp Thr Ile Met Glu Lys Asn Val Thr Val Thr His Ala Gln Asp Ile
        35                  40                  45
```

-continued

```
ctc gaa aaa acc cac aac ggg aaa ctc tgt gat ctc gac gga gtg aaa    192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat    240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg    288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac    336
Glu Lys Ala Asn Pro Val Asn Asp Leu Cys Tyr Pro Gly Asp Phe Asn
            100                 105                 110 gat tac gag gaa ctg aaa cat ctg ctg agt agg atc aat cac ttt gaa    384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct    432
Lys Ile Gln Ile Ile Pro Lys Ser Ser Trp Ser Ser His Glu Ala Ser
    130                 135                 140 ctg ggc gtg tca tct gcc tgt cca tac cag agg aaa tcc tca ttc ttc    480
Leu Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc    528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg    576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag    624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg    672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc    720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac    768
Arg Met Glu Phe Phe Trp Thr Ile Leu Lys Pro Asn Asp Ala Ile Asn
                245                 250                 255 ttc gag tca aac ggc aac ttt atc gcc cct gaa aac gcc acc aaa atc    816
Phe Glu Ser Asn Gly Asn Phe Ile Ala Pro Glu Asn Ala Thr Lys Ile
            260                 265                 270 gtg aaa aag ggc gac tcc act atc atg aaa tcc gag ctg gag tac gga    864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca   1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att   1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac   1104
Glu Gly Gly Trp Gln Gly Met Val Asp Gly Trp Tyr Gly Tyr His His
        355                 360                 365
```

```
tcc aat gag cag gga tct gga tac gct gcc gat aag gag tcc acc cag      1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa      1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag      1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat      1296
Arg Arg Ile Glu Asn Leu Asn Lys Lys Met Glu Asp Gly Phe Leu Asp
            420                 425                 430 gtg tgg acc tac aat gct gaa ctg ctg gtc ctc atg gaa aac gag aga      1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc      1392
Thr Leu Asp Phe His Asp Ser Asn Val Lys Asn Leu Tyr Asp Lys Val
450                 455                 460 cgg ctc cag ctg agg gat aat gcc aag gaa ctc gga aat ggc tgc ttc      1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac      1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga      1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att      1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg      1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc      1680
Val Ala Gly Leu Ser Leu Trp Met Cys Ser Asn Gly Ser Leu Gln Cys
545                 550                 555                 560 cgg atc tgt atc tag                                                   1695
Arg Ile Cys Ile <210> SEQ ID NO 20
<211> LENGTH: 564
<212> TYPE: PRT
<213> ORGANISM: Avian influenza virus

<400> SEQUENCE: 20

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
```

-continued

```
                100                 105                 110
Asp Tyr Glu Glu Leu Lys His Leu Leu Ser Arg Ile Asn His Phe Glu
            115                 120                 125
Lys Ile Gln Ile Ile Pro Lys Ser Ser Trp Ser Ser His Glu Ala Ser
        130                 135                 140
Leu Gly Val Ser Ser Ala Cys Pro Tyr Gln Arg Lys Ser Ser Phe Phe
145                 150                 155                 160
Arg Asn Val Val Trp Leu Ile Lys Lys Asn Ser Thr Tyr Pro Thr Ile
                165                 170                 175
Lys Arg Ser Tyr Asn Asn Thr Asn Gln Glu Asp Leu Leu Val Leu Trp
            180                 185                 190
Gly Ile His His Pro Asn Asp Ala Ala Glu Gln Thr Lys Leu Tyr Gln
        195                 200                 205
Asn Pro Thr Thr Tyr Ile Ser Val Gly Thr Ser Thr Leu Asn Gln Arg
210                 215                 220
Leu Val Pro Arg Ile Ala Thr Arg Ser Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Glu Asn Ala Thr Lys Ile
            260                 265                 270
Val Lys Lys Gly Asp Ser Thr Ile Met Lys Ser Glu Leu Glu Tyr Gly
        275                 280                 285
Asn Cys Asn Thr Lys Cys Gln Thr Pro Met Gly Ala Ile Asn Ser Ser
        290                 295                 300
Met Pro Phe His Asn Ile His Pro Leu Thr Ile Gly Glu Cys Pro Lys
305                 310                 315                 320
Tyr Val Lys Ser Asn Arg Leu Val Leu Ala Thr Gly Leu Arg Asn Ser
                325                 330                 335
Pro Gln Arg Glu Thr Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
        370                 375                 380
Lys Ala Ile Asp Gly Val Thr Asn Lys Val Asn Ser Ile Ile Asp Lys
385                 390                 395                 400
Met Asn Thr Gln Phe Glu Ala Val Gly Arg Glu Phe Asn Asn Leu Glu
                405                 410                 415
Arg Arg Ile Glu Asn Leu Asn Lys Lys Met Glu Asp Gly Phe Leu Asp
            420                 425                 430
Val Trp Thr Tyr Asn Ala Glu Leu Leu Val Leu Met Glu Asn Glu Arg
        435                 440                 445
Thr Leu Asp Phe His Asp Ser Asn Val Lys Asn Leu Tyr Asp Lys Val
450                 455                 460
Arg Leu Gln Leu Arg Asp Asn Ala Lys Glu Leu Gly Asn Gly Cys Phe
465                 470                 475                 480
Glu Phe Tyr His Lys Cys Asp Asn Glu Cys Met Glu Ser Val Arg Asn
                485                 490                 495
Gly Thr Tyr Asp Tyr Pro Gln Tyr Ser Glu Glu Ala Arg Leu Lys Arg
            500                 505                 510
Glu Glu Ile Ser Gly Val Lys Leu Glu Ser Ile Gly Ile Tyr Gln Ile
        515                 520                 525
```

Leu Ser Ile Tyr Ser Thr Val Ala Ser Ser Leu Ala Leu Ala Ile Met
            530                 535                 540

Val Ala Gly Leu Ser Leu Trp Met Cys Ser Asn Gly Ser Leu Gln Cys
545                 550                 555                 560

Arg Ile Cys Ile

<210> SEQ ID NO 21
<211> LENGTH: 759
<212> TYPE: DNA
<213> ORGANISM: Avian influenza virus
<220> FEATURE:
<221> NAME/KEY: CDS
<222> LOCATION: (1)..(759)

<400> SEQUENCE: 21

| | | |
|---|---|---|
| atg agt ctt cta acc gag gtc gaa acg tat gtt ctc tct atc gtc ccg<br>Met Ser Leu Leu Thr Glu Val Glu Thr Tyr Val Leu Ser Ile Val Pro<br>1               5                  10                  15 | 48 |
| tca ggc ccc ctc aaa gcc gag atc gca cag aga ctt gaa gat gtc ttt<br>Ser Gly Pro Leu Lys Ala Glu Ile Ala Gln Arg Leu Glu Asp Val Phe<br>            20                  25                  30 | 96 |
| gca ggg aag aac acc gat ctt gag gtt ctc atg gaa tgg cta aag aca<br>Ala Gly Lys Asn Thr Asp Leu Glu Val Leu Met Glu Trp Leu Lys Thr<br>        35                  40                  45 | 144 |
| aga cca atc ctg tca cct ctg act aag ggg att tta gga ttt gtg ttc<br>Arg Pro Ile Leu Ser Pro Leu Thr Lys Gly Ile Leu Gly Phe Val Phe<br>    50                  55                  60 | 192 |
| acg ctc acc gtg ccc agt gag cgg gga ctg cag cgt aga cgc ttt gtc<br>Thr Leu Thr Val Pro Ser Glu Arg Gly Leu Gln Arg Arg Arg Phe Val<br>65                  70                  75                  80 | 240 |
| caa aat gct ctt aat ggg aac gga gat cca aat aac atg gac aaa gca<br>Gln Asn Ala Leu Asn Gly Asn Gly Asp Pro Asn Asn Met Asp Lys Ala<br>                85                  90                  95 | 288 |
| gtt aaa ctg tat agg aag ctt aag agg gag ata aca ttc cat ggg gcc<br>Val Lys Leu Tyr Arg Lys Leu Lys Arg Glu Ile Thr Phe His Gly Ala<br>            100                 105                 110 | 336 |
| aaa gaa ata gca ctc agt tat tct gct ggt gca ctt gcc agt tgt atg<br>Lys Glu Ile Ala Leu Ser Tyr Ser Ala Gly Ala Leu Ala Ser Cys Met<br>        115                 120                 125 | 384 |
| ggc ctc ata tac aac agg atg ggg gct gtg acc act gaa gtg gca ttt<br>Gly Leu Ile Tyr Asn Arg Met Gly Ala Val Thr Thr Glu Val Ala Phe<br>    130                 135                 140 | 432 |
| ggc ctg gta tgc gca acc tgt gaa cag att gct gac tcc cag cat cgg<br>Gly Leu Val Cys Ala Thr Cys Glu Gln Ile Ala Asp Ser Gln His Arg<br>145                 150                 155                 160 | 480 |
| tct cat agg caa atg gtg aca aca acc aat cca cta atc aga cat gag<br>Ser His Arg Gln Met Val Thr Thr Thr Asn Pro Leu Ile Arg His Glu<br>                165                 170                 175 | 528 |
| aac aga atg gtt cta gcc agc act aca gct aag gct atg gag caa atg<br>Asn Arg Met Val Leu Ala Ser Thr Thr Ala Lys Ala Met Glu Gln Met<br>            180                 185                 190 | 576 |
| gct gga tcg agt gag caa gca gca gag gcc atg gat att gct agt cag<br>Ala Gly Ser Ser Glu Gln Ala Ala Glu Ala Met Asp Ile Ala Ser Gln<br>        195                 200                 205 | 624 |
| gcc agg caa atg gtg cag gcg atg aga acc att ggg act cat cct agc<br>Ala Arg Gln Met Val Gln Ala Met Arg Thr Ile Gly Thr His Pro Ser<br>    210                 215                 220 | 672 |
| tcc agt gct ggt cta aaa gat gat ctt ctt gaa aat ttg cag gcc tat<br>Ser Ser Ala Gly Leu Lys Asp Asp Leu Leu Glu Asn Leu Gln Ala Tyr<br>225                 230                 235                 240 | 720 |

```
cag aaa cga atg ggg gtg cag atg caa cga ttc aag tga              759
Gln Lys Arg Met Gly Val Gln Met Gln Arg Phe Lys
            245                 250

<210> SEQ ID NO 22
<211> LENGTH: 252
<212> TYPE: PRT
<213> ORGANISM: Avian influenza virus

<400> SEQUENCE: 22

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Asp Ile Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
            245                 250

<210> SEQ ID NO 23
<211> LENGTH: 294
<212> TYPE: DNA
<213> ORGANISM: Avian influenza virus
<220> FEATURE:
<221> NAME/KEY: CDS
<222> LOCATION: (1)..(294)

<400> SEQUENCE: 23 atg agt ctt cta acc gag gtc gaa acg cct atc aga aac gaa tgg ggg    48
Met Ser Leu Leu Thr Glu Val Glu Thr Pro Ile Arg Asn Glu Trp Gly
1               5                   10                  15 tgc aga tgc aac gat tca agt gat cct ctc gtc att gca gca aat atc    96
Cys Arg Cys Asn Asp Ser Ser Asp Pro Leu Val Ile Ala Ala Asn Ile
            20                  25                  30
```

```
att gga atc ttg cac ttg ata ttg tgg att ctt gat cgt ctt ttt ttc      144
Ile Gly Ile Leu His Leu Ile Leu Trp Ile Leu Asp Arg Leu Phe Phe
            35                  40                  45 aaa tgc att tat cgt cgc ttt aaa tac ggt ttg aaa aga ggg cct tct      192
Lys Cys Ile Tyr Arg Arg Phe Lys Tyr Gly Leu Lys Arg Gly Pro Ser
 50                  55                  60 acg gaa gga gtg cca gag tct atg agg gaa gaa tat cga aag gaa cag      240
Thr Glu Gly Val Pro Glu Ser Met Arg Glu Glu Tyr Arg Lys Glu Gln
 65                  70                  75                  80 cag aat gct gtg gat gtt gac gat ggt cat ttt gtc aac ata gag ctg      288
Gln Asn Ala Val Asp Val Asp Asp Gly His Phe Val Asn Ile Glu Leu
            85                  90                  95 gag taa                                                              294
Glu

<210> SEQ ID NO 24
<211> LENGTH: 97
<212> TYPE: PRT
<213> ORGANISM: Avian influenza virus

<400> SEQUENCE: 24

Met Ser Leu Leu Thr Glu Val Glu Thr Pro Ile Arg Asn Glu Trp Gly
 1               5                  10                  15

Cys Arg Cys Asn Asp Ser Ser Asp Pro Leu Val Ile Ala Ala Asn Ile
            20                  25                  30

Ile Gly Ile Leu His Leu Ile Leu Trp Ile Leu Asp Arg Leu Phe Phe
            35                  40                  45

Lys Cys Ile Tyr Arg Arg Phe Lys Tyr Gly Leu Lys Arg Gly Pro Ser
 50                  55                  60

Thr Glu Gly Val Pro Glu Ser Met Arg Glu Glu Tyr Arg Lys Glu Gln
 65                  70                  75                  80

Gln Asn Ala Val Asp Val Asp Asp Gly His Phe Val Asn Ile Glu Leu
            85                  90                  95

Glu

<210> SEQ ID NO 25
<211> LENGTH: 1860
<212> TYPE: DNA
<213> ORGANISM: Artificial
<220> FEATURE:
<223> OTHER INFORMATION: cDNA of FliC-M2 fusion protein
<220> FEATURE:
<221> NAME/KEY: CDS
<222> LOCATION: (1)..(1860)

<400> SEQUENCE: 25 atg aaa ttc tta gtc aac gtt gcc ctt gtt ttt atg gtc gtg tac att       48
Met Lys Phe Leu Val Asn Val Ala Leu Val Phe Met Val Val Tyr Ile
 1               5                  10                  15 tct tac atc tat gcg gcc gca caa gtc att aat aca aac agc ctg tcg       96
Ser Tyr Ile Tyr Ala Ala Ala Gln Val Ile Asn Thr Asn Ser Leu Ser
            20                  25                  30 ctg ttg acc cag aat aac ctg aac aaa tcc cag tcc gct ctg ggc acc      144
Leu Leu Thr Gln Asn Asn Leu Asn Lys Ser Gln Ser Ala Leu Gly Thr
            35                  40                  45 gct atc gag cgt ctg tct tcc ggt ctg cgt atc aac agc gcg aaa gac      192
Ala Ile Glu Arg Leu Ser Ser Gly Leu Arg Ile Asn Ser Ala Lys Asp
 50                  55                  60 gat gcg gca ggt cag gcg att gct aac cgt ttt acc gcg aac atc aaa      240
Asp Ala Ala Gly Gln Ala Ile Ala Asn Arg Phe Thr Ala Asn Ile Lys
```

```
                 65                  70                  75                  80
ggt ctg act cag gct tcc cgt aac gct aac gac ggt atc tcc att gcg         288
Gly Leu Thr Gln Ala Ser Arg Asn Ala Asn Asp Gly Ile Ser Ile Ala
             85                  90                  95 cag acc act gaa ggc gcg ctg aac gaa atc aac aac aac ctg cag cgt         336
Gln Thr Thr Glu Gly Ala Leu Asn Glu Ile Asn Asn Asn Leu Gln Arg
        100                 105                 110 gtg cgt gaa ctg gcg gtt cag tct gct aac agc acc aac tcc cag tct         384
Val Arg Glu Leu Ala Val Gln Ser Ala Asn Ser Thr Asn Ser Gln Ser
    115                 120                 125 gac ctc gac tcc atc cag gct gaa atc acc cag cgc ctg aac gaa atc         432
Asp Leu Asp Ser Ile Gln Ala Glu Ile Thr Gln Arg Leu Asn Glu Ile
130                 135                 140 gac cgt gta tcc ggc cag act cag ttc aac ggc gtg aaa gtc ctg gcg         480
Asp Arg Val Ser Gly Gln Thr Gln Phe Asn Gly Val Lys Val Leu Ala
145                 150                 155                 160 cag gac aac acc ctg acc atc cag gtt ggt gcc aac gac ggt gaa act         528
Gln Asp Asn Thr Leu Thr Ile Gln Val Gly Ala Asn Asp Gly Glu Thr
        165                 170                 175 atc gat atc gat ctg aag cag atc aac tct cag acc ctg ggt ctg gat         576
Ile Asp Ile Asp Leu Lys Gln Ile Asn Ser Gln Thr Leu Gly Leu Asp
    180                 185                 190 acg ctg aat gtg caa caa aaa tat aag gtc agc gat acg gct gca act         624
Thr Leu Asn Val Gln Gln Lys Tyr Lys Val Ser Asp Thr Ala Ala Thr
195                 200                 205 gtt aca gga tat gcc gat act acg att gct tta gac aat agt act ttt         672
Val Thr Gly Tyr Ala Asp Thr Thr Ile Ala Leu Asp Asn Ser Thr Phe
        210                 215                 220 aaa gcc tcg gct act ggt ctt ggt ggt act gac cag aaa att gat ggc         720
Lys Ala Ser Ala Thr Gly Leu Gly Gly Thr Asp Gln Lys Ile Asp Gly
225                 230                 235                 240 gat tta aaa ttt gat gat acg act gga aaa tat tac gcc aaa gtt acc         768
Asp Leu Lys Phe Asp Asp Thr Thr Gly Lys Tyr Tyr Ala Lys Val Thr
                245                 250                 255 gtt acg ggg gga act ggt aaa gat ggc tat tat gaa gtt tcc gtt gat         816
Val Thr Gly Gly Thr Gly Lys Asp Gly Tyr Tyr Glu Val Ser Val Asp
            260                 265                 270 aag acg aac ggt gag gtg act ctt gct ggc ggt gcg act tcc ccg ctt         864
Lys Thr Asn Gly Glu Val Thr Leu Ala Gly Gly Ala Thr Ser Pro Leu
        275                 280                 285 aca ggt gga cta cct gcg aca gca act gag gat gtg aaa aat gta caa         912
Thr Gly Gly Leu Pro Ala Thr Ala Thr Glu Asp Val Lys Asn Val Gln
    290                 295                 300 gtt gca aat gct gat ttg aca gag gct aaa gcc gca ttg aca gca gca         960
Val Ala Asn Ala Asp Leu Thr Glu Ala Lys Ala Ala Leu Thr Ala Ala
305                 310                 315                 320 ggt gtt acc ggc aca gca tct gtt gtt aag atg tct tat act gat aat        1008
Gly Val Thr Gly Thr Ala Ser Val Val Lys Met Ser Tyr Thr Asp Asn
                325                 330                 335 aac ggt aaa act att gat ggt ggt tta gca gtt aag gta ggc gat gat        1056
Asn Gly Lys Thr Ile Asp Gly Gly Leu Ala Val Lys Val Gly Asp Asp
            340                 345                 350 tac tat tct gca act caa aat aaa gat ggt tcc ata agt att aat act        1104
Tyr Tyr Ser Ala Thr Gln Asn Lys Asp Gly Ser Ile Ser Ile Asn Thr
        355                 360                 365 acg aaa tac act gca gat gac ggt aca tcc aaa act gca cta aac aaa        1152
Thr Lys Tyr Thr Ala Asp Asp Gly Thr Ser Lys Thr Ala Leu Asn Lys
    370                 375                 380 ctg ggt ggc gca gac ggc aaa acc gaa gtt gtt tct att ggt ggt aaa        1200
Leu Gly Gly Ala Asp Gly Lys Thr Glu Val Val Ser Ile Gly Gly Lys
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Leu | Gly | Gly | Ala | Asp | Gly | Lys | Thr | Glu | Val | Val | Ser | Ile | Gly | Gly | Lys |      |
| 385 |     |     |     | 390 |     |     |     |     | 395 |     |     |     |     | 400 |     |      |

```
act tac gct gca agt aaa gcc gaa ggt cac aac ttt aaa gca cag cct       1248
Thr Tyr Ala Ala Ser Lys Ala Glu Gly His Asn Phe Lys Ala Gln Pro
                    405                 410                 415 gat ctg gcg gaa gcg gct gct aca acc acc gaa aac ccg ctg cag aaa       1296
Asp Leu Ala Glu Ala Ala Ala Thr Thr Thr Glu Asn Pro Leu Gln Lys
                420                 425                 430 att gat gct gct ttg gca cag gtt gac acg tta cgt tct gac ctg ggt       1344
Ile Asp Ala Ala Leu Ala Gln Val Asp Thr Leu Arg Ser Asp Leu Gly
            435                 440                 445 gcg gta cag aac cgt ttc aac tcc gct att acc aac ctg ggc aac acc       1392
Ala Val Gln Asn Arg Phe Asn Ser Ala Ile Thr Asn Leu Gly Asn Thr
        450                 455                 460 gta aac aac ctg act tct gcc cgt agc cgt atc gaa gat tcc gac tac       1440
Val Asn Asn Leu Thr Ser Ala Arg Ser Arg Ile Glu Asp Ser Asp Tyr
465                 470                 475                 480 gcg acc gaa gtt tcc aac atg tct cgc gcg cag att ctg cag cag gcc       1488
Ala Thr Glu Val Ser Asn Met Ser Arg Ala Gln Ile Leu Gln Gln Ala
                    485                 490                 495 ggt acc tcc gtt ctg gcg cag gcg aac cag gtt ccg caa aac gtc ctc       1536
Gly Thr Ser Val Leu Ala Gln Ala Asn Gln Val Pro Gln Asn Val Leu
                500                 505                 510 tct tta ctg cgt gga gga gga gga gga atg agt ctt cta acc gag           1584
Ser Leu Leu Arg Gly Gly Gly Gly Gly Met Ser Leu Leu Thr Glu
            515                 520                 525 gtc gaa acg cct atc aga aac gaa tgg ggg tgc aga tgc aac gat tca       1632
Val Glu Thr Pro Ile Arg Asn Glu Trp Gly Cys Arg Cys Asn Asp Ser
530                 535                 540 agt gat cct ctc gtc att gca gca aat atc att gga atc ttg cac ttg       1680
Ser Asp Pro Leu Val Ile Ala Ala Asn Ile Ile Gly Ile Leu His Leu
545                 550                 555                 560 ata ttg tgg att ctt gat cgt ctt ttt ttc aaa tgc att tat cgt cgc       1728
Ile Leu Trp Ile Leu Asp Arg Leu Phe Phe Lys Cys Ile Tyr Arg Arg
                    565                 570                 575 ttt aaa tac ggt ttg aaa aga ggg cct tct acg gaa gga gtg cca gag       1776
Phe Lys Tyr Gly Leu Lys Arg Gly Pro Ser Thr Glu Gly Val Pro Glu
                580                 585                 590 tct atg agg gaa gaa tat cga aag gaa cag cag aat gct gtg gat gtt       1824
Ser Met Arg Glu Glu Tyr Arg Lys Glu Gln Gln Asn Ala Val Asp Val
            595                 600                 605 gac gat ggt cat ttt gtc aac ata gag ctg gag taa                       1860
Asp Asp Gly His Phe Val Asn Ile Glu Leu Glu
        610                 615

<210> SEQ ID NO 26
<211> LENGTH: 619
<212> TYPE: PRT
<213> ORGANISM: Artificial
<220> FEATURE:
<223> OTHER INFORMATION: Synthetic Construct

<400> SEQUENCE: 26

Met Lys Phe Leu Val Asn Val Ala Leu Val Phe Met Val Val Tyr Ile
1               5                   10                  15

Ser Tyr Ile Tyr Ala Ala Ala Gln Val Ile Asn Thr Asn Ser Leu Ser
                20                  25                  30

Leu Leu Thr Gln Asn Asn Leu Asn Lys Ser Gln Ser Ala Leu Gly Thr
            35                  40                  45

Ala Ile Glu Arg Leu Ser Ser Gly Leu Arg Ile Asn Ser Ala Lys Asp
```

-continued

```
            50                  55                  60
Asp Ala Gly Gln Ala Ile Ala Asn Arg Phe Thr Ala Asn Ile Lys
 65                  70                  75                  80
Gly Leu Thr Gln Ala Ser Arg Asn Ala Asn Asp Gly Ile Ser Ile Ala
                     85                  90                  95
Gln Thr Thr Glu Gly Ala Leu Asn Glu Ile Asn Asn Leu Gln Arg
                100                 105                 110
Val Arg Glu Leu Ala Val Gln Ser Ala Asn Ser Thr Asn Ser Gln Ser
             115                 120                 125
Asp Leu Asp Ser Ile Gln Ala Glu Ile Thr Gln Arg Leu Asn Glu Ile
         130                 135                 140
Asp Arg Val Ser Gly Gln Thr Gln Phe Asn Gly Val Lys Val Leu Ala
145                 150                 155                 160
Gln Asp Asn Thr Leu Thr Ile Gln Val Gly Ala Asn Asp Gly Glu Thr
                     165                 170                 175
Ile Asp Ile Asp Leu Lys Gln Ile Asn Ser Gln Thr Leu Gly Leu Asp
                 180                 185                 190
Thr Leu Asn Val Gln Gln Lys Tyr Lys Val Ser Asp Thr Ala Ala Thr
             195                 200                 205
Val Thr Gly Tyr Ala Asp Thr Thr Ile Ala Leu Asp Asn Ser Thr Phe
         210                 215                 220
Lys Ala Ser Ala Thr Gly Leu Gly Gly Thr Asp Gln Lys Ile Asp Gly
225                 230                 235                 240
Asp Leu Lys Phe Asp Asp Thr Thr Gly Lys Tyr Tyr Ala Lys Val Thr
                     245                 250                 255
Val Thr Gly Gly Thr Gly Lys Asp Gly Tyr Tyr Glu Val Ser Val Asp
                 260                 265                 270
Lys Thr Asn Gly Glu Val Thr Leu Ala Gly Gly Ala Thr Ser Pro Leu
             275                 280                 285
Thr Gly Gly Leu Pro Ala Thr Ala Thr Glu Asp Val Lys Asn Val Gln
         290                 295                 300
Val Ala Asn Ala Asp Leu Thr Glu Ala Lys Ala Ala Leu Thr Ala Ala
305                 310                 315                 320
Gly Val Thr Gly Thr Ala Ser Val Val Lys Met Ser Tyr Thr Asp Asn
                     325                 330                 335
Asn Gly Lys Thr Ile Asp Gly Gly Leu Ala Val Lys Val Gly Asp Asp
                 340                 345                 350
Tyr Tyr Ser Ala Thr Gln Asn Lys Asp Gly Ser Ile Ser Ile Asn Thr
             355                 360                 365
Thr Lys Tyr Thr Ala Asp Asp Gly Thr Ser Lys Thr Ala Leu Asn Lys
         370                 375                 380
Leu Gly Gly Ala Asp Gly Lys Thr Glu Val Val Ser Ile Gly Gly Lys
385                 390                 395                 400
Thr Tyr Ala Ala Ser Lys Ala Glu Gly His Asn Phe Lys Ala Gln Pro
                     405                 410                 415
Asp Leu Ala Glu Ala Ala Thr Thr Thr Glu Asn Pro Leu Gln Lys
                 420                 425                 430
Ile Asp Ala Ala Leu Ala Gln Val Asp Thr Leu Arg Ser Asp Leu Gly
             435                 440                 445
Ala Val Gln Asn Arg Phe Asn Ser Ala Ile Thr Asn Leu Gly Asn Thr
         450                 455                 460
Val Asn Asn Leu Thr Ser Ala Arg Ser Arg Ile Glu Asp Ser Asp Tyr
465                 470                 475                 480
```

```
Ala Thr Glu Val Ser Asn Met Ser Arg Ala Gln Ile Leu Gln Gln Ala
            485                 490                 495

Gly Thr Ser Val Leu Ala Gln Ala Asn Gln Val Pro Gln Asn Val Leu
        500                 505                 510

Ser Leu Leu Arg Gly Gly Gly Gly Gly Met Ser Leu Leu Thr Glu
        515                 520                 525

Val Glu Thr Pro Ile Arg Asn Glu Trp Gly Cys Arg Cys Asn Asp Ser
    530                 535                 540

Ser Asp Pro Leu Val Ile Ala Ala Asn Ile Ile Gly Ile Leu His Leu
545                 550                 555                 560

Ile Leu Trp Ile Leu Asp Arg Leu Phe Phe Lys Cys Ile Tyr Arg Arg
                565                 570                 575

Phe Lys Tyr Gly Leu Lys Arg Gly Pro Ser Thr Glu Gly Val Pro Glu
            580                 585                 590

Ser Met Arg Glu Glu Tyr Arg Lys Glu Gln Gln Asn Ala Val Asp Val
            595                 600                 605

Asp Asp Gly His Phe Val Asn Ile Glu Leu Glu
    610                 615

<210> SEQ ID NO 27
<211> LENGTH: 1350
<212> TYPE: DNA
<213> ORGANISM: Avian influenza virus
<220> FEATURE:
<221> NAME/KEY: CDS
<222> LOCATION: (1)..(1350)

<400> SEQUENCE: 27 atg aat cca aat cag aag ata ata acc atc gga tca atc tgt atg gta      48
Met Asn Pro Asn Gln Lys Ile Ile Thr Ile Gly Ser Ile Cys Met Val
1               5                   10                  15 act gga ata gtt agc tta atg tta caa att ggg aac atg atc tca ata      96
Thr Gly Ile Val Ser Leu Met Leu Gln Ile Gly Asn Met Ile Ser Ile
                20                  25                  30 tgg gtc agt cat tca att cac aca ggg aat caa cac caa tct gaa cca     144
Trp Val Ser His Ser Ile His Thr Gly Asn Gln His Gln Ser Glu Pro
            35                  40                  45 atc agc aat act aat ttt ctt act gag aaa gct gtg gct tca gta aaa     192
Ile Ser Asn Thr Asn Phe Leu Thr Glu Lys Ala Val Ala Ser Val Lys
        50                  55                  60 tta gcg ggc aat tca tct ctt tgc ccc att aac gga tgg gct gta tac     240
Leu Ala Gly Asn Ser Ser Leu Cys Pro Ile Asn Gly Trp Ala Val Tyr
65                  70                  75                  80 agt aag gac aac agt ata agg atc ggt tcc aag ggg gat gtg ttt gtt     288
Ser Lys Asp Asn Ser Ile Arg Ile Gly Ser Lys Gly Asp Val Phe Val
                85                  90                  95 ata aga gag ccg ttc atc tca tgc tcc cac ttg gaa tgc aga act ttc     336
Ile Arg Glu Pro Phe Ile Ser Cys Ser His Leu Glu Cys Arg Thr Phe
            100                 105                 110 ttt ttg act cag gga gcc ttg ctg aat gac aag cac tcc aat ggg act     384
Phe Leu Thr Gln Gly Ala Leu Leu Asn Asp Lys His Ser Asn Gly Thr
        115                 120                 125 gtc aaa gac aga agc cct cac aga aca tta atg agt tgt cct gtg ggt     432
Val Lys Asp Arg Ser Pro His Arg Thr Leu Met Ser Cys Pro Val Gly
    130                 135                 140 gag gct ccc tcc cca tat aac tca agg ttt gag tct gtt gct tgg tca     480
Glu Ala Pro Ser Pro Tyr Asn Ser Arg Phe Glu Ser Val Ala Trp Ser
145                 150                 155                 160
```

```
gca agt gct tgc cat gat ggc acc agt tgg ttg acg att gga att tct    528
Ala Ser Ala Cys His Asp Gly Thr Ser Trp Leu Thr Ile Gly Ile Ser
            165                 170                 175 ggc cca gac aat ggg gct gtg gct gta ttg aaa tac aat ggc ata ata    576
Gly Pro Asp Asn Gly Ala Val Ala Val Leu Lys Tyr Asn Gly Ile Ile
        180                 185                 190 aca gac act atc aag agt tgg agg aac aac ata ctg aga act caa gag    624
Thr Asp Thr Ile Lys Ser Trp Arg Asn Asn Ile Leu Arg Thr Gln Glu
        195                 200                 205 tct gaa tgt gca tgt gta aat ggc tct tgc ttt act gta atg act gac    672
Ser Glu Cys Ala Cys Val Asn Gly Ser Cys Phe Thr Val Met Thr Asp
    210                 215                 220 gga cca agt aat ggt cag gca tca cat aag atc ttc aaa atg gaa aaa    720
Gly Pro Ser Asn Gly Gln Ala Ser His Lys Ile Phe Lys Met Glu Lys
225                 230                 235                 240 ggg aaa gtg gtt aaa tca gtc gaa ttg gat gct cct aat tat cac tat    768
Gly Lys Val Val Lys Ser Val Glu Leu Asp Ala Pro Asn Tyr His Tyr
                245                 250                 255 gag gaa tgc tcc tgt tat cct aat gcc gga gaa atc aca tgt gtg tgc    816
Glu Glu Cys Ser Cys Tyr Pro Asn Ala Gly Glu Ile Thr Cys Val Cys
            260                 265                 270 agg gat aat tgg cat ggc tca aat cgg cca tgg gta tct ttc aat caa    864
Arg Asp Asn Trp His Gly Ser Asn Arg Pro Trp Val Ser Phe Asn Gln
        275                 280                 285 aat ttg gag tat caa ata gga tat ata tgc agt gga gtt ttc gga gac    912
Asn Leu Glu Tyr Gln Ile Gly Tyr Ile Cys Ser Gly Val Phe Gly Asp
        290                 295                 300 aat cca cgc ccc aat gat gga aca ggt agt tgt ggt ccg gtg tcc tct    960
Asn Pro Arg Pro Asn Asp Gly Thr Gly Ser Cys Gly Pro Val Ser Ser
305                 310                 315                 320 aac ggg gca tat ggg gta aaa ggg ttt tca ttt aaa tac ggc aat ggt   1008
Asn Gly Ala Tyr Gly Val Lys Gly Phe Ser Phe Lys Tyr Gly Asn Gly
                325                 330                 335 gtc tgg atc ggg aga acc aaa agc act aat tcc agg agc ggc ttt gaa   1056
Val Trp Ile Gly Arg Thr Lys Ser Thr Asn Ser Arg Ser Gly Phe Glu
            340                 345                 350 atg att tgg gat cca aat ggg tgg act gaa acg gac agt agc ttt tca   1104
Met Ile Trp Asp Pro Asn Gly Trp Thr Glu Thr Asp Ser Ser Phe Ser
        355                 360                 365 gtg aaa caa gat atc gta gca ata act gat tgg tca gga tat agc ggg   1152
Val Lys Gln Asp Ile Val Ala Ile Thr Asp Trp Ser Gly Tyr Ser Gly
        370                 375                 380 agt ttt gtc cag cat cca gaa ctg aca gga cta gat tgc ata aga cct   1200
Ser Phe Val Gln His Pro Glu Leu Thr Gly Leu Asp Cys Ile Arg Pro
385                 390                 395                 400 tgt ttc tgg gtt gag ttg atc aga ggg cgg ccc aaa gag agc aca att   1248
Cys Phe Trp Val Glu Leu Ile Arg Gly Arg Pro Lys Glu Ser Thr Ile
                405                 410                 415 tgg act agt ggg agc agc ata tct ttt tgt ggt gta aat agt gac act   1296
Trp Thr Ser Gly Ser Ser Ile Ser Phe Cys Gly Val Asn Ser Asp Thr
            420                 425                 430 gtg ggt tgg tct tgg cca gac ggt gct gag ttg cca ttc acc att gac   1344
Val Gly Trp Ser Trp Pro Asp Gly Ala Glu Leu Pro Phe Thr Ile Asp
        435                 440                 445 aag tag                                                            1350
Lys

<210> SEQ ID NO 28
<211> LENGTH: 449
<212> TYPE: PRT
```

<213> ORGANISM: Avian influenza virus

<400> SEQUENCE: 28

```
Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asn Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Ser
        355                 360                 365

Val Lys Gln Asp Ile Val Ala Ile Thr Asp Trp Ser Gly Tyr Ser Gly
    370                 375                 380

Ser Phe Val Gln His Pro Glu Leu Thr Gly Leu Asp Cys Ile Arg Pro
385                 390                 395                 400
```

```
Cys Phe Trp Val Glu Leu Ile Arg Gly Arg Pro Lys Glu Ser Thr Ile
            405                 410                 415

Trp Thr Ser Gly Ser Ser Ile Ser Phe Cys Gly Val Asn Ser Asp Thr
        420                 425                 430

Val Gly Trp Ser Trp Pro Asp Gly Ala Glu Leu Pro Phe Thr Ile Asp
        435                 440                 445

Lys

<210> SEQ ID NO 29
<211> LENGTH: 1707
<212> TYPE: DNA
<213> ORGANISM: Avian influenza virus
<220> FEATURE:
<221> NAME/KEY: CDS
<222> LOCATION: (1)..(1707)

<400> SEQUENCE: 29 atg gag aaa ata gtg ctt ctt ctt gca ata gtc agt ctt gtt aaa agt    48
Met Glu Lys Ile Val Leu Leu Leu Ala Ile Val Ser Leu Val Lys Ser
1               5                   10                  15 gat cag att tgc att ggt tac cat gca aac aat tca aca gag cag gtt    96
Asp Gln Ile Cys Ile Gly Tyr His Ala Asn Asn Ser Thr Glu Gln Val
            20                  25                  30 gac aca atc atg gaa aag aac gtt act gtt aca cat gcc caa gac ata   144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag   192
Leu Glu Lys Thr His Asn Gly Lys Leu Cys Asp Leu Asp Gly Val Lys
    50                  55                  60 cct cta att tta aga gat tgt agt gta gct gga tgg ctc ctc ggg aac   240
Pro Leu Ile Leu Arg Asp Cys Ser Val Ala Gly Trp Leu Leu Gly Asn
65                  70                  75                  80 cca atg tgt gac gaa ttc atc aat gta ccg gaa tgg tct tac ata gtg   288
Pro Met Cys Asp Glu Phe Ile Asn Val Pro Glu Trp Ser Tyr Ile Val
                85                  90                  95 gag aag gcc aat cca acc aat gac ctc tgt tac cca ggg agt ttc aac   336
Glu Lys Ala Asn Pro Thr Asn Asp Leu Cys Tyr Pro Gly Ser Phe Asn
            100                 105                 110 gac tat gaa gaa ctg aaa cac cta ttg agc aga ata aac cat ttt gag   384
Asp Tyr Glu Glu Leu Lys His Leu Leu Ser Arg Ile Asn His Phe Glu
        115                 120                 125 aaa att caa atc atc ccc aaa agt tct tgg tcc gat cat gaa gcc tca   432
Lys Ile Gln Ile Ile Pro Lys Ser Ser Trp Ser Asp His Glu Ala Ser
    130                 135                 140 tca gga gtg agc tca gca tgt cca tac ctg gga agt ccc tcc ttt ttt   480
Ser Gly Val Ser Ser Ala Cys Pro Tyr Leu Gly Ser Pro Ser Phe Phe
145                 150                 155                 160 aga aat gtg gta tgg ctt atc aaa aag aac agt aca tac cca aca ata   528
Arg Asn Val Val Trp Leu Ile Lys Lys Asn Ser Thr Tyr Pro Thr Ile
                165                 170                 175 aag aaa agc tac aat aat acc aac caa gaa gat ctt ttg gta ctg tgg   576
Lys Lys Ser Tyr Asn Asn Thr Asn Gln Glu Asp Leu Leu Val Leu Trp
            180                 185                 190 gga att cac cat cct aat gat gcg gca gag cag aca agg cta tat caa   624
Gly Ile His His Pro Asn Asp Ala Ala Glu Gln Thr Arg Leu Tyr Gln
        195                 200                 205 aac cca acc acc tat att tcc att ggg aca tca aca cta aac cag aga   672
Asn Pro Thr Thr Tyr Ile Ser Ile Gly Thr Ser Thr Leu Asn Gln Arg
    210                 215                 220 ttg gta cca aaa ata gct act aga tcc aaa gta aac ggg caa agt gga   720
```

```
Leu Val Pro Lys Ile Ala Thr Arg Ser Lys Val Asn Gly Gln Ser Gly
225                 230                 235                 240 agg atg gag ttc ttc tgg aca att tta aaa cct aat gat gca atc aac      768
Arg Met Glu Phe Phe Trp Thr Ile Leu Lys Pro Asn Asp Ala Ile Asn
                245                 250                 255 ttc gag agt aat gga aat ttc att gct cca gaa tat gca tac aaa att      816
Phe Glu Ser Asn Gly Asn Phe Ile Ala Pro Glu Tyr Ala Tyr Lys Ile
            260                 265                 270 gtc aag aaa ggg gac tca gca att atg aaa agt gaa ttg gaa tat ggt      864
Val Lys Lys Gly Asp Ser Ala Ile Met Lys Ser Glu Leu Glu Tyr Gly
        275                 280                 285 aac tgc aac acc aag tgt caa act cca atg ggg gcg ata aac tct agt      912
Asn Cys Asn Thr Lys Cys Gln Thr Pro Met Gly Ala Ile Asn Ser Ser
    290                 295                 300 atg cca ttc cac aac ata cac cct ctc acc atc ggg gaa tgc ccc aaa      960
Met Pro Phe His Asn Ile His Pro Leu Thr Ile Gly Glu Cys Pro Lys
305                 310                 315                 320 tat gtg aaa tca aac aga tta gtc ctt gca aca ggg ctc aga aat agc     1008
Tyr Val Lys Ser Asn Arg Leu Val Leu Ala Thr Gly Leu Arg Asn Ser
                325                 330                 335 cct caa aga gag agc aga aga aaa aag aga gga cta ttt gga gct ata     1056
Pro Gln Arg Glu Ser Arg Arg Lys Lys Arg Gly Leu Phe Gly Ala Ile
            340                 345                 350 gca ggt ttt ata gag gga gga tgg cag gga atg gta gat ggt tgg tat     1104
Ala Gly Phe Ile Glu Gly Gly Trp Gln Gly Met Val Asp Gly Trp Tyr
        355                 360                 365 ggg tac cac cat agc aat gag cag ggg agt ggg tac gct gca gac aaa     1152
Gly Tyr His His Ser Asn Glu Gln Gly Ser Gly Tyr Ala Ala Asp Lys
    370                 375                 380 gaa tcc act caa aag gca ata gat gga gtc acc aat aag gtc aac tca     1200
Glu Ser Thr Gln Lys Ala Ile Asp Gly Val Thr Asn Lys Val Asn Ser
385                 390                 395                 400 atc att gac aaa atg aac act cag ttt gag gcc gtt gga agg gaa ttt     1248
Ile Ile Asp Lys Met Asn Thr Gln Phe Glu Ala Val Gly Arg Glu Phe
                405                 410                 415 aat aac tta gaa agg aga ata gag aat tta aac aag aag atg gaa gac     1296
Asn Asn Leu Glu Arg Arg Ile Glu Asn Leu Asn Lys Lys Met Glu Asp
            420                 425                 430 ggg ttt cta gat gtc tgg act tat aat gcc gaa ctt ctg gtt ctc atg     1344
Gly Phe Leu Asp Val Trp Thr Tyr Asn Ala Glu Leu Leu Val Leu Met
        435                 440                 445 gaa aat gag aga act cta gac ttt cat gac tca aat gtt aag aac ctc     1392
Glu Asn Glu Arg Thr Leu Asp Phe His Asp Ser Asn Val Lys Asn Leu
    450                 455                 460 tac gac aag gtc cga cta cag ctt agg gat aat gca aag gag ctg ggt     1440
Tyr Asp Lys Val Arg Leu Gln Leu Arg Asp Asn Ala Lys Glu Leu Gly
465                 470                 475                 480 aac ggt tgt ttc gag ttc tat cac aaa tgt gat aat gaa tgt atg gaa     1488
Asn Gly Cys Phe Glu Phe Tyr His Lys Cys Asp Asn Glu Cys Met Glu
                485                 490                 495 agt ata aga aac gga acg tac aac tat ccg cag tat tca gaa gaa gca     1536
Ser Ile Arg Asn Gly Thr Tyr Asn Tyr Pro Gln Tyr Ser Glu Glu Ala
            500                 505                 510 aga tta aaa aga gag gaa ata agt ggg gta aaa ttg gaa tca ata gga     1584
Arg Leu Lys Arg Glu Glu Ile Ser Gly Val Lys Leu Glu Ser Ile Gly
        515                 520                 525 act tac caa ata ctg tca att tat tca aca gtg gcg agt tcc cta gca     1632
Thr Tyr Gln Ile Leu Ser Ile Tyr Ser Thr Val Ala Ser Ser Leu Ala
    530                 535                 540
```

```
ctg gca atc atg atg gct ggt cta tct tta tgg atg tgc tcc aat gga    1680
Leu Ala Ile Met Met Ala Gly Leu Ser Leu Trp Met Cys Ser Asn Gly
545             550                 555                 560 tcg tta caa tgc aga att tgc att taa                                1707
Ser Leu Gln Cys Arg Ile Cys Ile
                565
```

```
<210> SEQ ID NO 30
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 30
```

```
atg gag aaa ata gtg ctt ctt ctt gca ata gtc agt ctt gtt aaa agt     48
Met Glu Lys Ile Val Leu Leu Leu Ala Ile Val Ser Leu Val Lys Ser
1               5                   10                  15 gat cag att tgc att ggt tac cat gca aac aac tcg aca gag cag gtt     96
Asp Gln Ile Cys Ile Gly Tyr His Ala Asn Asn Ser Thr Glu Gln Val
            20                  25                  30 gac aca ata atg gaa aag aac gtc act gtt aca cac gcc caa gac ata    144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag    192
Leu Glu Lys Thr His Asn Gly Lys Leu Cys Asp Leu Asp Gly Val Lys
50                  55                  60 cct cta att tta aga gat tgt agt gta gct gga tgg ctc ctc ggg aac    240
Pro Leu Ile Leu Arg Asp Cys Ser Val Ala Gly Trp Leu Leu Gly Asn
65                  70                  75                  80 cca atg tgt gac gaa ttc ctc aat gtg ccg gaa tgg tct tac ata gtg    288
Pro Met Cys Asp Glu Phe Leu Asn Val Pro Glu Trp Ser Tyr Ile Val
                85                  90                  95 gag aag atc aat cca gcc aat gac ctc tgt tac cca ggg aat ttc aac    336
Glu Lys Ile Asn Pro Ala Asn Asp Leu Cys Tyr Pro Gly Asn Phe Asn
            100                 105                 110 gac tat gaa gaa ctg aaa cac cta ttg agc aga ata aac cat ttt gag    384
Asp Tyr Glu Glu Leu Lys His Leu Leu Ser Arg Ile Asn His Phe Glu
        115                 120                 125 aaa att cag atc atc ccc aaa agt tct tgg tca gat cat gaa gcc tca    432
Lys Ile Gln Ile Ile Pro Lys Ser Ser Trp Ser Asp His Glu Ala Ser
130                 135                 140 tca ggg gtg agc tca gca tgt cca tac cag gga agg tcc tcc ttt ttt    480
Ser Gly Val Ser Ser Ala Cys Pro Tyr Gln Gly Arg Ser Ser Phe Phe
145                 150                 155                 160 aga aat gtg gta tgg ctt atc aaa aag aac aat gca tac cca aca ata    528
Arg Asn Val Val Trp Leu Ile Lys Lys Asn Asn Ala Tyr Pro Thr Ile
                165                 170                 175 aag aga agt tac aat aat acc aac caa gaa gat ctt ttg gta ctg tgg    576
Lys Arg Ser Tyr Asn Asn Thr Asn Gln Glu Asp Leu Leu Val Leu Trp
            180                 185                 190 ggg att cac cat cca aat gat gcg gca gag cag aca agg ctc tat caa    624
Gly Ile His His Pro Asn Asp Ala Ala Glu Gln Thr Arg Leu Tyr Gln
        195                 200                 205 aac cca acc acc tat att tcc gtt ggg aca tca aca cta aac cag aga    672
Asn Pro Thr Thr Tyr Ile Ser Val Gly Thr Ser Thr Leu Asn Gln Arg
210                 215                 220 ttg gta cca aaa ata gct act aga tcc aag gta aac ggg caa agt gga    720
Leu Val Pro Lys Ile Ala Thr Arg Ser Lys Val Asn Gly Gln Ser Gly
225                 230                 235                 240
```

```
agg atg gag ttc ttt tgg aca att tta aaa ccg aat gat gca ata aac       768
Arg Met Glu Phe Phe Trp Thr Ile Leu Lys Pro Asn Asp Ala Ile Asn
            245                 250                 255 ttt gag agt aat gga aat ttc att gct cca gaa aat gca tac aaa att       816
Phe Glu Ser Asn Gly Asn Phe Ile Ala Pro Glu Asn Ala Tyr Lys Ile
        260                 265                 270 gtc aag aaa ggg gac tca aca att atg aaa agt gaa ttg gaa tat ggt       864
Val Lys Lys Gly Asp Ser Thr Ile Met Lys Ser Glu Leu Glu Tyr Gly
    275                 280                 285 aac tgc aac acc aag tgt caa act cca ata ggg gcg ata aac tct agt       912
Asn Cys Asn Thr Lys Cys Gln Thr Pro Ile Gly Ala Ile Asn Ser Ser
290                 295                 300 atg cca ttc cac aac atc cac cct ctc acc atc ggg gaa tgc ccc aaa       960
Met Pro Phe His Asn Ile His Pro Leu Thr Ile Gly Glu Cys Pro Lys
305                 310                 315                 320 tat gtg aaa tca aac aga tta gtc ctt gcg act ggg ctc aga aat agc      1008
Tyr Val Lys Ser Asn Arg Leu Val Leu Ala Thr Gly Leu Arg Asn Ser
                325                 330                 335 cct caa att gaa act aga gga tta ttt gga gct ata gca ggt ttt ata      1056
Pro Gln Ile Glu Thr Arg Gly Leu Phe Gly Ala Ile Ala Gly Phe Ile
            340                 345                 350 gag gga gga tgg cag gga atg gta gat ggt tgg tat ggg tac cac cat      1104
Glu Gly Gly Trp Gln Gly Met Val Asp Gly Trp Tyr Gly Tyr His His
        355                 360                 365 agc aac gag cag ggg agt ggg tac gct gca gac aaa gaa tcc act caa      1152
Ser Asn Glu Gln Gly Ser Gly Tyr Ala Ala Asp Lys Glu Ser Thr Gln
    370                 375                 380 aag gca ata gat gga gtc acc aat aag gtc aac tcg atc att gac aaa      1200
Lys Ala Ile Asp Gly Val Thr Asn Lys Val Asn Ser Ile Ile Asp Lys
385                 390                 395                 400 atg aac act cag ttt gag gcc gtt gga agg gaa ttt aat aac tta gaa      1248
Met Asn Thr Gln Phe Glu Ala Val Gly Arg Glu Phe Asn Asn Leu Glu
                405                 410                 415 agg aga ata gaa aat tta aac aag aag atg gaa gac gga ttc cta gat      1296
Arg Arg Ile Glu Asn Leu Asn Lys Lys Met Glu Asp Gly Phe Leu Asp
            420                 425                 430 gtc tgg act tat aat gct gaa ctt ctg gtt ctc atg gaa aat gag aga      1344
Val Trp Thr Tyr Asn Ala Glu Leu Leu Val Leu Met Glu Asn Glu Arg
        435                 440                 445 act cta gac ttt cat gac tca aat gtc aag aac ctt tac gac aag gtc      1392
Thr Leu Asp Phe His Asp Ser Asn Val Lys Asn Leu Tyr Asp Lys Val
    450                 455                 460 cga cta cag ctt agg gat aat gca aag gag ctt ggt aac ggt tgt ttc      1440
Arg Leu Gln Leu Arg Asp Asn Ala Lys Glu Leu Gly Asn Gly Cys Phe
465                 470                 475                 480 gag ttc tat cac aga tgt gat aat gaa tgt atg gaa agt gta aga aac      1488
Glu Phe Tyr His Arg Cys Asp Asn Glu Cys Met Glu Ser Val Arg Asn
                485                 490                 495 gga acg tat gac tac ccg cag tat tca gaa gaa gca aga tta aaa aga      1536
Gly Thr Tyr Asp Tyr Pro Gln Tyr Ser Glu Glu Ala Arg Leu Lys Arg
            500                 505                 510 gag gaa ata agt gga gta aaa ttg gaa tca ata gga act tac caa ata      1584
Glu Glu Ile Ser Gly Val Lys Leu Glu Ser Ile Gly Thr Tyr Gln Ile
        515                 520                 525 ctg tca att tat tca aca gtg gcg agc tcc cta gca ctg gca atc atg      1632
Leu Ser Ile Tyr Ser Thr Val Ala Ser Ser Leu Ala Leu Ala Ile Met
    530                 535                 540 gtg gct ggt cta tct ttg tgg atg tgc tcc aat gga tcg tta caa tgc      1680
Val Ala Gly Leu Ser Leu Trp Met Cys Ser Asn Gly Ser Leu Gln Cys
545                 550                 555                 560
```

```
aga att tgc att taa                                                   1695
Arg Ile Cys Ile <210> SEQ ID NO 31
<211> LENGTH: 1704
<212> TYPE: DNA
<213> ORGANISM: Avian influenza virus
<220> FEATURE:
<221> NAME/KEY: CDS
<222> LOCATION: (1)..(1704)

<400> SEQUENCE: 31 atg gag aaa ata gtg ctt ctt ctt gca ata gtc agc ctt gtt aaa agt       48
Met Glu Lys Ile Val Leu Leu Leu Ala Ile Val Ser Leu Val Lys Ser
1               5                   10                  15 gat cag att tgc att ggt tac cat gca aac aac tcg aca gag cag gtt       96
Asp Gln Ile Cys Ile Gly Tyr His Ala Asn Asn Ser Thr Glu Gln Val
            20                  25                  30 gac aca ata atg gaa aag aac gtt act gtt aca cat gcc caa gac ata      144
Asp Thr Ile Met Glu Lys Asn Val Thr Val Thr His Ala Gln Asp Ile
        35                  40                  45 ctg gaa aag aca cac aac ggg aag ctc tgc gat cta gat gga gtg aag      192
Leu Glu Lys Thr His Asn Gly Lys Leu Cys Asp Leu Asp Gly Val Lys
    50                  55                  60 cct ctg att tta aga gat tgt agt gta gct gga tgg ctc ctc gga aac      240
Pro Leu Ile Leu Arg Asp Cys Ser Val Ala Gly Trp Leu Leu Gly Asn
65                  70                  75                  80 cca atg tgt gac gaa ttc atc aat gtg ccg gaa tgg tct tac ata gtg      288
Pro Met Cys Asp Glu Phe Ile Asn Val Pro Glu Trp Ser Tyr Ile Val
                85                  90                  95 gag aag gcc aac cca gcc aat gac ctc tgt tac cca ggg aat ttc aac      336
Glu Lys Ala Asn Pro Ala Asn Asp Leu Cys Tyr Pro Gly Asn Phe Asn
            100                 105                 110 gac tat gaa gaa ctg aaa cac cta ttg agc aga ata aac cat ttt gag      384
Asp Tyr Glu Glu Leu Lys His Leu Leu Ser Arg Ile Asn His Phe Glu
        115                 120                 125 aaa att cag atc atc ccc aaa agt tct tgg tcc gat cat gaa gcc tca      432
Lys Ile Gln Ile Ile Pro Lys Ser Ser Trp Ser Asp His Glu Ala Ser
    130                 135                 140 tca ggg gtg agc tca gca tgt cca tac cag gga acg ccc tcc ttt ttc      480
Ser Gly Val Ser Ser Ala Cys Pro Tyr Gln Gly Thr Pro Ser Phe Phe
145                 150                 155                 160 aga aat gtg gta tgg ctt atc aaa aag aac aat aca tac cca aca ata      528
Arg Asn Val Val Trp Leu Ile Lys Lys Asn Asn Thr Tyr Pro Thr Ile
                165                 170                 175 aag aga agc tac aat aat acc aac cag gaa gat ctt ttg ata ctg tgg      576
Lys Arg Ser Tyr Asn Asn Thr Asn Gln Glu Asp Leu Leu Ile Leu Trp
            180                 185                 190 ggg att cat cat tct aat gat gcg gca gag cag aca aag ctc tat caa      624
Gly Ile His His Ser Asn Asp Ala Ala Glu Gln Thr Lys Leu Tyr Gln
        195                 200                 205 aac cca acc acc tat att tcc gtt ggg aca tca aca cta aac cag aga      672
Asn Pro Thr Thr Tyr Ile Ser Val Gly Thr Ser Thr Leu Asn Gln Arg
    210                 215                 220 ttg gta cca aaa ata gct act aga tcc aaa gta aac ggg caa agt gga      720
Leu Val Pro Lys Ile Ala Thr Arg Ser Lys Val Asn Gly Gln Ser Gly
225                 230                 235                 240 agg atg gat ttc ttc tgg aca att tta aaa ccg aat gat gca atc aac      768
Arg Met Asp Phe Phe Trp Thr Ile Leu Lys Pro Asn Asp Ala Ile Asn
                245                 250                 255
```

-continued

| | |
|---|---|
| ttc gag agt aat gga aat ttc att gct cca gaa tat gca tac aaa att<br>Phe Glu Ser Asn Gly Asn Phe Ile Ala Pro Glu Tyr Ala Tyr Lys Ile<br>260                   265                   270 | 816 |
| gtc aag aaa ggg gac tca gca att gtt aaa agt gaa gtg gaa tat ggt<br>Val Lys Lys Gly Asp Ser Ala Ile Val Lys Ser Glu Val Glu Tyr Gly<br>275                   280                   285 | 864 |
| aac tgc aac aca aag tgt caa act cca ata ggg gcg ata aac tct agt<br>Asn Cys Asn Thr Lys Cys Gln Thr Pro Ile Gly Ala Ile Asn Ser Ser<br>290                   295                   300 | 912 |
| atg cca ttc cac aac ata cac cct ctc acc atc ggg gaa tgc ccc aaa<br>Met Pro Phe His Asn Ile His Pro Leu Thr Ile Gly Glu Cys Pro Lys<br>305                   310                   315                   320 | 960 |
| tat gtg aaa tca aac aaa tta gtc ctt gcg act ggg ctc aga aat agt<br>Tyr Val Lys Ser Asn Lys Leu Val Leu Ala Thr Gly Leu Arg Asn Ser<br>                 325                   330                   335 | 1008 |
| cct cta aga gaa aga aga aga aaa aga gga cta ttt gga gct ata gca<br>Pro Leu Arg Glu Arg Arg Arg Lys Arg Gly Leu Phe Gly Ala Ile Ala<br>                 340                   345                   350 | 1056 |
| ggg ttt ata gag gga gga tgg cag gga atg gta gat ggt tgg tat ggg<br>Gly Phe Ile Glu Gly Gly Trp Gln Gly Met Val Asp Gly Trp Tyr Gly<br>355                   360                   365 | 1104 |
| tac cac cat agc aat gag cag ggg agt ggg tac gct gca gac aaa gaa<br>Tyr His His Ser Asn Glu Gln Gly Ser Gly Tyr Ala Ala Asp Lys Glu<br>370                   375                   380 | 1152 |
| tcc act caa aag gca ata gat gga gtc acc aat aag gtc aac tcg atc<br>Ser Thr Gln Lys Ala Ile Asp Gly Val Thr Asn Lys Val Asn Ser Ile<br>385                   390                   395                   400 | 1200 |
| att gac aaa atg aac act cag ttt gag gcc gtt gga agg gaa ttt aat<br>Ile Asp Lys Met Asn Thr Gln Phe Glu Ala Val Gly Arg Glu Phe Asn<br>                 405                   410                   415 | 1248 |
| aac tta gaa agg aga ata gag aat tta aac aag aaa atg gaa gac gga<br>Asn Leu Glu Arg Arg Ile Glu Asn Leu Asn Lys Lys Met Glu Asp Gly<br>                 420                   425                   430 | 1296 |
| ttc cta gat gtc tgg act tat aat gct gaa ctt ctg gtt ctc atg gaa<br>Phe Leu Asp Val Trp Thr Tyr Asn Ala Glu Leu Leu Val Leu Met Glu<br>                 435                   440                   445 | 1344 |
| aat gag aga act cta gac ttc cat gat tca aat gtc aag aac ctt tac<br>Asn Glu Arg Thr Leu Asp Phe His Asp Ser Asn Val Lys Asn Leu Tyr<br>450                   455                   460 | 1392 |
| gac aag gtc cga cta cag ctt agg gat aat gca aag gag ctg ggt aac<br>Asp Lys Val Arg Leu Gln Leu Arg Asp Asn Ala Lys Glu Leu Gly Asn<br>465                   470                   475                   480 | 1440 |
| ggt tgt ttc gag ttc tat cac aaa tgt gat aat gaa tgt atg gaa agt<br>Gly Cys Phe Glu Phe Tyr His Lys Cys Asp Asn Glu Cys Met Glu Ser<br>                 485                   490                   495 | 1488 |
| gta aga aac gga acg tat gac tac ccg cag tat tca gaa gaa gca aga<br>Val Arg Asn Gly Thr Tyr Asp Tyr Pro Gln Tyr Ser Glu Glu Ala Arg<br>500                   505                   510 | 1536 |
| tta aaa aga gag gaa ata agt gga gta aaa ttg gaa tca ata gga act<br>Leu Lys Arg Glu Glu Ile Ser Gly Val Lys Leu Glu Ser Ile Gly Thr<br>515                   520                   525 | 1584 |
| tac caa ata ctg tca att tat tca aca gtt gcg agt tct cta gca ctg<br>Tyr Gln Ile Leu Ser Ile Tyr Ser Thr Val Ala Ser Ser Leu Ala Leu<br>530                   535                   540 | 1632 |
| gca atc atg gtg gct ggt cta tct ttg tgg atg tgc tcc aat ggg tcg<br>Ala Ile Met Val Ala Gly Leu Ser Leu Trp Met Cys Ser Asn Gly Ser<br>545                   550                   555                   560 | 1680 |
| tta caa tgc aga att tgc att taa<br>Leu Gln Cys Arg Ile Cys Ile<br>                 565 | 1704 |

```
<210> SEQ ID NO 32
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 32
```

| | | | | | | | | | | | | | | | | |
|---|---|---|---|---|---|---|---|---|---|---|---|---|---|---|---|---|
| atg | gag | aaa | att | gtc | ctg | ctg | ttc | gcc | att | gtc | tca | ctg | gtc | aaa | tcc | 48 |
| Met | Glu | Lys | Ile | Val | Leu | Leu | Phe | Ala | Ile | Val | Ser | Leu | Val | Lys | Ser | |
| 1 | | | | 5 | | | | | 10 | | | | | 15 | | |
| gat | cag | atc | tgt | att | ggc | tac | cac | gcc | aac | aat | agc | act | gaa | cag | gtc | 96 |
| Asp | Gln | Ile | Cys | Ile | Gly | Tyr | His | Ala | Asn | Asn | Ser | Thr | Glu | Gln | Val | |
| | | | 20 | | | | | 25 | | | | | 30 | | | |
| gac | act | att | atg | gaa | aaa | aac | gtg | acc | gtc | aca | cat | gct | cag | gat | att | 144 |
| Asp | Thr | Ile | Met | Glu | Lys | Asn | Val | Thr | Val | Thr | His | Ala | Gln | Asp | Ile | |
| | | 35 | | | | | 40 | | | | | 45 | | | | |
| ctc | gaa | aaa | acc | cac | aac | ggg | aaa | ctc | tgt | gat | ctc | gac | gga | gtg | aaa | 192 |
| Leu | Glu | Lys | Thr | His | Asn | Gly | Lys | Leu | Cys | Asp | Leu | Asp | Gly | Val | Lys | |
| | 50 | | | | | 55 | | | | | 60 | | | | | |
| cca | ctc | att | ctg | aga | gac | tgt | agc | gtc | gct | gga | tgg | ctc | ctc | ggc | aat | 240 |
| Pro | Leu | Ile | Leu | Arg | Asp | Cys | Ser | Val | Ala | Gly | Trp | Leu | Leu | Gly | Asn | |
| 65 | | | | | 70 | | | | | 75 | | | | | 80 | |
| cca | atg | tgt | gat | gag | ttc | atc | aac | gtc | ccc | gaa | tgg | tca | tac | atc | gtg | 288 |
| Pro | Met | Cys | Asp | Glu | Phe | Ile | Asn | Val | Pro | Glu | Trp | Ser | Tyr | Ile | Val | |
| | | | | 85 | | | | | 90 | | | | | 95 | | |
| gag | aag | gcc | aac | cct | gtg | aac | gat | ctc | tgt | tac | cct | ggc | gac | ttc | aac | 336 |
| Glu | Lys | Ala | Asn | Pro | Val | Asn | Asp | Leu | Cys | Tyr | Pro | Gly | Asp | Phe | Asn | |
| | | | 100 | | | | | 105 | | | | | 110 | | | |
| gat | tac | gag | gaa | ctg | aaa | cat | ctg | ctg | agt | agg | atc | aat | cac | ttt | gaa | 384 |
| Asp | Tyr | Glu | Glu | Leu | Lys | His | Leu | Leu | Ser | Arg | Ile | Asn | His | Phe | Glu | |
| | | | 115 | | | | | 120 | | | | | 125 | | | |
| aaa | att | cag | att | atc | ccc | aaa | tct | tcc | tgg | tcc | tcc | cat | gag | gca | tct | 432 |
| Lys | Ile | Gln | Ile | Ile | Pro | Lys | Ser | Ser | Trp | Ser | Ser | His | Glu | Ala | Ser | |
| | 130 | | | | | 135 | | | | | 140 | | | | | |
| ctg | ggc | gtg | tca | tct | gcc | tgt | cca | tac | aat | gga | acg | tcc | tca | ttc | ttc | 480 |
| Leu | Gly | Val | Ser | Ser | Ala | Cys | Pro | Tyr | Asn | Gly | Thr | Ser | Ser | Phe | Phe | |
| 145 | | | | | 150 | | | | | 155 | | | | | 160 | |
| cgg | aac | gtg | gtg | tgg | ctc | atc | aaa | aaa | aac | tcc | acc | tac | ccc | acc | atc | 528 |
| Arg | Asn | Val | Val | Trp | Leu | Ile | Lys | Lys | Asn | Ser | Thr | Tyr | Pro | Thr | Ile | |
| | | | | 165 | | | | | 170 | | | | | 175 | | |
| aaa | cgc | tct | tac | aac | aac | aca | aat | cag | gag | gat | ctg | ctg | gtc | ctc | tgg | 576 |
| Lys | Arg | Ser | Tyr | Asn | Asn | Thr | Asn | Gln | Glu | Asp | Leu | Leu | Val | Leu | Trp | |
| | | | 180 | | | | | 185 | | | | | 190 | | | |
| gga | att | cat | cac | ccc | aat | gat | gcc | gcc | gag | cag | aca | aaa | ctg | tac | cag | 624 |
| Gly | Ile | His | His | Pro | Asn | Asp | Ala | Ala | Glu | Gln | Thr | Lys | Leu | Tyr | Gln | |
| | | 195 | | | | | 200 | | | | | 205 | | | | |
| aac | cct | acc | aca | tac | att | tct | gtg | ggc | acc | tct | aca | ctg | aat | cag | agg | 672 |
| Asn | Pro | Thr | Thr | Tyr | Ile | Ser | Val | Gly | Thr | Ser | Thr | Leu | Asn | Gln | Arg | |
| | 210 | | | | | 215 | | | | | 220 | | | | | |
| ctg | gtg | cct | aga | att | gcc | act | agg | agt | aaa | gtc | aac | ggc | cag | tcc | ggc | 720 |
| Leu | Val | Pro | Arg | Ile | Ala | Thr | Arg | Ser | Lys | Val | Asn | Gly | Gln | Ser | Gly | |
| 225 | | | | | 230 | | | | | 235 | | | | | 240 | |
| cgg | atg | gaa | ttc | ttt | tgg | acc | atc | ctc | aaa | ccc | aac | gat | gct | atc | aac | 768 |
| Arg | Met | Glu | Phe | Phe | Trp | Thr | Ile | Leu | Lys | Pro | Asn | Asp | Ala | Ile | Asn | |
| | | | | 245 | | | | | 250 | | | | | 255 | | |
| ttc | gag | tca | aac | ggc | aac | ttt | atc | gcc | cct | gaa | tac | gcc | tac | aaa | atc | 816 |
| Phe | Glu | Ser | Asn | Gly | Asn | Phe | Ile | Ala | Pro | Glu | Tyr | Ala | Tyr | Lys | Ile | |
| | | | 260 | | | | | 265 | | | | | 270 | | | |

| | | |
|---|---|---|
| gtg aaa aag ggc gac tcc act atc atg aaa tcc gag ctg gag tac gga<br>Val Lys Lys Gly Asp Ser Thr Ile Met Lys Ser Glu Leu Glu Tyr Gly<br>275 280 285 | 864 | |
| aac tgt aac acc aaa tgc cag acc cct atg ggc gct atc aac tct tct<br>Asn Cys Asn Thr Lys Cys Gln Thr Pro Met Gly Ala Ile Asn Ser Ser<br>290 295 300 | 912 | |
| atg ccc ttc cac aac atc cac cct ctc act atc ggc gaa tgc cca aaa<br>Met Pro Phe His Asn Ile His Pro Leu Thr Ile Gly Glu Cys Pro Lys<br>305 310 315 320 | 960 | |
| tac gtc aaa tca aac cgg ctc gtg ctg gct act ggg ctg aga aac tca<br>Tyr Val Lys Ser Asn Arg Leu Val Leu Ala Thr Gly Leu Arg Asn Ser<br>325 330 335 | 1008 | |
| cct cag cga gag act aga ggc ctg ttt ggc gcc att gct gga ttc att<br>Pro Gln Arg Glu Thr Arg Gly Leu Phe Gly Ala Ile Ala Gly Phe Ile<br>340 345 350 | 1056 | |
| gag gga ggc tgg cag gga atg gtc gat ggc tgg tac gga tac cat cac<br>Glu Gly Gly Trp Gln Gly Met Val Asp Gly Trp Tyr Gly Tyr His His<br>355 360 365 | 1104 | |
| tcc aat gag cag gga tct gga tac gct gcc gat aag gag tcc acc cag<br>Ser Asn Glu Gln Gly Ser Gly Tyr Ala Ala Asp Lys Glu Ser Thr Gln<br>370 375 380 | 1152 | |
| aaa gca atc gat ggc gtc acc aac aaa gtc aat tca atc atc gac aaa<br>Lys Ala Ile Asp Gly Val Thr Asn Lys Val Asn Ser Ile Ile Asp Lys<br>385 390 395 400 | 1200 | |
| atg aac acc cag ttc gag gct gtg gga cga gag ttc aat aac ctg gag<br>Met Asn Thr Gln Phe Glu Ala Val Gly Arg Glu Phe Asn Asn Leu Glu<br>405 410 415 | 1248 | |
| cgg aga atc gaa aac ctg aac aaa aaa atg gag gac ggc ttc ctc gat<br>Arg Arg Ile Glu Asn Leu Asn Lys Lys Met Glu Asp Gly Phe Leu Asp<br>420 425 430 | 1296 | |
| gtg tgg acc tac aat gct gaa ctg ctg gtg ctc atg gaa aac gag aga<br>Val Trp Thr Tyr Asn Ala Glu Leu Leu Val Leu Met Glu Asn Glu Arg<br>435 440 445 | 1344 | |
| acc ctg gac ttc cac gac tca aac gtg aaa aac ctg tac gac aaa gtc<br>Thr Leu Asp Phe His Asp Ser Asn Val Lys Asn Leu Tyr Asp Lys Val<br>450 455 460 | 1392 | |
| cgg ctc cag ctg agg gat aat gcc aag gaa ctc gga aat ggc tgc ttc<br>Arg Leu Gln Leu Arg Asp Asn Ala Lys Glu Leu Gly Asn Gly Cys Phe<br>465 470 475 480 | 1440 | |
| gag ttc tac cac aaa tgt gac aac gag tgt atg gag tct gtc cga aac<br>Glu Phe Tyr His Lys Cys Asp Asn Glu Cys Met Glu Ser Val Arg Asn<br>485 490 495 | 1488 | |
| gga acc tac gac tac cct cag tac tct gag gag gct aga ctg aaa cga<br>Gly Thr Tyr Asp Tyr Pro Gln Tyr Ser Glu Glu Ala Arg Leu Lys Arg<br>500 505 510 | 1536 | |
| gag gag atc tct ggc gtc aaa ctg gag tct atc gga atc tac cag att<br>Glu Glu Ile Ser Gly Val Lys Leu Glu Ser Ile Gly Ile Tyr Gln Ile<br>515 520 525 | 1584 | |
| ctg tcc atc tac tct act gtg gct tct tca ctg gct ctg gcc atc atg<br>Leu Ser Ile Tyr Ser Thr Val Ala Ser Ser Leu Ala Leu Ala Ile Met<br>530 535 540 | 1632 | |
| gtc gct ggg ctg tct ctg tgg atg tgc tca aat gga tca ctc cag tgc<br>Val Ala Gly Leu Ser Leu Trp Met Cys Ser Asn Gly Ser Leu Gln Cys<br>545 550 555 560 | 1680 | |
| cgg atc tgt atc tag<br>Arg Ile Cys Ile | 1695 | |

<210> SEQ ID NO 33
<211> LENGTH: 548

```
<212> TYPE: PRT
<213> ORGANISM: Avian influenza virus
<220> FEATURE:
<221> NAME/KEY: mat_peptide
<222> LOCATION: (1)..(548)

<400> SEQUENCE: 33
```

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Asn Gly Thr Ser Ser Phe Phe
130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
370                 375                 380

```
Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
            405                 410                 415

Val Trp Thr Tyr Asn Ala Glu Leu Leu Val Leu Met Glu Asn Glu Arg
        420                 425                 430

Thr Leu Asp Phe His Asp Ser Asn Val Lys Asn Leu Tyr Asp Lys Val
    435                 440                 445

Arg Leu Gln Leu Arg Asp Asn Ala Lys Glu Leu Gly Asn Gly Cys Phe
450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
            485                 490                 495

Glu Glu Ile Ser Gly Val Lys Leu Glu Ser Ile Gly Ile Tyr Gln Ile
        500                 505                 510

Leu Ser Ile Tyr Ser Thr Val Ala Ser Ser Leu Ala Leu Ala Ile Met
    515                 520                 525

Val Ala Gly Leu Ser Leu Trp Met Cys Ser Asn Gly Ser Leu Gln Cys
530                 535                 540

Arg Ile Cys Ile
545

<210> SEQ ID NO 34
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 34

```
            130                 135                 140
tct ggc gtg tca tct gcc tgt cca tac cag agg aaa tcc tca ttc ttc    480
Ser Gly Val Ser Ser Ala Cys Pro Tyr Gln Arg Lys Ser Ser Phe Phe
145                 150                 155                 160 cgg aac gtg gtg tgg ctc atc aaa aaa aac tcc acc tac ccc acc atc    528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg    576
Lys Arg Ser Tyr Asn Asn Thr Asn Gln Glu Asp Leu Leu Val Leu Trp
            180                 185                 190 gga att cat cac ccc aat gat gcc gcc gag cag aca aaa ctg tac cag    624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg    672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc    720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac    768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc    816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga    864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct    912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa    960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca   1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att   1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac   1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag   1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa   1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag   1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat   1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga   1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc   1392
```

-continued

```
Thr Leu Asp Phe His Asp Ser Asn Val Lys Asn Leu Tyr Asp Lys Val
        450                 455                 460 cgg ctc cag ctg agg gat aat gcc aag gaa ctc gga aat ggc tgc ttc      1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac      1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga      1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att      1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg      1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc      1680
Val Ala Gly Leu Ser Leu Trp Met Cys Ser Asn Gly Ser Leu Gln Cys
545                 550                 555                 560 cgg atc tgt atc tag                                                  1695
Arg Ile Cys Ile <210> SEQ ID NO 35
<211> LENGTH: 548
<212> TYPE: PRT
<213> ORGANISM: Avian influenza virus
<220> FEATURE:
<221> NAME/KEY: mat_peptide
<222> LOCATION: (1)..(548)

<400> SEQUENCE: 35

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Asn Asn Thr Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Asn Ser
        115                 120                 125

Ser Gly Val Ser Ser Ala Cys Pro Tyr Gln Arg Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205
```

```
Leu Val Pro Arg Ile Ala Thr Arg Ser Lys Val Asn Gly Gln Ser Gly
            210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
                275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
                355                 360                 365

Lys Ala Ile Asp Gly Val Thr Asn Lys Val Asn Ser Ile Ile Asp Lys
370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
                435                 440                 445

Arg Leu Gln Leu Arg Asp Asn Ala Lys Glu Leu Gly Asn Gly Cys Phe
450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Ile Tyr Gln Ile
            500                 505                 510

Leu Ser Ile Tyr Ser Thr Val Ala Ser Ser Leu Ala Leu Ala Ile Met
                515                 520                 525

Val Ala Gly Leu Ser Leu Trp Met Cys Ser Asn Gly Ser Leu Gln Cys
530                 535                 540

Arg Ile Cys Ile
545

<210> SEQ ID NO 36
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 36 atg gag aaa att gtc ctg ctg ttc gcc att gtc tca ctg gtc aaa tcc     48
```

```
                Met Glu Lys Ile Val Leu Leu Phe Ala Ile Val Ser Leu Val Lys Ser
                1               5                   10                  15 gat cag atc tgt att ggc tac cac gcc aac aat agc act gaa cag gtc         96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att         144
Asp Thr Ile Met Glu Lys Asn Val Thr Val Thr His Ala Gln Asp Ile
                35                  40                  45 ctc gaa aaa acc cac aac ggg aaa ctc tgt gat ctc gac gga gtg aaa         192
Leu Glu Lys Thr His Asn Gly Lys Leu Cys Asp Leu Asp Gly Val Lys
        50                  55                  60 cca ctc att ctg aga gac tgt agc gtc gct gga tgg ctc ctc ggc aat         240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg         288
Pro Met Cys Asp Glu Phe Ile Asn Val Pro Glu Trp Ser Tyr Ile Val
                85                  90                  95 gag aag gcc aac cct gtg aac gat ctc tgt tac cct ggc gac ttc aac         336
Glu Lys Ala Asn Pro Val Asn Asp Leu Cys Tyr Pro Gly Asp Phe Asn
                100                 105                 110 gat tac gag gaa ctg aaa cat ctg ctg agt agg atc aat cac ttt gaa         384
Asp Tyr Glu Glu Leu Lys His Leu Leu Ser Arg Ile Asn His Phe Glu
            115                 120                 125 aaa att cag att atc ccc aaa tct tcc tgg tcc tcc cat gag aac tct         432
Lys Ile Gln Ile Ile Pro Lys Ser Ser Trp Ser Ser His Glu Asn Ser
        130                 135                 140 tct ggc gtg tca tct gcc tgt cca tac aat gga acg tcc tca ttc ttc         480
Ser Gly Val Ser Ser Ala Cys Pro Tyr Asn Gly Thr Ser Ser Phe Phe
145                 150                 155                 160 cgg aac gtg gtg tgg ctc atc aaa aaa aac tcc acc tac ccc acc atc         528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg         576
Lys Arg Ser Tyr Asn Asn Thr Asn Gln Glu Asp Leu Leu Val Leu Trp
                180                 185                 190 gga att cat cac ccc aat gat gcc gcc gag cag aca aaa ctg tac cag         624
Gly Ile His His Pro Asn Asp Ala Ala Glu Gln Thr Lys Leu Tyr Gln
            195                 200                 205 aac cct acc aca tac att tct gtg ggc acc tct aca ctg aat cag agg         672
Asn Pro Thr Thr Tyr Ile Ser Val Gly Thr Ser Thr Leu Asn Gln Arg
        210                 215                 220 ctg gtg cct aga att gcc act agg agt aaa gtc aac ggc cag tcc ggc         720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac         768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc         816
Phe Glu Ser Asn Gly Asn Phe Ile Ala Pro Glu Tyr Ala Tyr Lys Ile
                260                 265                 270 gtg aaa aag ggc gac tcc act atc atg aaa tcc gag ctg gag tac gga         864
Val Lys Lys Gly Asp Ser Thr Ile Met Lys Ser Glu Leu Glu Tyr Gly
            275                 280                 285 aac tgt aac acc aaa tgc cag acc cct atg ggc gct atc aac tct tct         912
Asn Cys Asn Thr Lys Cys Gln Thr Pro Met Gly Ala Ile Asn Ser Ser
        290                 295                 300 atg ccc ttc cac aac atc cac cct ctc act atc ggc gaa tgc cca aaa         960
Met Pro Phe His Asn Ile His Pro Leu Thr Ile Gly Glu Cys Pro Lys
305                 310                 315                 320
```

-continued

| | | |
|---|---|---|
| tac gtc aaa tca aac cgg ctc gtg ctg gct act ggg ctg aga aac tca<br>Tyr Val Lys Ser Asn Arg Leu Val Leu Ala Thr Gly Leu Arg Asn Ser<br>                  325                          330                       335 | 1008 |
| cct cag cga gag act aga ggc ctg ttt ggc gcc att gct gga ttc att<br>Pro Gln Arg Glu Thr Arg Gly Leu Phe Gly Ala Ile Ala Gly Phe Ile<br>340                       345                          350 | 1056 |
| gag gga ggc tgg cag gga atg gtc gat ggc tgg tac gga tac cat cac<br>Glu Gly Gly Trp Gln Gly Met Val Asp Gly Trp Tyr Gly Tyr His His<br>            355                        360                       365 | 1104 |
| tcc aat gag cag gga tct gga tac gct gcc gat aag gag tcc acc cag<br>Ser Asn Glu Gln Gly Ser Gly Tyr Ala Ala Asp Lys Glu Ser Thr Gln<br>       370                       375                       380 | 1152 |
| aaa gca atc gat ggc gtc acc aac aaa gtc aat tca atc atc gac aaa<br>Lys Ala Ile Asp Gly Val Thr Asn Lys Val Asn Ser Ile Ile Asp Lys<br>385                     390                     395                   400 | 1200 |
| atg aac acc cag ttc gag gct gtg gga cga gag ttc aat aac ctg gag<br>Met Asn Thr Gln Phe Glu Ala Val Gly Arg Glu Phe Asn Asn Leu Glu<br>                                   405                       410                   415 | 1248 |
| cgg aga atc gaa aac ctg aac aaa aaa atg gag gac ggc ttc ctc gat<br>Arg Arg Ile Glu Asn Leu Asn Lys Lys Met Glu Asp Gly Phe Leu Asp<br>                420                          425                       430 | 1296 |
| gtg tgg acc tac aat gct gaa ctg ctg gtg ctc atg gaa aac gag aga<br>Val Trp Thr Tyr Asn Ala Glu Leu Leu Val Leu Met Glu Asn Glu Arg<br>            435                        440                       445 | 1344 |
| acc ctg gac ttc cac gac tca aac gtg aaa aac ctg tac gac aaa gtc<br>Thr Leu Asp Phe His Asp Ser Asn Val Lys Asn Leu Tyr Asp Lys Val<br>     450                       455                       460 | 1392 |
| cgg ctc cag ctg agg gat aat gcc aag gaa ctc gga aat ggc tgc ttc<br>Arg Leu Gln Leu Arg Asp Asn Ala Lys Glu Leu Gly Asn Gly Cys Phe<br>465                     470                     475                   480 | 1440 |
| gag ttc tac cac aaa tgt gac aac gag tgt atg gag tct gtc cga aac<br>Glu Phe Tyr His Lys Cys Asp Asn Glu Cys Met Glu Ser Val Arg Asn<br>                                 485                       490                   495 | 1488 |
| gga acc tac gac tac cct cag tac tct gag gag gct aga ctg aaa cga<br>Gly Thr Tyr Asp Tyr Pro Gln Tyr Ser Glu Glu Ala Arg Leu Lys Arg<br>            500                       505                       510 | 1536 |
| gag gag atc tct ggc gtc aaa ctg gag tct atc gga atc tac cag att<br>Glu Glu Ile Ser Gly Val Lys Leu Glu Ser Ile Gly Ile Tyr Gln Ile<br>                515                        520                       525 | 1584 |
| ctg tcc atc tac tct act gtg gct tct tca ctg gct ctg gcc atc atg<br>Leu Ser Ile Tyr Ser Thr Val Ala Ser Ser Leu Ala Leu Ala Ile Met<br>       530                       535                       540 | 1632 |
| gtc gct ggg ctg tct ctg tgg atg tgc tca aat gga tca ctc cag tgc<br>Val Ala Gly Leu Ser Leu Trp Met Cys Ser Asn Gly Ser Leu Gln Cys<br>545                     550                     555                   560 | 1680 |
| cgg atc tgt atc tag<br>Arg Ile Cys Ile | 1695 |

```
<210> SEQ ID NO 37
<211> LENGTH: 548
<212> TYPE: PRT
<213> ORGANISM: Avian influenza virus
<220> FEATURE:
<221> NAME/KEY: mat_peptide
<222> LOCATION: (1)..(548)

<400> SEQUENCE: 37
```

Asp Gln Ile Cys Ile Gly Tyr His Ala Asn Asn Ser Thr Glu Gln Val
1               5                  10                  15

Asp Thr Ile Met Glu Lys Asn Val Thr Val Thr His Ala Gln Asp Ile
                   20                  25                  30

```
Leu Glu Lys Thr His Asn Gly Lys Leu Cys Asp Leu Asp Gly Val Lys
         35                  40                  45

Pro Leu Ile Leu Arg Asp Cys Ser Val Ala Gly Trp Leu Leu Gly Asn
         50                  55                  60

Pro Met Cys Asp Glu Phe Ile Asn Val Pro Glu Trp Ser Tyr Ile Val
 65                  70                  75                  80

Glu Lys Ala Asn Pro Val Asn Asp Leu Cys Tyr Pro Gly Asp Phe Asn
                     85                  90                  95

Asp Tyr Glu Glu Leu Lys His Leu Leu Ser Arg Ile Asn His Phe Glu
                100                 105                 110

Lys Ile Gln Ile Ile Pro Lys Ser Ser Trp Ser His Glu Asn Ser
        115                 120                 125

Ser Gly Val Ser Ser Ala Cys Pro Tyr Asn Gly Thr Ser Ser Phe Phe
        130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
                180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
        210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
                260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
        290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
                340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
        370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
                420                 425                 430

Thr Leu Asp Phe His Asp Ser Asn Val Lys Asn Leu Tyr Asp Lys Val
        435                 440                 445
```

```
Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Ile Tyr Gln Ile
            500                 505                 510

Leu Ser Ile Tyr Ser Thr Val Ala Ser Ser Leu Ala Leu Ala Ile Met
        515                 520                 525

Val Ala Gly Leu Ser Leu Trp Met Cys Ser Asn Gly Ser Leu Gln Cys
530                 535                 540

Arg Ile Cys Ile
545

<210> SEQ ID NO 38
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 38 atg gag aaa att gtc ctg ctg ttc gcc att gtc tca ctg gtc aaa tcc       48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc       96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att      144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa      192
Leu Glu Lys Thr His Asn Gly Lys Leu Cys Asp Leu Asp Gly Val Lys
    50                  55                  60 cca ctc att ctg aga gac tgt agc gtc gct gga tgg ctc ctc ggc aat      240
Pro Leu Ile Leu Arg Asp Cys Ser Val Ala Gly Trp Leu Leu Gly Asn
65                  70                  75                  80 cca atg tgt gat gag ttc atc aac gtc ccc gaa tgg tca tac atc gtg      288
Pro Met Cys Asp Glu Phe Ile Asn Val Pro Glu Trp Ser Tyr Ile Val
                85                  90                  95 gag aag aac aac acc gtg aac gat ctc tgt tac cct ggc gac ttc aac      336
Glu Lys Asn Asn Thr Val Asn Asp Leu Cys Tyr Pro Gly Asp Phe Asn
            100                 105                 110 gat tac gag gaa ctg aaa cat ctg ctg agt agg atc aat cac ttt gaa      384
Asp Tyr Glu Glu Leu Lys His Leu Leu Ser Arg Ile Asn His Phe Glu
        115                 120                 125 aaa att cag att atc ccc aaa tct tcc tgg tcc tcc cat gag gca tct      432
Lys Ile Gln Ile Ile Pro Lys Ser Ser Trp Ser Ser His Glu Ala Ser
    130                 135                 140 ctg ggc gtg tca tct gcc tgt cca tac aat gga acg tcc tca ttc ttc      480
Leu Gly Val Ser Ser Ala Cys Pro Tyr Asn Gly Thr Ser Ser Phe Phe
145                 150                 155                 160 cgg aac gtg gtg tgg ctc atc aaa aaa aac tcc acc tac ccc acc atc      528
Arg Asn Val Val Trp Leu Ile Lys Lys Asn Ser Thr Tyr Pro Thr Ile
                165                 170                 175 aaa cgc tct tac aac aac aca aat cag gag gat ctg ctg gtc ctc tgg      576
Lys Arg Ser Tyr Asn Asn Thr Asn Gln Glu Asp Leu Leu Val Leu Trp
            180                 185                 190
```

```
gga att cat cac ccc aat gat gcc gcc gag cag aca aaa ctg tac cag      624
Gly Ile His His Pro Asn Asp Ala Ala Glu Gln Thr Lys Leu Tyr Gln
        195                 200                 205 aac cct acc aca tac att tct gtg ggc acc tct aca ctg aat cag agg      672
Asn Pro Thr Thr Tyr Ile Ser Val Gly Thr Ser Thr Leu Asn Gln Arg
    210                 215                 220 ctg gtg cct aga att gcc act agg agt aaa gtc aac ggc cag tcc ggc      720
Leu Val Pro Arg Ile Ala Thr Arg Ser Lys Val Asn Gly Gln Ser Gly
225                 230                 235                 240 cgg atg gaa ttc ttt tgg acc atc ctc aaa ccc aac gat gct atc aac      768
Arg Met Glu Phe Phe Trp Thr Ile Leu Lys Pro Asn Asp Ala Ile Asn
                245                 250                 255 ttc gag tca aac ggc aac ttt atc gcc cct gaa tac gcc tac aaa atc      816
Phe Glu Ser Asn Gly Asn Phe Ile Ala Pro Glu Tyr Ala Tyr Lys Ile
            260                 265                 270 gtg aaa aag ggc gac tcc act atc atg aaa tcc gag ctg gag tac gga      864
Val Lys Lys Gly Asp Ser Thr Ile Met Lys Ser Glu Leu Glu Tyr Gly
        275                 280                 285 aac tgt aac acc aaa tgc cag acc cct atg ggc gct atc aac tct tct      912
Asn Cys Asn Thr Lys Cys Gln Thr Pro Met Gly Ala Ile Asn Ser Ser
    290                 295                 300 atg ccc ttc cac aac atc cac cct ctc act atc ggc gaa tgc cca aaa      960
Met Pro Phe His Asn Ile His Pro Leu Thr Ile Gly Glu Cys Pro Lys
305                 310                 315                 320 tac gtc aaa tca aac cgg ctc gtg ctg gct act ggg ctg aga aac tca     1008
Tyr Val Lys Ser Asn Arg Leu Val Leu Ala Thr Gly Leu Arg Asn Ser
                325                 330                 335 cct cag cga gag act aga ggc ctg ttt ggc gcc att gct gga ttc att     1056
Pro Gln Arg Glu Thr Arg Gly Leu Phe Gly Ala Ile Ala Gly Phe Ile
            340                 345                 350 gag gga ggc tgg cag gga atg gtc gat ggc tgg tac gga tac cat cac     1104
Glu Gly Gly Trp Gln Gly Met Val Asp Gly Trp Tyr Gly Tyr His His
        355                 360                 365 tcc aat gag cag gga tct gga tac gct gcc gat aag gag tcc acc cag     1152
Ser Asn Glu Gln Gly Ser Gly Tyr Ala Ala Asp Lys Glu Ser Thr Gln
    370                 375                 380 aaa gca atc gat ggc gtc acc aac aaa gtc aat tca atc atc gac aaa     1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag     1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat     1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga     1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc     1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc     1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac     1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga     1536
Gly Thr Tyr Asp Tyr Pro Gln Tyr Ser Glu Glu Ala Arg Leu Lys Arg
```

-continued

```
                        500                    505                     510
gag gag atc tct ggc gtc aaa ctg gag tct atc gga atc tac cag att         1584
Glu Glu Ile Ser Gly Val Lys Leu Glu Ser Ile Gly Ile Tyr Gln Ile
            515                    520                     525 ctg tcc atc tac tct act gtg gct tct tca ctg gct ctg gcc atc atg         1632
Leu Ser Ile Tyr Ser Thr Val Ala Ser Ser Leu Ala Leu Ala Ile Met
    530                    535                     540 gtc gct ggg ctg tct ctg tgg atg tgc tca aat gga tca ctc cag tgc         1680
Val Ala Gly Leu Ser Leu Trp Met Cys Ser Asn Gly Ser Leu Gln Cys
545                    550                     555                 560 cgg atc tgt atc tag                                                     1695
Arg Ile Cys Ile <210> SEQ ID NO 39
<211> LENGTH: 548
<212> TYPE: PRT
<213> ORGANISM: Avian influenza virus
<220> FEATURE:
<221> NAME/KEY: mat_peptide
<222> LOCATION: (1)..(548)

<400> SEQUENCE: 39

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Asn Asn Thr Val Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Asn Gly Thr Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270
```

-continued

```
Asn Cys Asn Thr Lys Cys Gln Thr Pro Met Gly Ala Ile Asn Ser Ser
            275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Ile Tyr Gln Ile
            500                 505                 510

Leu Ser Ile Tyr Ser Thr Val Ala Ser Ser Leu Ala Leu Ala Ile Met
        515                 520                 525

Val Ala Gly Leu Ser Leu Trp Met Cys Ser Asn Gly Ser Leu Gln Cys
    530                 535                 540

Arg Ile Cys Ile
545
```

<210> SEQ ID NO 40
<211> LENGTH: 1695
<212> TYPE: DNA
<213> ORGANISM: Avian influenza virus
<220> FEATURE:
<221> NAME/KEY: CDS
<222> LOCATION: (1)..(1695)

<400> SEQUENCE: 40

```
atg gag aaa att gtc ctg ctg ttc gcc att gtc tca ctg gtc aaa tcc      48
Met Glu Lys Ile Val Leu Leu Phe Ala Ile Val Ser Leu Val Lys Ser
1               5                   10                  15 gat cag atc tgt att ggc tac cac gcc aac aat agc act gaa cag gtc      96
Asp Gln Ile Cys Ile Gly Tyr His Ala Asn Asn Ser Thr Glu Gln Val
            20                  25                  30 gac act att atg gaa aaa aac gtg acc gtc aca cat gct cag gat att     144
Asp Thr Ile Met Glu Lys Asn Val Thr Val Thr His Ala Gln Asp Ile
        35                  40                  45 ctc gaa aaa acc cac aac ggg aaa ctc tgt gat ctc gac gga gtg aaa     192
Leu Glu Lys Thr His Asn Gly Lys Leu Cys Asp Leu Asp Gly Val Lys
```

-continued

```
                50                   55                   60
cca ctc att ctg aga gac tgt agc gtc gct gga tgg ctc ctc ggc aat     240
Pro Leu Ile Leu Arg Asp Cys Ser Val Ala Gly Trp Leu Leu Gly Asn
 65                  70                   75                  80 cca atg tgt gat gag ttc atc aac gtc ccc gaa tgg tca tac atc gtg     288
Pro Met Cys Asp Glu Phe Ile Asn Val Pro Glu Trp Ser Tyr Ile Val
                 85                   90                   95 gag aag aac aac acc gtg aac gat ctc tgt tac cct ggc gac ttc aac     336
Glu Lys Asn Asn Thr Val Asn Asp Leu Cys Tyr Pro Gly Asp Phe Asn
            100                  105                  110 gat tac gag gaa ctg aaa cat ctg ctg agt agg atc aat cac ttt gaa     384
Asp Tyr Glu Glu Leu Lys His Leu Leu Ser Arg Ile Asn His Phe Glu
        115                  120                  125 aaa att cag att atc ccc aaa tct tcc tgg tcc tcc cat gag aac tct     432
Lys Ile Gln Ile Ile Pro Lys Ser Ser Trp Ser Ser His Glu Asn Ser
130                  135                  140 tct ggc gtg tca tct gcc tgt cca tac aat gga acg tcc tca ttc ttc     480
Ser Gly Val Ser Ser Ala Cys Pro Tyr Asn Gly Thr Ser Ser Phe Phe
145                  150                  155                  160 cgg aac gtg gtg tgg ctc atc aaa aaa aac tcc acc tac ccc acc atc     528
Arg Asn Val Val Trp Leu Ile Lys Lys Asn Ser Thr Tyr Pro Thr Ile
                165                  170                  175 aaa cgc tct tac aac aac aca aat cag gag gat ctg ctg gtc ctc tgg     576
Lys Arg Ser Tyr Asn Asn Thr Asn Gln Glu Asp Leu Leu Val Leu Trp
            180                  185                  190 gga att cat cac ccc aat gat gcc gcc gag cag aca aaa ctg tac cag     624
Gly Ile His His Pro Asn Asp Ala Ala Glu Gln Thr Lys Leu Tyr Gln
        195                  200                  205 aac cct acc aca tac att tct gtg ggc acc tct aca ctg aat cag agg     672
Asn Pro Thr Thr Tyr Ile Ser Val Gly Thr Ser Thr Leu Asn Gln Arg
    210                  215                  220 ctg gtg cct aga att gcc act agg agt aaa gtc aac ggc cag tcc ggc     720
Leu Val Pro Arg Ile Ala Thr Arg Ser Lys Val Asn Gly Gln Ser Gly
225                  230                  235                  240 cgg atg gaa ttc ttt tgg acc atc ctc aaa ccc aac gat gct atc aac     768
Arg Met Glu Phe Phe Trp Thr Ile Leu Lys Pro Asn Asp Ala Ile Asn
                245                  250                  255 ttc gag tca aac ggc aac ttt atc gcc cct gaa tac gcc tac aaa atc     816
Phe Glu Ser Asn Gly Asn Phe Ile Ala Pro Glu Tyr Ala Tyr Lys Ile
            260                  265                  270 gtg aaa aag ggc gac tcc act atc atg aaa tcc gag ctg gag tac gga     864
Val Lys Lys Gly Asp Ser Thr Ile Met Lys Ser Glu Leu Glu Tyr Gly
        275                  280                  285 aac tgt aac acc aaa tgc cag acc cct atg ggc gct atc aac tct tct     912
Asn Cys Asn Thr Lys Cys Gln Thr Pro Met Gly Ala Ile Asn Ser Ser
    290                  295                  300 atg ccc ttc cac aac atc cac cct ctc act atc ggc gaa tgc cca aaa     960
Met Pro Phe His Asn Ile His Pro Leu Thr Ile Gly Glu Cys Pro Lys
305                  310                  315                  320 tac gtc aaa tca aac cgg ctc gtg ctg gct act ggg ctg aga aac tca    1008
Tyr Val Lys Ser Asn Arg Leu Val Leu Ala Thr Gly Leu Arg Asn Ser
                325                  330                  335 cct cag cga gag act aga ggc ctg ttt ggc gcc att gct gga ttc att    1056
Pro Gln Arg Glu Thr Arg Gly Leu Phe Gly Ala Ile Ala Gly Phe Ile
            340                  345                  350 gag gga ggc tgg cag gga atg gtc gat ggc tgg tac gga tac cat cac    1104
Glu Gly Gly Trp Gln Gly Met Val Asp Gly Trp Tyr Gly Tyr His His
        355                  360                  365 tcc aat gag cag gga tct gga tac gct gcc gat aag gag tcc acc cag    1152
Ser Asn Glu Gln Gly Ser Gly Tyr Ala Ala Asp Lys Glu Ser Thr Gln
```

-continued

```
                Ser Asn Glu Gln Gly Ser Gly Tyr Ala Ala Asp Lys Glu Ser Thr Gln
                    370                 375                 380 aaa gca atc gat ggc gtc acc aac aaa gtc aat tca atc atc gac aaa           1200
Lys Ala Ile Asp Gly Val Thr Asn Lys Val Asn Ser Ile Ile Asp Lys
385                 390                 395                 400 atg aac acc cag ttc gag gct gtg gga cga gag ttc aat aac ctg gag           1248
Met Asn Thr Gln Phe Glu Ala Val Gly Arg Glu Phe Asn Asn Leu Glu
                405                 410                 415 cgg aga atc gaa aac ctg aac aaa aaa atg gag gac ggc ttc ctc gat           1296
Arg Arg Ile Glu Asn Leu Asn Lys Lys Met Glu Asp Gly Phe Leu Asp
            420                 425                 430 gtg tgg acc tac aat gct gaa ctg ctg gtg ctc atg gaa aac gag aga           1344
Val Trp Thr Tyr Asn Ala Glu Leu Leu Val Leu Met Glu Asn Glu Arg
        435                 440                 445 acc ctg gac ttc cac gac tca aac gtg aaa aac ctg tac gac aaa gtc           1392
Thr Leu Asp Phe His Asp Ser Asn Val Lys Asn Leu Tyr Asp Lys Val
    450                 455                 460 cgg ctc cag ctg agg gat aat gcc aag gaa ctc gga aat ggc tgc ttc           1440
Arg Leu Gln Leu Arg Asp Asn Ala Lys Glu Leu Gly Asn Gly Cys Phe
465                 470                 475                 480 gag ttc tac cac aaa tgt gac aac gag tgt atg gag tct gtc cga aac           1488
Glu Phe Tyr His Lys Cys Asp Asn Glu Cys Met Glu Ser Val Arg Asn
                485                 490                 495 gga acc tac gac tac cct cag tac tct gag gag gct aga ctg aaa cga           1536
Gly Thr Tyr Asp Tyr Pro Gln Tyr Ser Glu Glu Ala Arg Leu Lys Arg
            500                 505                 510 gag gag atc tct ggc gtc aaa ctg gag tct atc gga atc tac cag att           1584
Glu Glu Ile Ser Gly Val Lys Leu Glu Ser Ile Gly Ile Tyr Gln Ile
        515                 520                 525 ctg tcc atc tac tct act gtg gct tct tca ctg gct ctg gcc atc atg           1632
Leu Ser Ile Tyr Ser Thr Val Ala Ser Ser Leu Ala Leu Ala Ile Met
    530                 535                 540 gtc gct ggg ctg tct ctg tgg atg tgc tca aat gga tca ctc cag tgc           1680
Val Ala Gly Leu Ser Leu Trp Met Cys Ser Asn Gly Ser Leu Gln Cys
545                 550                 555                 560 cgg atc tgt atc tag                                                       1695
Arg Ile Cys Ile
```

<210> SEQ ID NO 41
<211> LENGTH: 548
<212> TYPE: PRT
<213> ORGANISM: Avian influenza virus
<220> FEATURE:
<221> NAME/KEY: mat_peptide
<222> LOCATION: (1)..(548)

<400> SEQUENCE: 41

```
Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
                20                  25                  30

Leu Glu Lys Thr His Asn Gly Lys Leu Cys Asp Leu Asp Gly Val Lys
            35                  40                  45

Pro Leu Ile Leu Arg Asp Cys Ser Val Ala Gly Trp Leu Leu Gly Asn
        50                  55                  60

Pro Met Cys Asp Glu Phe Ile Asn Val Pro Glu Trp Ser Tyr Ile Val
65                  70                  75                  80

Glu Lys Asn Asn Thr Val Asn Asp Leu Cys Tyr Pro Gly Asp Phe Asn
                85                  90                  95
```

```
Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Asn Ser
        115                 120                 125

Ser Gly Val Ser Ser Ala Cys Pro Tyr Asn Gly Thr Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Ser
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
450                 455                 460

Glu Phe Tyr His Lys Cys Asp Asn Glu Cys Met Glu Ser Val Arg Asn
465                 470                 475                 480

Gly Thr Tyr Asp Tyr Pro Gln Tyr Ser Glu Glu Ala Arg Leu Lys Arg
                485                 490                 495

Glu Glu Ile Ser Gly Val Lys Leu Glu Ser Ile Gly Ile Tyr Gln Ile
            500                 505                 510

Leu Ser Ile Tyr Ser Thr Val Ala Ser Ser Leu Ala Leu Ala Ile Met
```

```
            515                 520                 525
Val Ala Gly Leu Ser Leu Trp Met Cys Ser Asn Gly Ser Leu Gln Cys
    530                 535                 540

Arg Ile Cys Ile
545
```

VACCINE AGAINST MULTITYPES OF AVIAN INFLUENZA VIRUSES AND USES THEREOF

CROSS-REFERENCES TO RELATED APPLICATIONS

The present application is a continuation-in-part application which claims priority to U.S. application Ser. No. 13/449,654, filed on Apr. 18, 2012, incorporated herein by reference in its entirety.

The sequence listing text file, file name 2267_NTHU_SQ, created Mar. 19, 2014, file size 254,952 bytes, is incorporated herein by reference in its entirety.

FIELD OF THE INVENTION

The present invention relates to a vaccine based on a mutant hemagglutinin protein derived from avian influenza virus, which can elicit an immune response against multiple avian influenza virus subtypes in a subject.

BACKGROUND OF THE INVENTION

Highly pathogenic avian influenza (HPAI) H5N1 viruses and their capacity for transmission from birds to humans have raised worldwide concerns about a potential forthcoming human pandemic. With the continued spread of H5N1 influenza virus, new virus strains have emerged and will continue to change and evolve in the future. The World Health Organization has classified the H5N1 viruses isolated recently into 10 clades (or sublineages) based on the phylogenetic analysis of viral hemagglutinin (HA) sequences of H5N1 viruses. With the continuous threat of a new influenza pandemic arising from avian reservoirs, the development of broadly protective vaccines is particularly important. To date, the broadly protective H5N1 vaccines have been mainly achieved using novel adjuvant formulations.

However, the inherent nature of influenza virus antigenic changes has not been taken into accounts in the immunogen designs for developing broadly protective H5N1 vaccines. Refocusing antibody responses have been proposed by designing the immunogens that can preserve the overall fold of the immunogen structure but selectively mutate the "undesired" antigenic sites that are highly variable (escape mutants evade protective immune responses), immunosuppressive (downregulate the immune response to the infection), cross-reactive (the immune response induces a reaction to a protein resembling the immunogen). The immunogen design by refocusing antibody responses has been applied for HIV-1 vaccines using the hyperglycosylated HIV-1 gp120 immunogens where the undesired eptiopes are masked by selective incorporations of N-linked glycans. The glycan masking strategy has been also recently reported to design influenza virus vaccines that can enhance the antibody responses against a broad range of H3N2 intertypic viruses. However, there is no report for the use of glycan-masking immunogen design for H5N1 vaccines.

DNA vaccine has been considered as the revolutionary vaccinology with the advantages in offering genetically antigen design, time to manufacturing, long stability without the need for cold chains supply, and the immunogenicity predominantly elicited by T cells through the endogenerous antigen processing pathways. However, the apparent low immunogenicity of DNA vaccines in large animals (including humans) has been overcome using novel delivery systems such as gene-guns or electroporation. Additionally, the DNA vaccine-elicited immune responses can be further augmented using the heterologous prime-boost immunization regimen where the booster dose uses a different vaccine format containing the same or similar antigens. Examples of DNA vaccine prime-boost immunization strategy has been reported for the inactivated influenza virus, live-attenuated influenza virus, recombinant adenovirus, virus-like particles (VLPs) and recombinant subunit proteins in adjuvants. Furthermore, human vaccines receiving the H5 DNA vaccine priming followed by a booster with inactivated H5N1 vaccine were found to enhance the protective antibody responses (HAI) and in some cases induce the haemagglutinin-stem-specific neutralizing antibodies.

Influenza VLPs are noninfectious and have a size and morphology that are similar to those of native virion structures, but they do not contain the genomic RNAs for virus replication. The assembly of influenza VLPs depends on the interactions of M1 proteins and/or other viral surface proteins, such as HA, NA, and M2, with the cellular lipid membranes. The interactions of M1 protein with the cytoplasmic tails of HA and NA spikes can increase the lipid membrane binding of M1 proteins in assembling influenza virus. The interactions of HA and NA with the M1 protein can also reduce the formation of elongated intracellular immature particles and improve the secretion of spherical mature VLPs. Additionally, the cytoplasmic tails of M2 protein, by interacting with the M1 protein, further promote the budding and release of the influenza virions. Recently, the M2 protein was found to act as the plasma membrane-targeting signal for the budding and egress of influenza virions. Host cell proteins can be recruited into the VLPs, as recently shown by LC/MS/MS analyses. Therefore, the biosynthesis of influenza VLPs is a self-assembly process that involves complex interactions of viral and cellular components.

There is a clear need for a broadly protective H5N1 vaccine or vaccines for inducing neutralizing antibodies against multiple clades/subclades.

BRIEF DESCRIPTION OF THE DRAWINGS

The invention can be more fully understood by reading the subsequent detailed descriptions and examples with references made to the accompanying drawing, wherein:

FIG. 24 shows HI titers elicited by glycan-masked H5HA mutant antigens. Sera were serially diluted and incubated with 4 HA units H5N1pp containing HA from KAN-1 (clade 1), Indonesia (clade 2.1), Qinghai (clade 2.2), or Anhui (clade 2.3.4). HI titer was measured as the reciprocal of the highest dilution of sera which completely inhibiting hemagglutination. Data represent geometric mean±standard deviation. Results were analyzed using one-way ANOVAs and Tukey's tests (*, statistical significance at $p<0.05$).

FIG. 25 shows neutralizing antibody titers elicited by glycan-masked H5HA mutant antigens. Serum dilution neutralization curves were obtained using H5 pp containing HA from (A) KAN-1 (clade 1), (B) Indonesia (clade 2.1), (C) Qinghai (clade 2.2), or (D) Anhui (clade 2.3.4) strains.

FIG. 26 shows that neutralization titers are shown as IC50 values calculated from neutralization curves for H5 pp containing HA from KAN-1 (clade 1), Indonesia (clade 2.1), Qinghai (clade 2.2), or Anhui (clade 2.3.4) strains.

FIG. 29 shows mapping of stem-specific antibodies elicited by glycan-masked H5HA mutants. Sera were pre-absorbed with (A) ΔStem-H5HA. ELISAs were performed to measure HA-specific IgG titers of pre-absorbed sera against different HAs. Antibody competition assays were performed using (B) mAb CR6261 and (C) mAb FI6v3. Percentages of mAb competition to block binding between pre-absorbed sera and different H5HA proteins were calculated. Data represent geometric mean±standard deviation. Results were analyzed using one-way ANOVAs and Tukey's tests (*, statistical significance at $p<0.05$).

FIG. 30 shows protective immunity against influenza viruses challenges. The immunized mice were intranasally challenged with the reassortant RG2 (clade 2.1) or NIBRG23 (clade 2.2). After virus challenge, survival and body weight were recorded for 14 days. The body weight of each immunized group is presented as mean±standard deviation. Over 25% body weight loss is regarded as an end-point.

SUMMARY OF THE INVENTION

Figure 1:
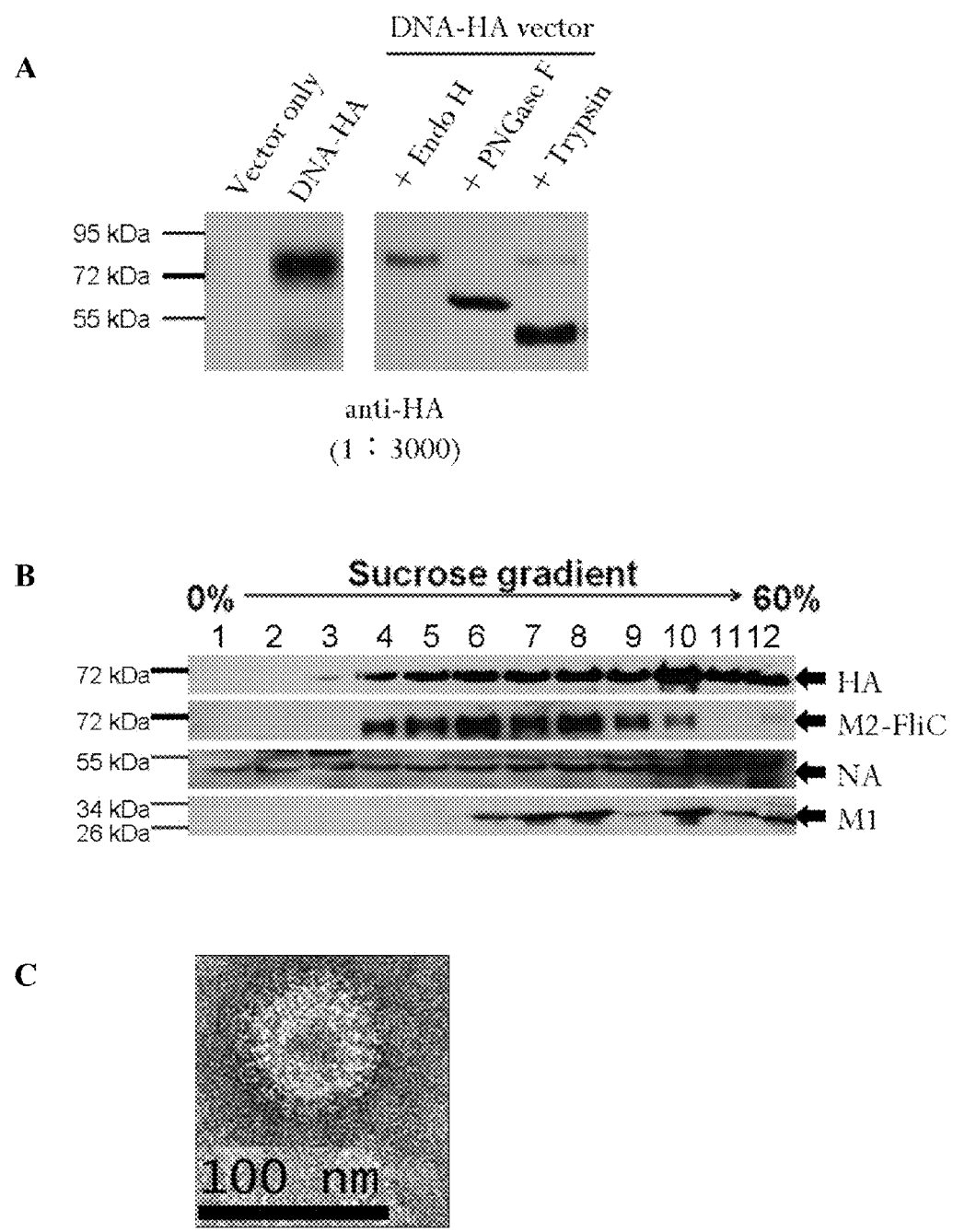
FIG. 1 shows expression and characterization of DNA-HA and FliC-VLP. (A) The cell lysates of 293A cells transfected with either DNA-HA or empty vector were treated with Endo H, PNGase F and Trypsin, and analyzed by Western blots. Full-length HA proteins showed the presence of a molecular weight of approximately 75 kDa and HA1 proteins showed the presence of a molecular weight of about 46 kDa. (B) FliC-VLPs were purified by sucrose gradient sedimentation and the results showed the fractions 6 to 10 from the sucrose density gradient contained all four proteins. (C) Electron microscopic visualization demonstrated the spherical morphology of the FliC-VLPs with a particle size around 100 nm.

The present invention relates to a recombinant DNA molecule encoding a mutated hemagglutinin protein, wherein the mutated hemagglutinin protein consists of the amino acid sequence of SEQ ID NO: 2 with one or more mutations at amino acid residue selecting from the group consisting of residue 83, 127, 138 and the combination thereof. The present invention also relates to a composition comprising the recombinant DNA molecule as described above and a pharmaceutically or veterinarily acceptable carrier, excipient, adjuvant, or vehicle. The present invention further relates to a kit for prime-boost vaccination, comprising at least a composition comprising a recombinant DNA molecule as described above and at least a composition for the boost-vaccination comprising a recombinant hemagglutiinin protein or a virus-like particle, wherein the recombinant hemagglutiinin protein is the corresponding hemagglutiinin protein encoded by the recombinant DNA molecule. The present invention still further relates to a method of vaccinating a subject susceptible to avian influenza comprising administrating to the subject an effective amount of the composition as described above. The present invention still further relates to a recombinant hemagglutinin protein consisting of the amino acid sequence of SEQ ID NO: 2 with one or more mutations at amino acid residue selecting from the group consisting of residue 83, 127, 138, and the combination thereof.

DETAILED DESCRIPTION OF THE INVENTION

U.S. application Ser. No. 13/449,654, filed on Apr. 18, 2012, has reported that N-linked glycan masking in highly variable sequences in the HA1 globular head in residues 83 and 127 resulted in increased cross-neutralizing antibody titers. The goal in the present invention is to use adenovirus vector prime and recombinant hemagglutiinin protein booster regimens to further investigate cross-clade immunity elicited by single or multiple glycan-masked HAs. Hence, the present invention constructs single, double, and triple mutants of glycan-masked hemagglutiinin (HA) antigens at residues 83, 127 and 138 (i.e. g83, g127, g138, g83+, g127, g127+g138, g83+g138 and g83+g127+g138), and then obtains their corresponding HA-expressing adenovirus vectors and recombinant HA proteins using a prime-boost immunization strategy. The results indicate that multiple glycan-masked HA elicits the highest titer of cross-clade hemagglutination inhibition (HI) and neutralizing antibodies with enhanced binding to receptor binding sites (RBS) and the stem region. The results also indicate that the immunization strategy by priming with the adenovirus vector followed by a recombinant H5HA protein booster elicits approximately one-log increased HI titers and 0.3- to 0.4-log increased neutralizing antibody titers, as compared to the immunization strategy using two-dose DNA priming, followed by virus-like particles (VLPs) booster. These results indicate that single-dose adenovirus vector can outcompete two-dose DNA vector in priming the immune responses by immunization. It is also found that the booster with recombinant H5HA protein in PELC/CpG adjuvant is as effective as the booster with flagellin-adjuvanted VLPs to improve anti-influenza immunity. These findings provide useful information in the development of a broadly protective H5N1 influenza vaccine.

As used herein, the term "wild-type" refers to a naturally occurring organism. The term also relates to nucleic acids and proteins found in a naturally occurring organism of a naturally occurring population arising from natural processes, such as seen in polymorphisms arising from natural mutation and maintained by genetic drift, natural selection and so on, and does not include a nucleic acid or protein with a sequence obtained by, for example, recombinant means.

"Immunogen" and "antigen" are used interchangeably herein as a molecule that elicits a specific immune response of antibody (humoral-mediated) and/or T cell origin (cell-mediated), for example, containing an antibody that binds to that molecule or a $CD4^+$ or $CD8^+$ T cell that recognizes a virally-infected cell expressing that molecule. That molecule can contain one or more sites to which a specific antibody or T cell binds. As known in the art, such sites are known as epitopes or determinants. An antigen can be polypeptide, polynucleotide, polysaccharide, a lipid and so on, as well as a combination thereof, such as a glycoprotein or a lipoprotein. An immunogenic compound or product, or an antigenic compound or product is one which elicits a specific immune response, which can be humoral, cellular or both.

An "individual" or "subject" or "animal", as used herein, refers to vertebrates that support a negative strand RNA virus infection, specifically influenza virus infection, including, but not limited to, birds (such as water fowl and chickens) and members of the mammalian species, such as canine, feline, lupine, mustela, rodent (racine, and murine, etc.), equine, bovine, ovine, caprine, porcine species, and primates, the latter including humans.

As used herein, the term "a plurality of" is employed to describe the number of elements and components of the present invention. This description should be read to more than one unless it is obvious that it is meant otherwise.

As used herein, the term "a" or "an" is employed to describe elements and components of the invention. This is done merely for convenience and to give a general sense of the invention. This description should be read to include one or at least one and the singular also includes the plural unless it is obvious that it is meant otherwise.

As used herein, the term "or" is employed to describe "and/or".

Accordingly, the present invention provides a recombinant DNA molecule encoding a mutated hemagglutinin protein, wherein the mutated hemagglutinin protein consists of the amino acid sequence of SEQ ID NO: 2 with one or more mutations at amino acid residue selecting from the group consisting of residue 83, 127, 138 and the combination thereof. In an embodiment, the mutated hemagglutinin protein consists of the amino acid sequence of SEQ ID NO: 4, 10, 33, 35, 37, 39 or 41. In a further embodiment, the mutated hemagglutinin protein consists of the amino acid sequence of SEQ ID NO: 37 or SEQ ID NO: 41.

The present invention also provides a composition comprising the recombinant DNA molecule as described above and a pharmaceutically or veterinarily acceptable carrier, excipient, adjuvant, or vehicle. In an embodiment, the composition has the activity of eliciting an immune response against a plurality of avian influenza virus subtypes in a subject.

The present invention further provides a kit for prime-boost vaccination, comprising at least a composition comprising a recombinant DNA molecule as described above and at least a composition for the boost-vaccination comprising a recombinant hemagglutiinin protein or a virus-like particle, wherein the recombinant hemagglutiinin protein is the corresponding hemagglutiinin protein encoded by the recombinant DNA molecule. In an embodiment, the recombinant hemagglutiinin protein consists of the amino acid sequence of SEQ ID NO: 4, 10, 33, 35, 37, 39 or 41.

The present invention still further provides a method of vaccinating a subject susceptible to avian influenza comprising administrating to the subject an effective amount of the composition as described above. In an embodiment, the method comprises a prime-boost administration regimen. In a further embodiment, the prime-boost administration regimen comprises a prime-administration of a composition as described above. In a further embodiment, the prime-boost administration regimen comprises a boost administration of a composition as described above. In a still further embodiment, the prime-boost administration regimen comprises a prime-administration of a composition as described above and a boost administration of a composition comprising a recombinant hemagglutiinin protein or a virus-like particle, wherein the recombinant hemagglutiinin protein is the corresponding hemagglutiinin protein encoded by the recombinant DNA molecule. The recombinant hemagglutiinin protein preferably is the amino acid sequence of SEQ ID NO: 4, 10, 33, 35, 37, 39 or 41. In an embodiment, the above method elicits an immune response against multiple avian influenza virus subtypes in the subject.

The present invention still further provides a recombinant hemagglutinin protein consisting of the amino acid sequence of SEQ ID NO: 2 with one or more mutations at amino acid residue selecting from the group consisting of residue 83, 127, 138, and the combination thereof. In an embodiment, the recombinant hemagglutinin protein consists of the amino acid sequence of SEQ ID NO: 4, 10, 33, 35, 37, 39 or 41. In a further embodiment, the mutated hemagglutinin protein consists of the amino acid sequence of SEQ ID NO: 37 or SEQ ID NO: 41.

The next examples provide some exemplary embodiments of the present invention as follows:

EXAMPLES

The examples below are non-limiting and are merely representative of various aspects and features of the present invention.

Example 1

Material and Methods
Construction of DNA-HA Vaccine Vector

The cDNA of the HA gene of influenza virus A/Thailand/1(KAN-1)/2004/H5N1 (clade 1), SEQ ID NO: 1, was provided by Prasert Auewarakul, Siriraj Hospital, Thailand. The full-length HA sequence was inserted into a pcDNA™3.1(+) vector (Invitrogen) using KpnI/NotI cut site. The constructed plasmid containing H5HA was transfected into 293A cells by using Turbofect reagent (Fermentas). Following transfection for 48 hours, the cell lysates were collected by centrifugation at 5000 rpm for 10 minutes and HA expression was analyzed by Western blotting with anti-H5HA antibodies (ab21297; Abcam).

HA Glycosylation Pattern and Trypsin Treatment

For characterizing the HA glycosylation pattern, 293A cells were harvested after transfected with DNA-HA vectors for 48 hours. The cell lysates were treated with EndoH or PNGase F for 2 hours at 37° C., and the H5HA glycosylation pattern was determined by Western blotting. For trypsin treatment, the cell lysates were incubated with trypsin for 30 minutes on ice, and the cleavage of HA0 into HA1 and HA2 was observed by Western blotting.

Preparation of VLPs

VLPs were prepared as described previously (Wei H J et al., Vaccine 29 (2011): 7163-7172). Briefly, HA (SEQ ID NO: 1) and M1 (SEQ ID NO: 21) were cloned into a pFastBac™ Dual vector (Invitrogen), while NA (SEQ ID NO: 27) and FliC-M2 (SEQ ID NO: 25), expressing FliC-M2 fusion proteins, were cloned into the other one to produce the recombinant baculoviruses. Sf9 cells co-infected with recombinant baculoviruses were harvested at 72 hours post-infection, and supernatants containing FliC-VLPs were concentrated by filtration with a 500 kDa filter membrane. The concentrate were loaded on 0-60% sucrose gradients and centrifuged for 4 hours at 33,000 rpm. The desired particles were observed by Western blotting using anti-H5HA antibodies (ab21297; Abcam), anti-NA antibodies (ab70759; Abcam), anti-M1 antibodies (ab25918; Abcam), and anti-M2 antibodies (NB100-2073; Novus). The particles were also confirmed by transmission electron microscopy (TEM) as described previously (Wei H J et al., Vaccine 29 (2011): 7163-7172).

Preparation of Hyperglycosylated H5HA

Mutations were introduced into the HA gene by using the site-directed mutagenesis, and plasmids encoding wild-type H5HA gene (SEQ ID NO: 1) were used as templates. The 50 µL PCR reaction was carried out with 100 ng templates, 2 mM primer pair, 200 mM dNTPs and 2U of DNA polymerase. The PCR products were purified and further treated with DpnI for 2 hours at 37° C. DpnI treated products were transformed into TOP10 competent cell and then the mutated plasmids were isolated.

Hemadsorption Assay 293A cells were transfected with wild-type and mutated H5HA DNA vectors, and the cells were harvested at 72 hours post infection. Following phosphate-buffered saline (PBS) wash, sufficient 0.5% turkey red blood cells (RBCs) were added to cover cell monolayer and incubate for 30 minutes. Adsorption of RBCs on the transfected cells was observed after rinse with PBS two times.

Mouse Immunization 6 to 8 weeks old female BALB/c mice were immunized with heterologous prime-boost strategy by 50 μg of DNA and 30 μg of purified VLPs mixed with Alum adjuvant in PBS. Immunizations were performed at weeks 0, 3 by intramuscular injection. Blood was collected at 14 days following immunization, and serum was isolated. Serum samples were inactivated at 56° C. for 30 minutes and stored in −20° C. All experiments were conducted in accordance with the guidelines of the Laboratory Animal Center of National Tsing Hua University (NTHU). Animal use protocols were reviewed and approved by the NTHU Institutional Animal Care and Use Committee (approval no. 09733).

Enzyme-linked Immunosorbent (ELISA) Assay

ELISA assay was performed as described previously (Lin S C et al., PLoS_One 6 (2011): e20052). Briefly, 2 μg/mL of purified protein were coated on 96 well plates and then blocked with BSA. Serial dilutions of each serum sample were incubated in the plates for 1 hour and removed by 3 times wash. Goat anti-mouse IgG conjugated HRP (Bethyl Laboratories, Inc.) was incubated in the plates for 1 hour followed by 3 times wash. After the reaction with TMB substrate stop, plates were read at 450 nm absorbance. End-point titer was determined as the reciprocal of the final dilution giving an optical of two-fold absorbance of negative control.

Hemagglutinin Inhibition (HI) and Neutralization (NT) Assays

HI and NT assays were performed as described previously (Huang M H et al., PLoS One 5 (2010): e12279). For HI assay, serum samples (two-fold dilutions starting with an initial dilution of 1:10) were incubated with four HA units of influenza strain. Turkey RBCs were then added and the inhibition of agglutination was scored. The serum titer was expressed as the reciprocal of the highest dilution that showed complete inhibition of HA. For NT assay, the 200 $TCID_{50}$ per well of virus were incubated with two-fold-diluted mice sera at a starting dilution of 1:40. Mixtures of virus and serum were transferred to monolayers of MDCK cells and incubated for 4 days. The neutralizing titer was defined as the reciprocal of the highest serum dilution at which the infectivity of the H5N1 virus was neutralized in 50% of the wells. Infectivity was identified by the presence of cytopathy on Day 4 and the titer was calculated using the Reed-Muench method.

Statistic Analysis

All results were analyzed using two-tailed Student's t tests, with a P value of <0.05 indicating statistical significance Results Construction and Characterization of DNA-HA Vaccine Vector and FliC-VLPs for Prime-boost Immunization The DNA vaccine vector (DNA-HA) encoding the full-length cDNA of the A/Thailand/1(KAN-1)/2004/H5N1 (clade 1) HA gene (SEQ ID NO: 1) was constructed from the pcDNA™3.1(+) vector. Expression of the full-length HA protein was demonstrated in 293A cells transfected with the DNA-HA vector and analyzed in Western blots to show the presence of a molecular weight of approximately 75 kDa (FIG. 1A). The expressed HA in 293A cells was sensitive to PNGase F treatment but resistant to EndoH digestion, suggesting as a glycoprotein containing complex type N-linked glycan profiling (FIG. 1A). The expressed HA in DNA-HA transfected 293A cells was also sensitive to trypsin treatment by cleavage from HA0 to HA1 and HA2 subunits, as shown the presence of HA1 at a molecular weight about 46 kDa (FIG. 1A).

The FliC-containing VLPs (FliC-VLPs) were obtained from Sf9 cells infected with two recombinant baculoviruses encoding four of the influenza virus genes of HA, NA, and M1, and the fusion of M2 and the Samollena fliC genes (Wei H J et al., Vaccine 29 (2011): 7163-7172). FliC-VLPs were obtained from the culture supernatants of baculovirus-infected Sf9 cells, purified by ultracentrifugation and sucrose gradient sedimentation. The results show the fractions 6 to 10 from the sucrose density gradient contained all four viral or fusion proteins (FIG. 1B). Electron microscopic visualization demonstrated the spherical morphology of the FliC-VLPs with a particle size around 100 nm (FIG. 1C).

Figure 2:
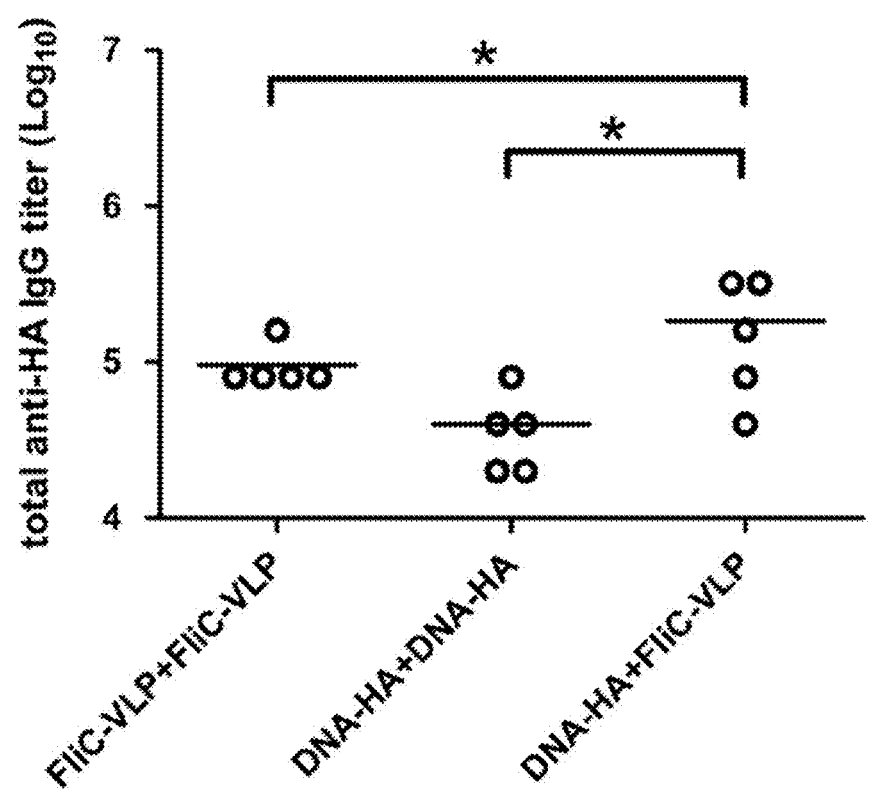
FIG. 2 shows total anti-HA IgG titers elicited by DNA-HA and FliC-VLP. Asterisks indicate a statistically significant difference ($p<0.05$).
Figure 3:
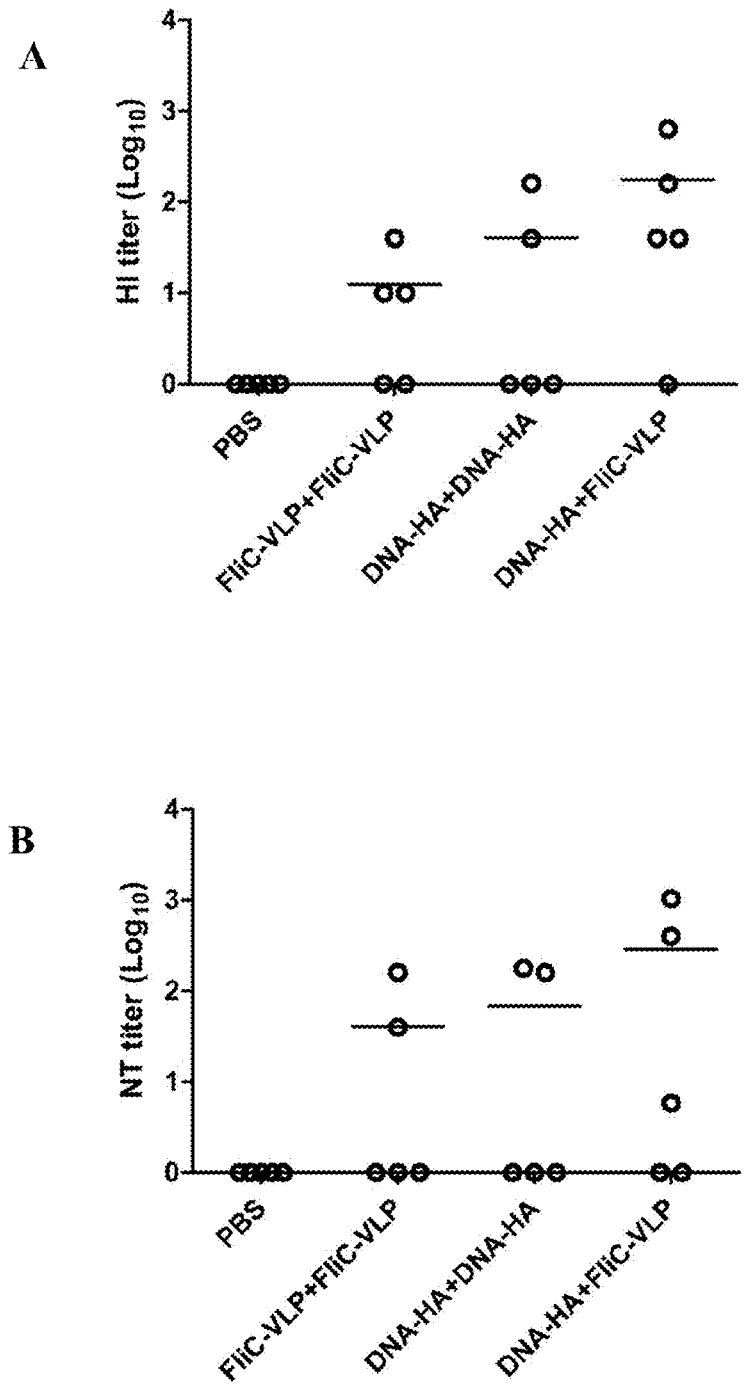
FIG. 3 shows neutralizing activities of the sera from immunized mice by the (A) HI and (B) NT titers against the NIBRG-14 (clade 1) H5N1 influenza virus. For calculation purposes, an undetectable level was scored as a titer equal to one. Individual titer (points) and geomean (lines) was given for each group.

To investigate the combined use of DNA-HA vaccine vector and FliC-VLP for prime-boost immunization studies, BALB/c mice were immunized intramuscularly (i.m) for two doses within a three-week interval as the following prime-boost regimens: (i) PBS+PBS (ii) FliC-VLP+FliC-VLP (iii) DNA-HA+DNA-HA (iv) DNA-HA+FliC-VLP. Sera were collected at two weeks after the second dose in immunized mice. The results show that the HA-specific total IgG titer by DNA-HA vaccine vector priming, followed by FliC-VLP boosting was significantly higher than two-dose immunization using DNA-HA vector and FliC-VLPs (FIG. 2). Neutralizing activities revealed by measuring the HI and NT titers against the NIBRG-14 (clade 1) H5N1 influenza virus show that the DNA-HA vector priming and FliC-VLP boosting regiment elicited the highest magnitude of neutralizing antibodies in mice (FIGS. 3A-B).

Figure 4:
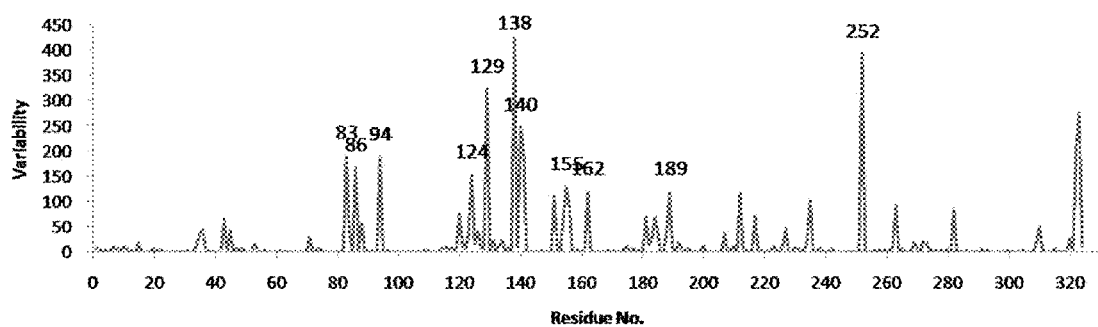
FIG. 4 shows analytical result of amino acid variation in the HA of 163 avian influenza virus strains. Eleven amino acids in the HA1 subunit, including the 83, 86, 94, 124, 129, 138, 140, 155, 162, 189 and 252 residues were calculated to have relatively higher scoring numbers.
Figure 5:
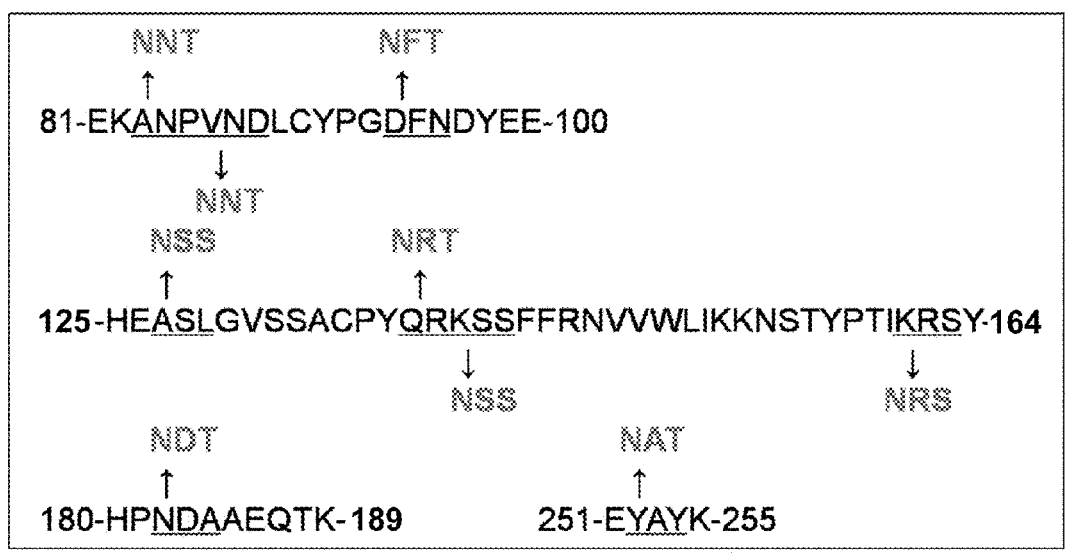
FIG. 5 shows nine N-linked glycosylation sites: 83NNT (SEQ ID NO:4), 86NNT (SEQ ID NO:6), 94NFT (SEQ ID NO:8), 127NSS (SEQ ID NO:10), 138NRT (SEQ ID NO:12), 140NSS (SEQ ID NO:14), 161NRS (SEQ ID NO:16), 182NDT (SEQ ID NO:18), and 252NAT (SEQ ID NO:20). Underlined triplet amino acids and arrows point away from wild-type sequence to amino acid change that resulted in N-linked glycosylation sequence.
Figure 6:
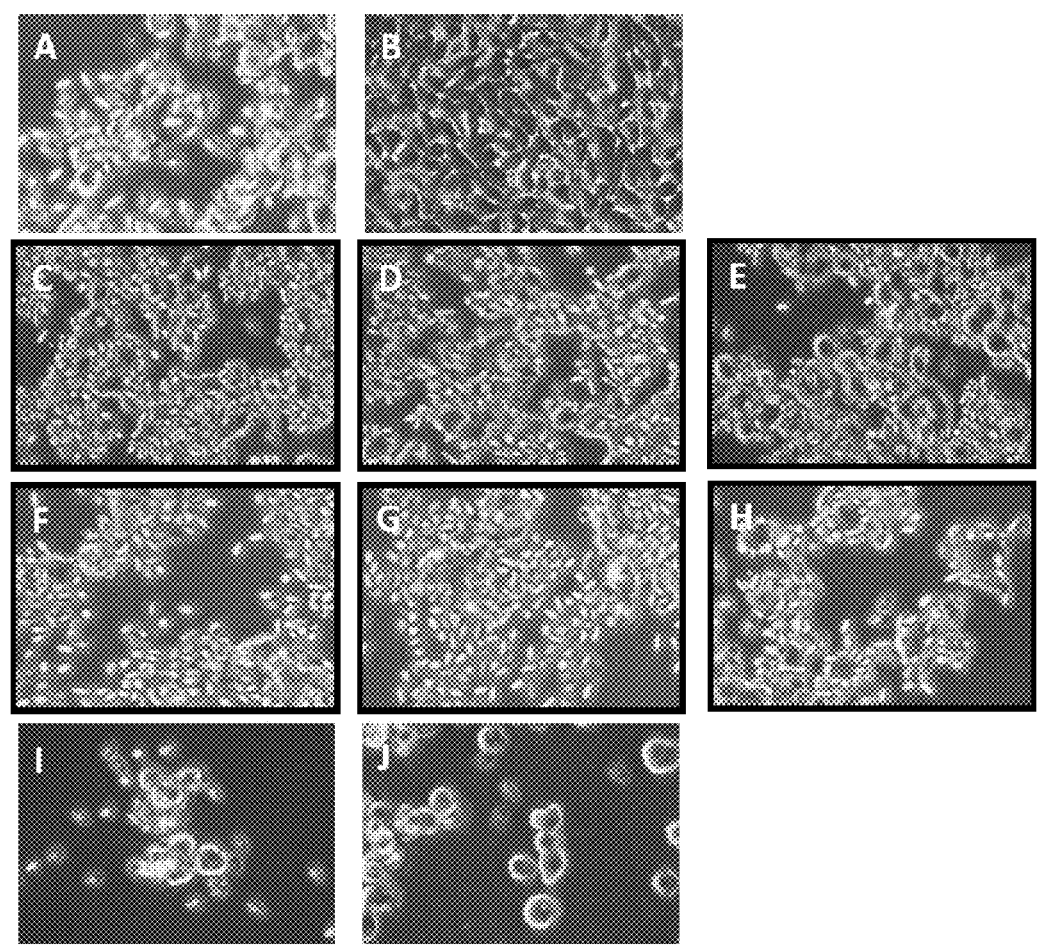
FIG. 6 shows the results of hemadsorption assay. (A) Positive control; (B) negative control; (C) 83NNT; (D) 86NNT; (E) 94NFT; (F) 127NSS; (G) 138NRT; (H) 161NRS; (I) 182NDT; and (J) 252NAT.
Figure 7:
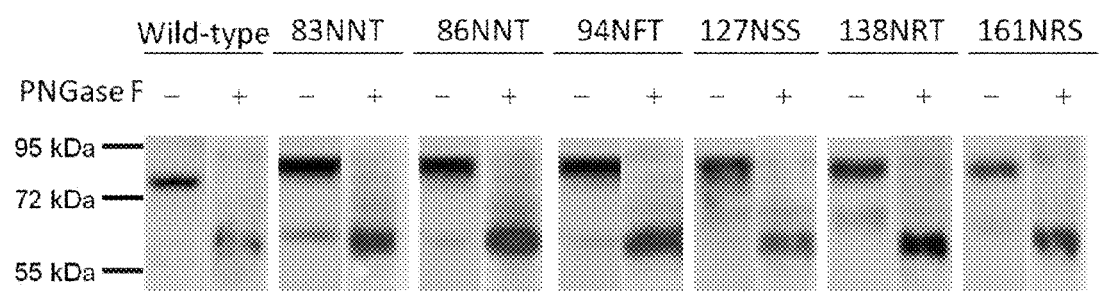
FIG. 7 shows characterization of hyperglycosylated HA. The six HA mutant proteins (83NNT, 86NNT, 94NFT, 127NSS, 138NRT, 161NRS) with N-linked glycans addition were illustrated by the increased molecular weights and reduced to the same molecular weight after PNGase F treatment.

Design of Hyperglycosylated HA Based on Amino Acid Sequences of H5N1 Human Isolates To design the hyperglycosyalted HA DNA vaccines, sequence alignment analysis was first conducted from 163 HPAI H5N1 human isolates (sequences retrieved from NCBI Database). The amino acid differences in these HA1 protein sequences were analyzed based on the following scoring numbers, 4 (different amino acid), 2 (weak similar amino acid), 1 (strong similar amino acid), 0 (identical amino acid) as characterized by the Vector NTI Similar Tables. According to the alignment plot shown in FIG. 4, eleven amino acid residues in the HA1 protein were identified to have a relatively higher scoring numbers, including the 83, 86, 94, 124, 129, 138, 140, 155, 162, 189, and 252 residue. To design the antibody-refocused immunogens, site-directed mutagenesis is conducted in each of the five regions with mutations to allow the addition of the N-X-S/T motif (for N-linked glycosylation site) but avoid the receptor binding sites (Yang Z Y et al., Science 317 (2007): 825-828; and Yang H et al., PLoS Pathog 6 (2010): e1001081). Nine N-X-S/T motifs were thus introduced into HA1, including 83NNT (SEQ ID NO: 4), 86NNT (SEQ ID NO: 6), 94NFT (SEQ ID NO: 8), 127NSS (SEQ ID NO: 10), 138NRT (SEQ ID NO: 12), 140NSS (SEQ ID NO:14), 161NRS (SEQ ID NO: 16), 182NDT (SEQ ID NO: 18), and 252 NAT (SEQ ID NO: 20) (FIG. 5). Each of the refocusing hyperglycosylated HA genes containing the specified N-linked glycosylation sites were cloned into the DNA-HA vaccine vector. However, only six out the nine immuno focusing HA retained the hemagglutination property for Turkey red blood cells after transfection into 293A cells (FIG. 6). The six HA mutant genes (83NNT, 86NNT, 94NFT, 127NSS, 138NRT and 161NRS) were also investigated for the introduction of N-linked glycans in the HA antigens as illustrated by the increased molecular weights and reduced to the same molecular weight after PNGase F treatment (FIG. 7).

Priming with Hyperglycosylated HA DNA Vaccines Followed by FliC-VLP Boosting

Figure 8:
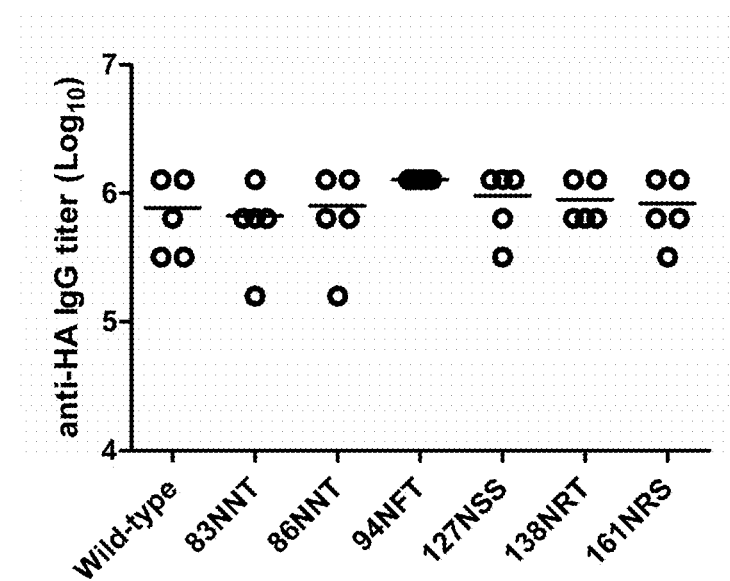
FIG. 8 shows total anti-HA IgG titers elicited by hyperglycosylated HA. Individual titer (points) and geomean (lines) was given for each group.
Figure 9:
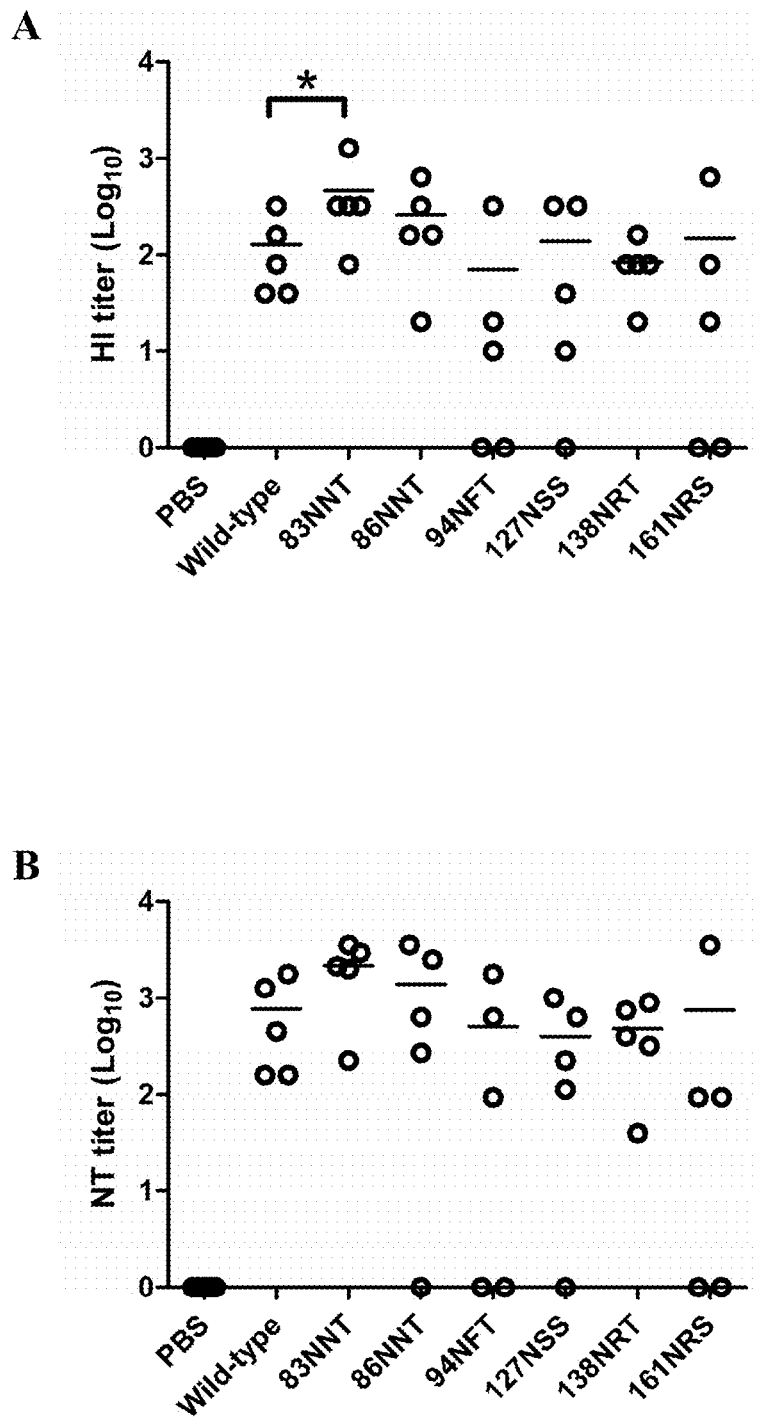
FIG. 9 shows neutralizing activities of sera from immunized mice by the (A) HI and (B) NT titers against the NIBRG-14 (clade 1) H5N1 influenza virus. For calculation purposes, an undetectable level was scored as a titer equal to one. Individual titer (points) and geomean (lines) was given for each group. Asterisks indicate a statistically significant difference ($p<0.05$).
Figure 10:
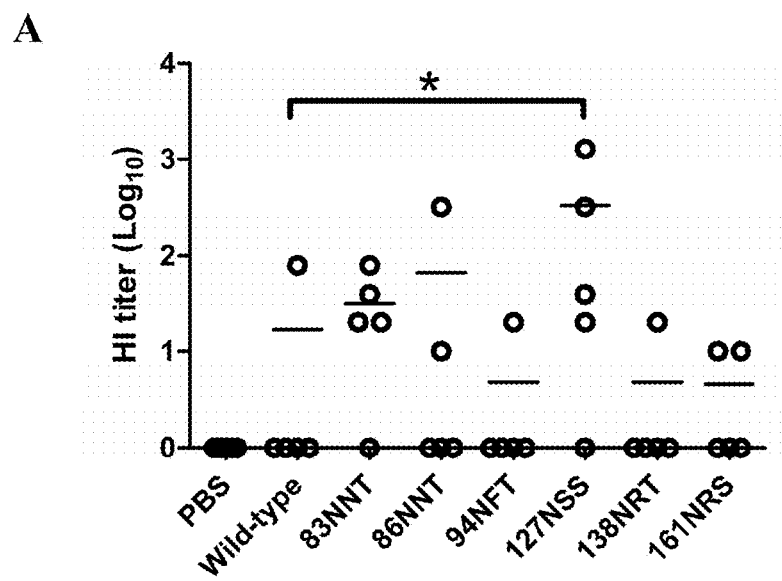
FIG. 10 shows neutralizing activities of sera from immunized mice by the (A) HI and (B) NT titers against the Mongolia/2/2006 (clade 2.2) H5N1 influenza virus. For calculation purposes, an undetectable level was scored as a titer equal to one. Individual titer (points) and geomean (lines) was given for each group. Asterisks indicate a statistically significant difference ($p<0.05$).
Figure 10:
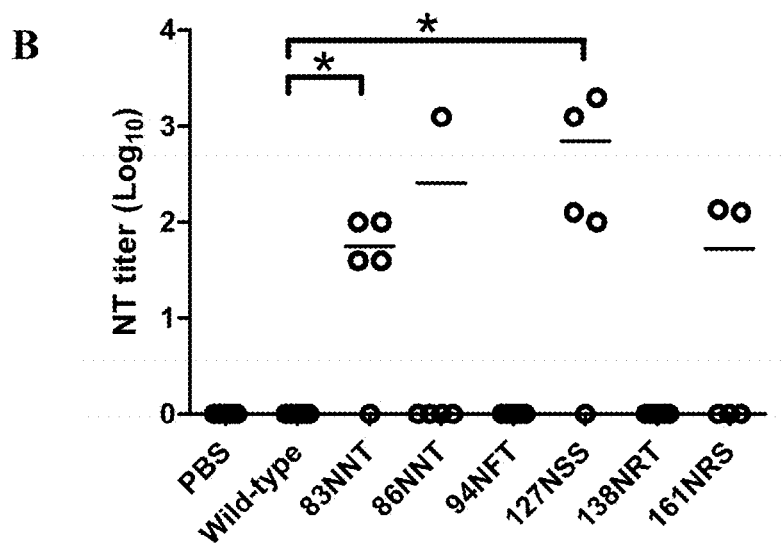

To investigate the antibody responses elicited by these six hyperglycosylated HA mutants (83NNT, 86NNT, 94NFT, 127NSS, 138NRT and 161NRS), mice were immunized with each DNA-HA vector twice followed with a third boosting dose with FliC-VLPs on a three-week interval. The results show that no significant differences of the HA-specific total IgG titers of all the immunized groups with the hyperglycosyalted HA DNA vaccines compared to the wild-type control (FIG. 8). The 83NNT and 86NNT HA mutants elicited higher HI titers (FIG. 9A) but only the 83NNT HA mutant had higher NT titer (FIG. 9B) against the NIBRG-14 virus that belongs to the same H5N1 clade 1 strain. The HI and NT titers of these sera against the Mongolia/2/2006 H5N1 virus of the clade 2.2 strain were also measured. The data presenting as cross-Glade functional antibodies show that the 83NNT, 86NNT, 127NSS HA mutants elicited higher HI titers (FIG. 10A) and the 83NNT, 86NNT, 127NSS, 161 NRS HA mutants had higher NT titers (FIG. 10B). Taken together, the 83NNT mutant can elicit more potent HI and NT titers against both the NIBRG-14 (clade 1) and Mongolia/2/2006 (clade 2.2) HPAI H5N1 viruses.

Example 2

Methods and Materials
Cell Lines

Sf9 cells (ATCC CRL-1711) (Invitrogen) were derived from pupal ovarian tissue of the fall armyworm, *Spodoptera frugiperda*. Sf9 cells were maintained in T-flasks at 28° C. with SF-900II serum free medium (GIBCO) that contained 100 units/mL penicillin and 100 µg/mL streptomycin (Invitrogen). For suspension cultures, Sf9 cells were inoculated in 500 mL spinner flasks (Belleco) at 60 rpm at 27° C. with 300 mL of the same medium. A549 cells (human lung carcinoma cells) (ATCC CCL-185) were maintained in T-flasks at 37° C. with DMEM (GIBCO) that contained 5% fetal bovine serum (FBS), 100 units/mL penicillin, and 100 µg/mL streptomycin (Invitrogen).

Mouse Bone Marrow-derived DCs

C57BL/6 mice were used at 10-14 weeks of age and their bone marrow cells were isolated from femurs and tibias and seeded on Costar 24-well cell culture plates in 1 mL of RPMI 1640 medium that was also supplemented with 10% heat-inactivated FBS, 2 mM l-glutamine, nonessential amino acids, sodium pyruvate, HEPES (all from GIBCO), $5.5 \times 10^{-2}$ M 2-ME (Sigma-Aldrich), 100 units/mL penicillin, 100 µg/mL streptomycin (Invitrogen) and 15 ng/mL recombinant mouse GM-CSF (PeproTech). On Day 3, 1 mL of medium that contained 10 ng/mL of GM-CSF was added to plates. On Day 5, another 0.5 mL fresh medium that contained 10 ng/mL of GM-CSF was added. The 6- to 7-day-culture BMDCs (>80% CD11c+ cells) were used. All experiments were conducted in accordance with the guidelines of Laboratory Animal Center of National Tsing Hua University (NTHU). The animal use protocols have been reviewed and approved by the NTHU Institutional Animal Care and Use Committee (Approved protocol no. 09733).

Plasmid Construction

The HA gene of A/Thailand/1(KAN-1)/2004/H5N1 (SEQ ID NO: 1) was provided by Dr. Prasert Auewarakul, Siriraj Hospital, Mahidol University, Thailand. The NA gene of A/Viet Nam/1203/2004/H5N1 (SEQ ID NO: 27) was obtained from Academia Sinica, Taiwan. The M1 (SEQ ID NO: 21) and M2 (SEQ ID NO: 23) genes of A/WSN/33/H1N1 were obtained from virus stocks using reverse transcription-PCR. The genes of HA (A/Anhui/1/2005/H5N1), enhanced florescence protein (EGFP), flagellin (FliC), and profilin (PRO) were purchased from synthesized sequences (Mr. Gene) based on the NCBI GenBank accession numbers GU983383.1, AY649721.1 and AY937257.1, respectively. Each gene fragment was subcloned into pFastbac Dual (Invitrogen) using BamHI/NotI site for HA, XhoI/KpnI site for M1, EcoRI/HindIII site for M2, XhoI/KpnI site for NA, EcoRI/HindIII site for EGFP/M2 fusion, EcoRI/HindIII site for FliC/M2 fusion, and EcoRI/HindIII site for PRO/M2 fusion. These inserted vectors were then transformed into *E. coli* strain DH5α and selected by ampicillin. All the inserted sequences were confirmed by DNA sequence analysis (Mission Biotech Inc., Taipei, Taiwan).

Generation of Recombinant Baculoviruses

The pFastbac Dual plasmids encoding each specified gene(s) were transformed into *E. coli* strain DH10Bac (Invitrogen) and selected on an LB plate that contained kanamycin (Invitrogen) gentamicin (Invitrogen), tetracycline (Invitrogen), Bluo-gal (Invitrogen), and IPTG (BioRad). The selected colonies or the recombinant bacmids were confirmed by PCR using M13 primers, then transfected into Sf9 cells using Cellfectin (Invitrogen). After 4 days, the recombinant baculoviruses were collected from culture supernatants and the virus titers were determined using an ID50 software.

Production and Purification of Influenza VLPs

The VLPs that were expressed by two viral proteins and Sf9 cells were infected with BacHA-M1 recombinant baculovirus at an MOI of 1. The VLPs that were expressed by three viral proteins were co-infected with BacHA-M1 and Bac-NA recombinant baculoviruses at an MOI of 3 and 1, respectively. The VLPs that were expressed by four viral proteins including M2 fusion proteins were co-infected with BacHA-M1 and BacM2-NA (or BacEGFP/M2-NA, BacNA-M2/FliC, BacNA-M2/PRO) recombinant baculoviruses at an MOI of 3 and 1, respectively. At 72 hours post infection, the culture supernatants were harvested and clarified by centrifugation for 0.5 hour at 12,000 rpm at 4° C. Then, they were concentrated and pelleted for 2 hours at 33,000 rpm and 4° C. using a Hitachi RPS40ST rotor. The particles were resuspended in 0.8 mL of PBS buffer, and loaded on a 0-60% (w/v) discontinuous sucrose gradient, before being ultracentrifuged by a Hitachi RPS40ST rotor 4 hours at 33,000 rpm and 4° C. Following ultracentrifugation, the fractions (0.8 mL) were collected and the samples in each fraction were analyzed by SDS-PAGE and Western blotting.

Hemagglutination Titer

For the hemagglutination titer test, a series of two-fold dilutions of influenza VLPs in PBS were prepared and incubated at 25° C. for 40 min with 50 µL of 0.5% Turkey red blood cells. The extent of hemagglutination was observed visually, and the highest dilution that can agglutinate red blood cells was determined.

Sodium Dodecyl Sulfate Polyacrylamide Gel Electrophoresis (SDS-PAGE) and Western Blotting Each sucrose gradient fraction sample was treated with 1×SDS gel-loading buffer (50 mM Tris-HCl, 100 mM dithiothreitol, 2% SDS, 0.1% bromophenol blue, and 10% glycerol) for 5 min, resolved on 12% SDS-PAGE, and then transferred to PVDF membranes. Following the transfer, the PVDF membranes were blocked using 10% milk on an orbital shaker for 1 hour. Then the membranes were first reacted with anti-HA (Abcam ab21297), anti-M1 (Abcam ab25918), anti-NA (Abcam ab70759), anti-M2 (novus NB100-2073) or anti-EGFP (novus NB-600-601ss) antibodies for 1 hour, then reacted with the goat anti-rabbit or goat anti-mouse IgG conjugated with HRP (horse radish peroxidase) for 1 hour. Enhanced chemiluminescence (ECL) was detected through binding to HRP and visualized on a Fuji Medical X-ray film using a Western blot detection system (Amersham Bioscience).

Transmission Electron Microscopy (TEM)

The purified sucrose fractions containing VLPs were pooled and ultracentrifugated using the Hitachi RPS40ST rotor 2 hours at 33,000 rpm and 4° C. to remove the sucrose and to pellet the VLPs. The VLP pellets were resuspended with 200 μL PBS. For deep staining of the grid, 3 μL purified VLPs was added to the carbon-coated copper grid and stained three times with uranyl acetate before being vacuum-dried overnight.

Confocal Fluorescence Microscopy

A549 cells were grown on glass coverslips. VLPs were labeled with DiI (Vybrant DiI cell labeling solution) and A549 cells were labeled with DiD (Vybrant DiD cell labeling solution). Labeled VLPs were incubated with labeled A549 cells and analyzed by confocal fluorescence microscopy. DiI was excited by the 561 nm line of a laser. DiD was excited by the 633 nm line of a laser. EGFP was excited by the 488 nm line of a laser.

Mouse Immunization

A group of five female BALB/c mice (6 to 8 weeks old) was used for immunization studies. Immunizations were performed by intramuscular injection of 15 μg of the purified VLPs (suspended in PBS at pH 7.4) for each dose and three doses were conduced in a 3-week interval. Blood was collected 2 weeks after third immunization and serum was isolated. All experiments were conducted in accordance with the guidelines of the Laboratory Animal Center of National Tsing Hua University (NTHU). Animal use protocols were reviewed and approved by the NTHU Institutional Animal Care and Use Committee (approval no. 09733).

H5-pseudotyped Particles (H5 pp)

$3 \times 10^6$ HEK293T cells were transfected with pNL-Luc-E⁻R⁻, pcDNA3.1-HA (A/Thailand/1(KAN-1)/2004/H5N1 and A/Anhui/1/2005/H5N1) and pcDNA4B-NA (A/Viet Nam/1203/2004/H5N1) vectors. Cell supernatant that contained pseudotyped HIV-1 particles with H5N1 HA and NA were collected 48 hours post-transfection and purified through a 0.45 μm filter. The supernatant was concentrated by ultracentrifugation at 33,000 rpm for 2.5 hours, and then each pellet was dissolved in 100 μL PBS. An HIV-1 p24 ELISA assay kit (BioChain) was used to quantify the H5 pp particles.

Neutralization Assay

MDCK cells (4000 cells/well) were seeded in 100 μL of DMEM in 96-well plates. The amount of 25 ng of p24 H5 pp was incubated with two-fold serial dilutions of serum (starting dilution 1:40) for 1 hour at 37° C. in 60 μL DMEM. Then 100 μL of fresh medium was added and 140 μL of the virus-serum mixtures was transferred to the cells. The luciferase assay was performed 48 hours following the direct addition of neolite luciferase substrate (PerkinElmer). The neutralization titer was defined as the reciprocal of the dilution that yielded 50% neutralization determined using an ID50 software.

Analysis of Cytokine Production

DCs were untreated or individually treated with LPS 50 ng/mL from *E. coli* 0111:B4 (Sigma), PBS, 1 μg/mL VLP, FliC-VLP or PRO-VLP for 6 hours, with the addition of a protein transport inhibitor, brefeldin A (10 μg/mL) (Biolegend), for the final 4.5 hours. Cells were then fixed and permeabilized, and the intracellular cytokines were stained with TNF-α mAb (Biolegend). They then underwent flow cytometry (FACS Calibur, BD) and analyzed using CellQuest software (BD Biosciences).

Analysis of DC Maturation

After the BMDCs were untreated or treated with VLPs, FliC-VLPs or PRO-VLPs (5 μg/mL) for 16 hours, the cells and supernatants were harvested and stained with monoclonal antibodies against conjugated CD11c-FITC, conjugated CD40-PE, and conjugated CD86-PE (Biolegend). The cells were then acquired and analyzed using flow cytometry (FACS Calibur, BD).

Results

Baculovirus-insect Cell Expression of Influenza VLPs

Figure 11:
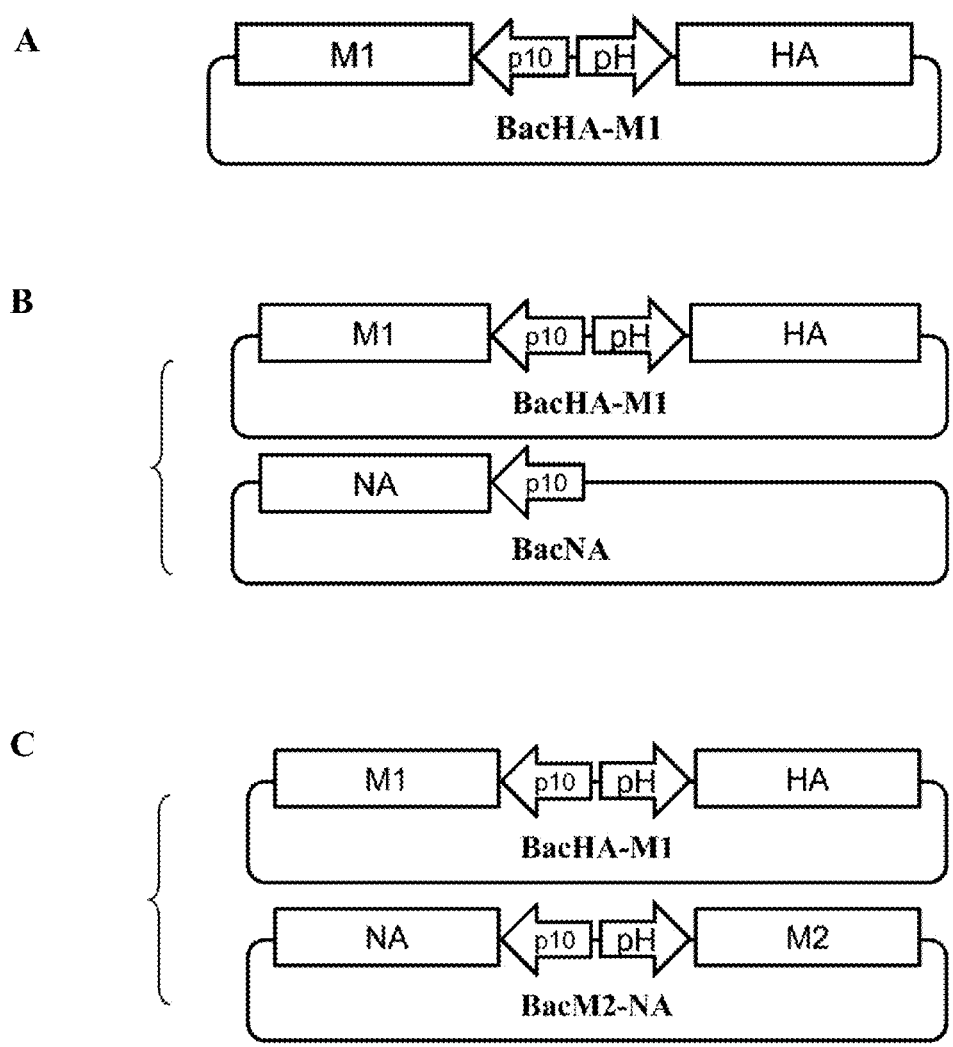
FIG. 11 shows construction of baculovirus expression vector for influenza VLP production. Influenza VLPs are obtained from Sf9 cells that are infected with (A) a single baculovirus that encodes two viral proteins (BacHA-M1) (B) two baculoviruses that encode three viral proteins (BacHA-M1 and BacNA) (C) two baculoviruses that encode four viral proteins (BacHA-M1 and BacNA-M2). pH: polyhedron promoter; p10: p10 promoter.
Figure 12:
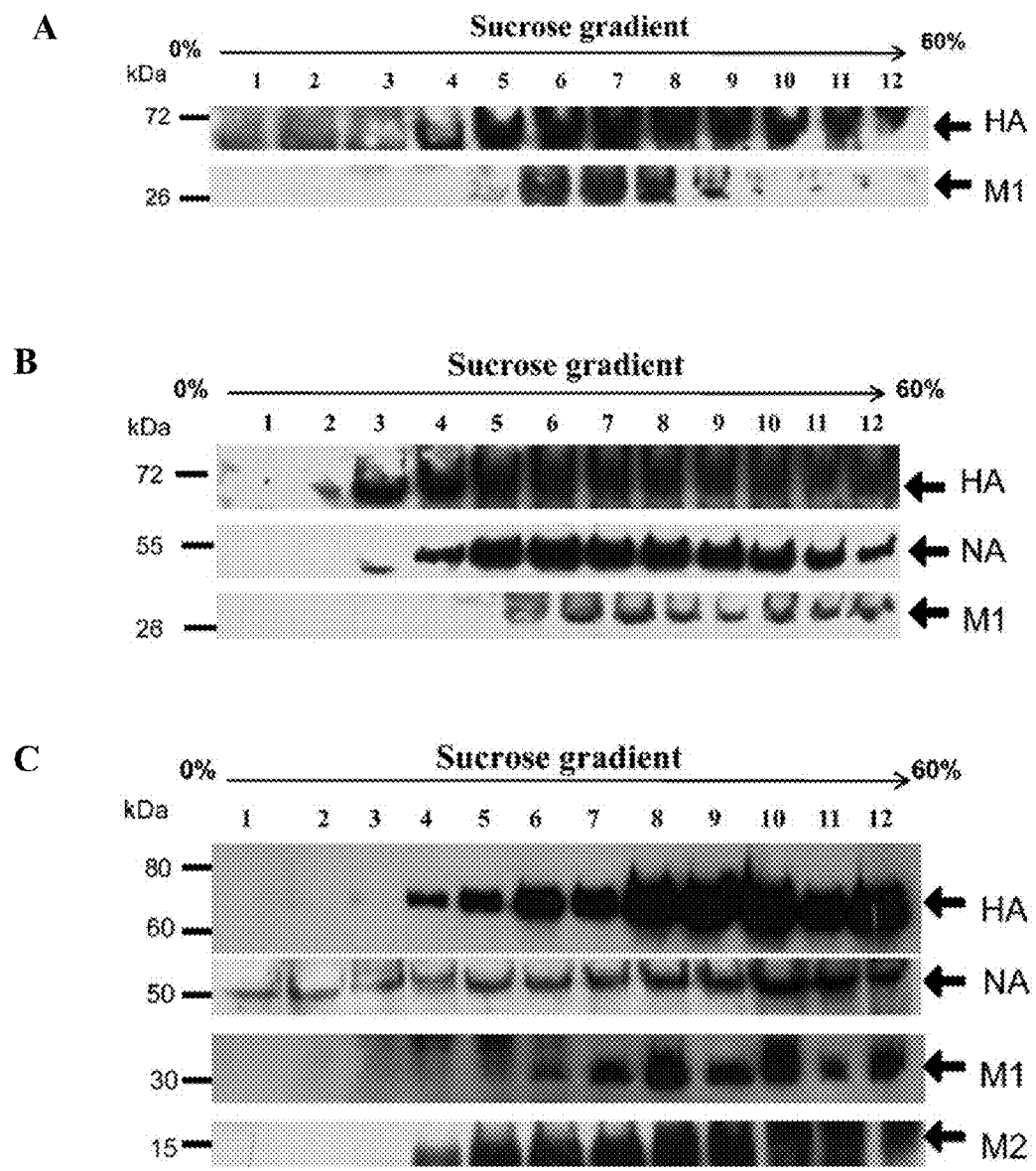
FIG. 12 shows sucrose gradient analyses of the influenza VLPs obtained by the expression by baculovirus of (A) two viral proteins (HA and M1); (B) three viral proteins (HA, NA, M1); and (C) four viral proteins (HA, NA, M1, M2). Purified sucrose fractions were resolved in SDS-PAGE gels and reacted with anti-HA, anti-M1, anti-NA, and anti-M2 antibodies.
Figure 13:
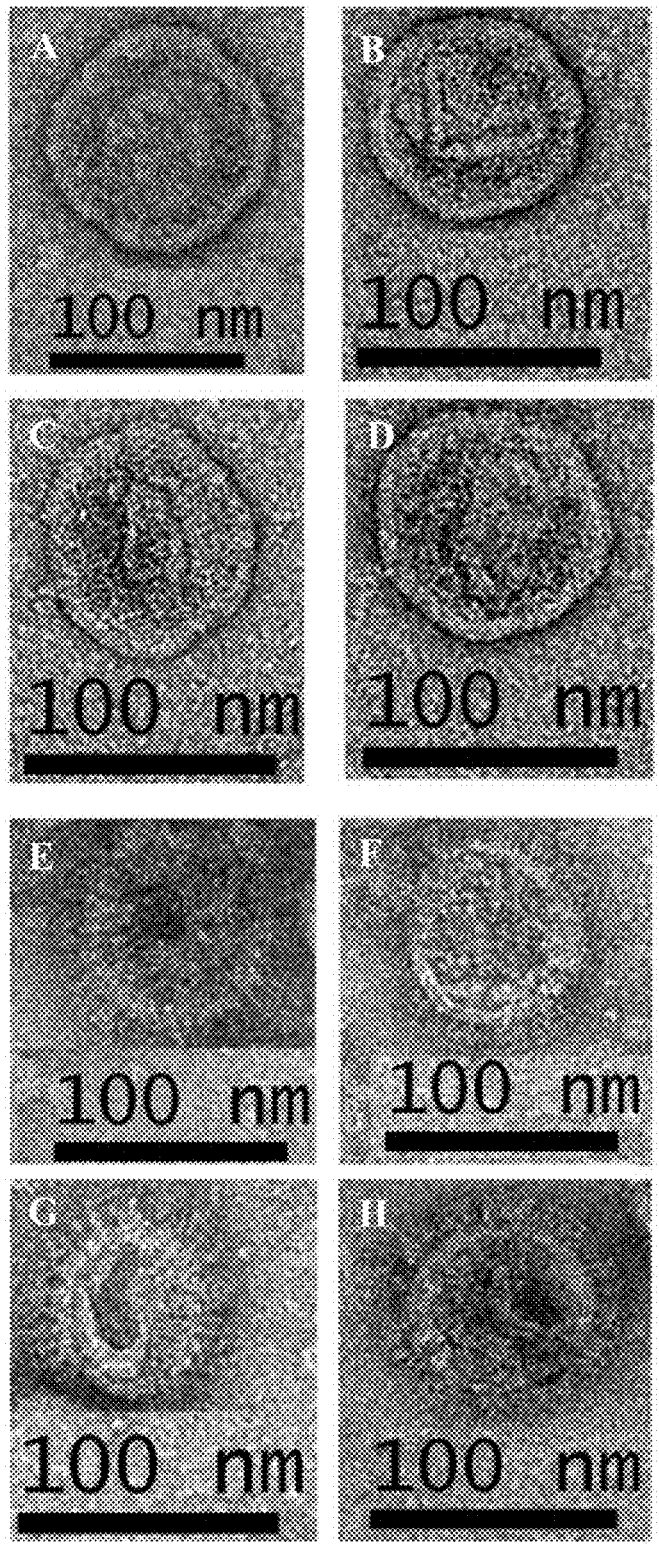
FIG. 13 shows TEM analyses of influenza VLPs expressed by baculovirus using (A-D) two viral proteins (HA and M1); (E-H) three viral proteins (HA, NA, M1); and (I-L) four viral proteins (HA, NA, M1, M2). The TEM images present quadruple samples for each case of negative staining of influenza VLPs with uranyl acetate.
Figure 13:
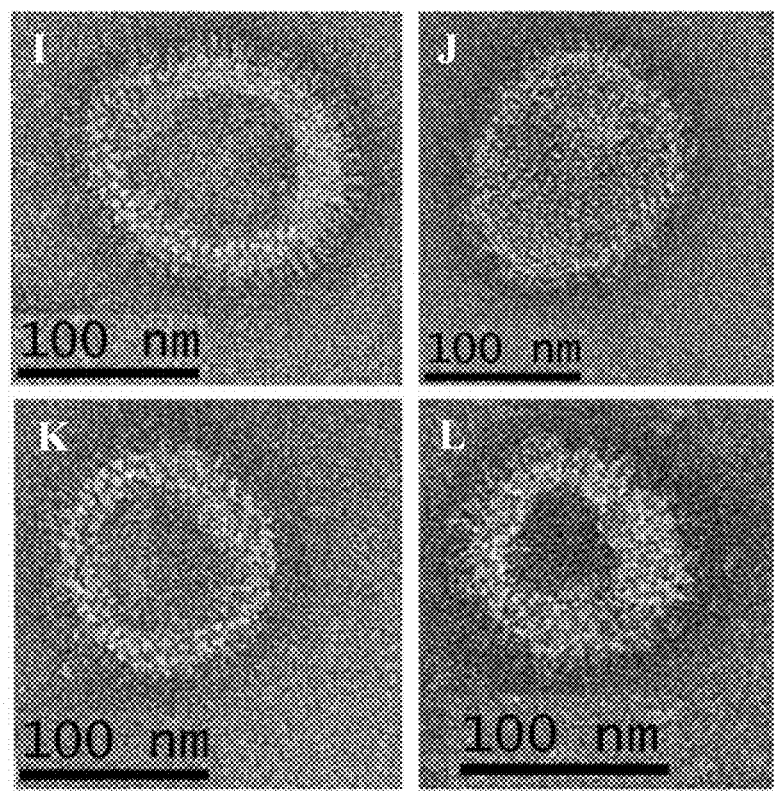
Figure 14:
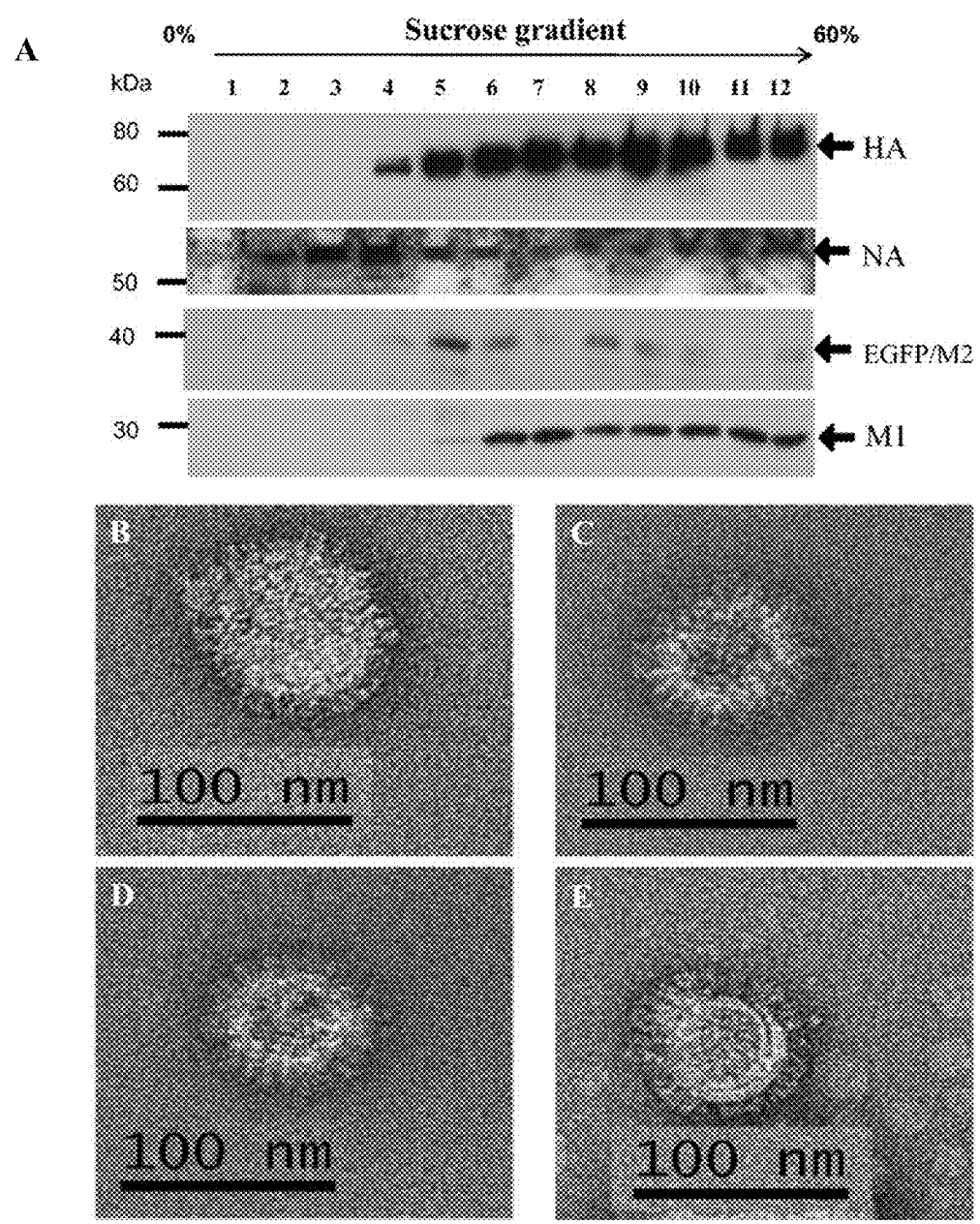
FIG. 14 shows production of influenza VLPs with EGFP/M2 fusion protein. (A) Sucrose gradient analysis of influenza VLPs, reacted with anti-HA, anti-NA, anti-M1, anti-EGFP specific antibodies; (B-E) TEM images of influenza EGFP-VLPs that are negatively stained with uranyl acetate, showing quadruple samples.

A baculovirus-insect cell expression system was used to prepare the influenza VLPs by the over-expression of two viral proteins (HA, M1), three viral proteins (HA, NA, M1), and four viral proteins (HA, NA, M1, M2). The cDNAs of the four viral proteins were obtained from different influenza virus strains: HA (A/Thailand/1(KAN-1)/2004/H5N1) (SEQ ID NO: 1), NA (A/Viet Nam/1203/2004/H5N1) (SEQ ID NO: 27), M1 (A/WSN/1933/H1N1) (SEQ ID NO: 21) and M2 (A/WSN/1933/H1N1) (SEQ ID NO: 23). These genes were cloned into the baculovirus vector under two promoters, polyhedron (pH) and p10, to generate a series of recombinant baculoviruses (BacHA-M1, BacNA, BacM2-NA) (FIGS. 11A-C). Influenza VLPs were obtained from Sf9 cells that were infected with BacHA-M1 (two viral proteins), co-infected with BacHA-M1 and BacNA, or co-infected with BacHA-M1 and BacM2-NA. Influenza VLPs were obtained from the culture supernatants and purified by ultracentrifugation and sucrose gradient sedimentation. The formation of influenza VLPs was in the sucrose gradient fractions verified by Western blotting in the presence of two viral proteins HA and M1 (FIG. 12A), three viral proteins HA, NA, M1 (FIG. 12B), and four viral proteins HA, NA, M1, M2 (FIG. 12C). The TEM results reveal that the VLPs obtained from infected Sf9 cells were roughly spherical and were pleomorphic. The average diameters of the influenza VLPs were 102±3 nm (N=10) for two viral proteins, 100±4 nm (N=10) for three viral proteins, and 97±13 nm (N=10) for four viral proteins (FIG. 13). Distinctive influenza spike projections were observed on the surface of the VLPs expressed using three and four viral proteins (FIG. 13). The influenza VLPs that were expressed using two, three and four viral proteins were all capable of maintaining red blood cell agglutination as determined from the HA titers of 512 (two viral proteins), 256 (three viral proteins), and 512 (four viral proteins) per 50 μL.

Production of Influenza VLPs with EGFP/M2 Fusion Protein

It was proposed that M2 protein can be used as a molecular fabricator (i) without disrupting the assembly of VLPs and (ii) while retaining the native structures of HA and NA envelope proteins on the particle surfaces. Fabrication of influenza VLPs was obtained by the over-expression of four viral proteins by a direct fusion of M2 to EGFP. The EGFP gene was added to the N terminus of the M2 gene to construct the baculovirus (BacEGFP/M2-NA). Sf9 cells were co-infected with two recombinant baculoviruses (BacHA-M1 and BacEGFP/M2-NA) to generate the EGFP-VLPs. Direct fusion of EGFP to M2 did not influence the formation of VLPs as revealed by the presence of four viral proteins in the sucrose gradient fractions (FIG. 14A) and the TEM visualization of the spherical and pleomorphic particles with an average diameter of 93±13 nm (N=10) (FIGS. 14B-E).

Figure 15:
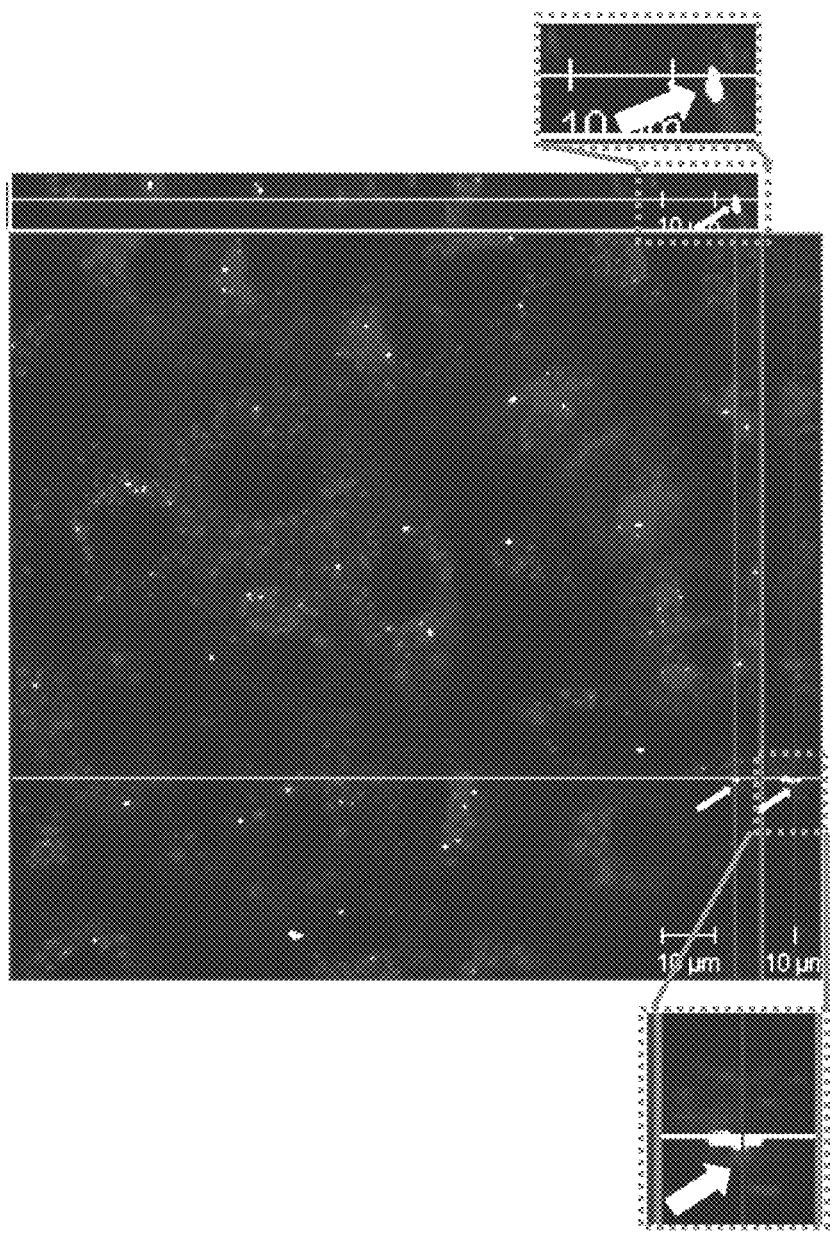
FIG. 15 shows EGFP-VLPs in A549 cells visualized by confocal fluorescence microscopy. A549 cells were labeled with DiD and EGFP-VLPs were labeled with DiI. (A) Excitation by 488 nm line from laser and 633 nm line from laser; (B) excitation by 561 nm line from laser and 633 nm line from laser.
Figure 15:
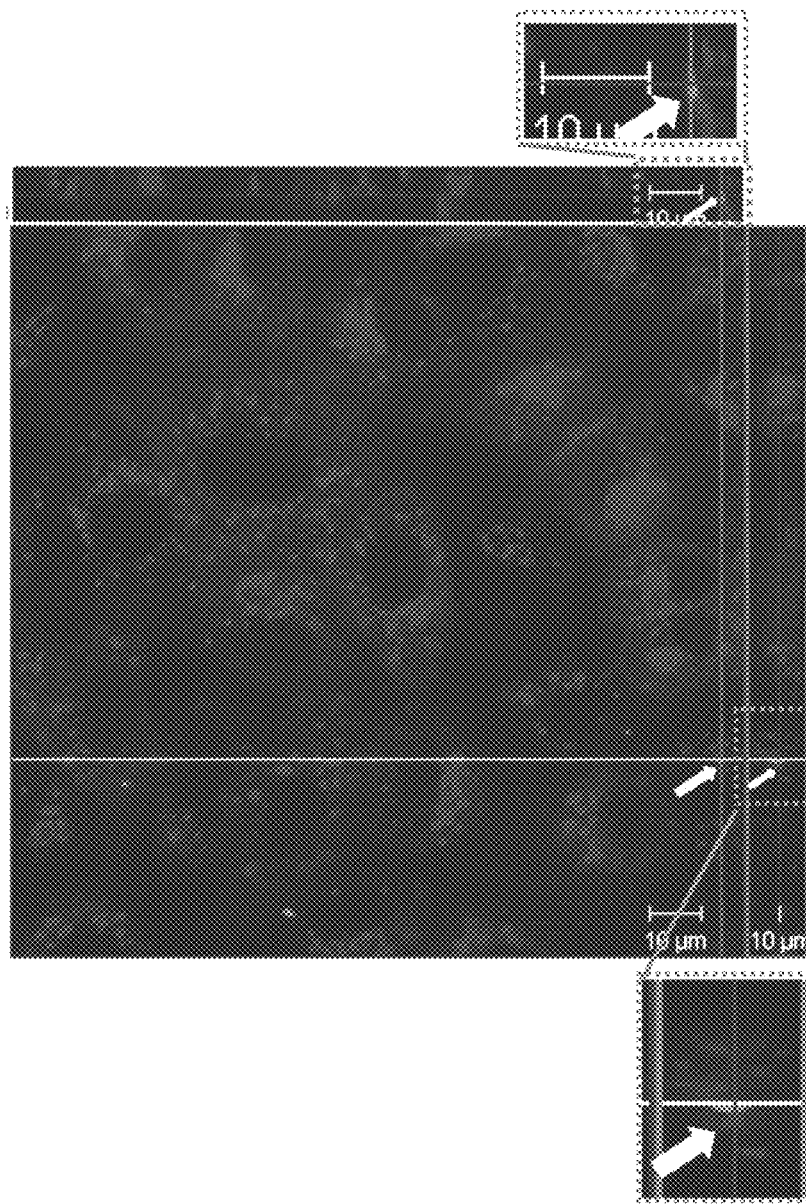

To further show the functionality of the EGFP-VLPs, live cell imaging was used to visualize the uptake of EGFP-VLPs in A549 cells. Using confocal microscopy at various wavelengths of emitted light green fluorescent spots of the EGFP-VLPs were observed inside the A549 cells with light that was excited at 488 nm (FIG. 15A), and overlapped the red fluorescent spots of the VLPs that were stained with DiI, which is a fluorescent lipophilic dye that was used to label viral membranes within the A549 cells with an excited light wavelength of 561 nm (FIG. 15B). In parallel, A549 cells were labeled with DiD, a fluororescent lipophilic dye for labeling cell membranes, yielding blue fluorescent spots with an excited light wavelength at 633 nm. These results reveal that influenza VLPs can be generated by the M2 fusion of EGFP for imaging single virus entering A549 cells.

Production of Influenza VLPs with Flagellin/M2 and Profilin/M2 Fusion Proteins

Figure 16:
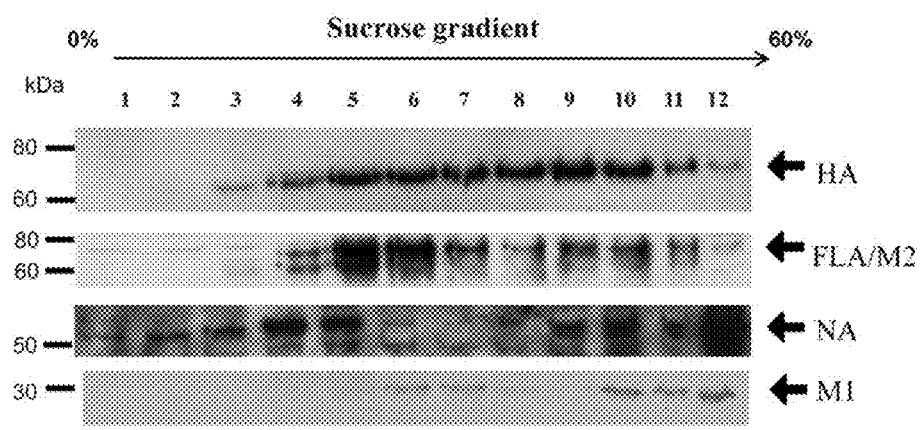
FIG. 16 shows production of influenza VLPs with FliC/M2 fusion protein. (A) Sucrose gradient analysis of influenza VLPs reacted with anti-HA, anti-NA, anti-M1, anti-M2 specific antibodies; (B-E) TEM images of influenza FliC-VLPs that are negatively stained with uranyl acetate, showing quadruple samples.
Figure 16:
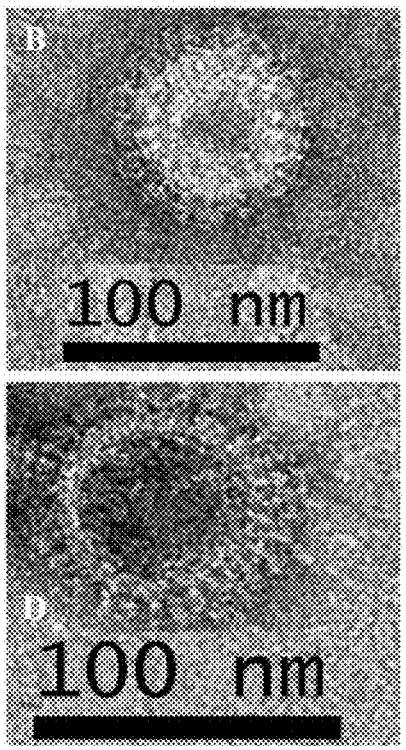
Figure 16:
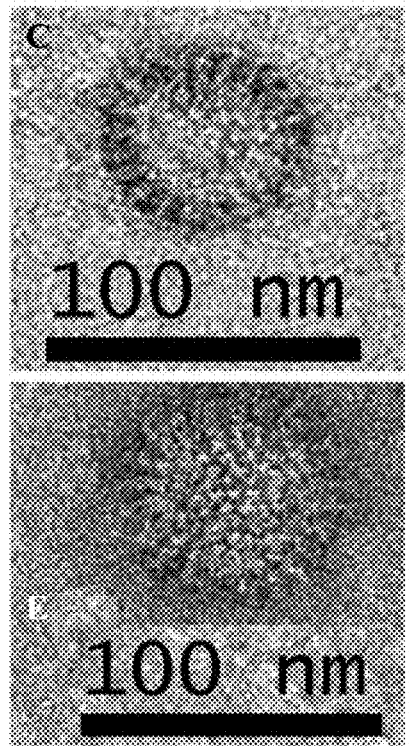
Figure 17:
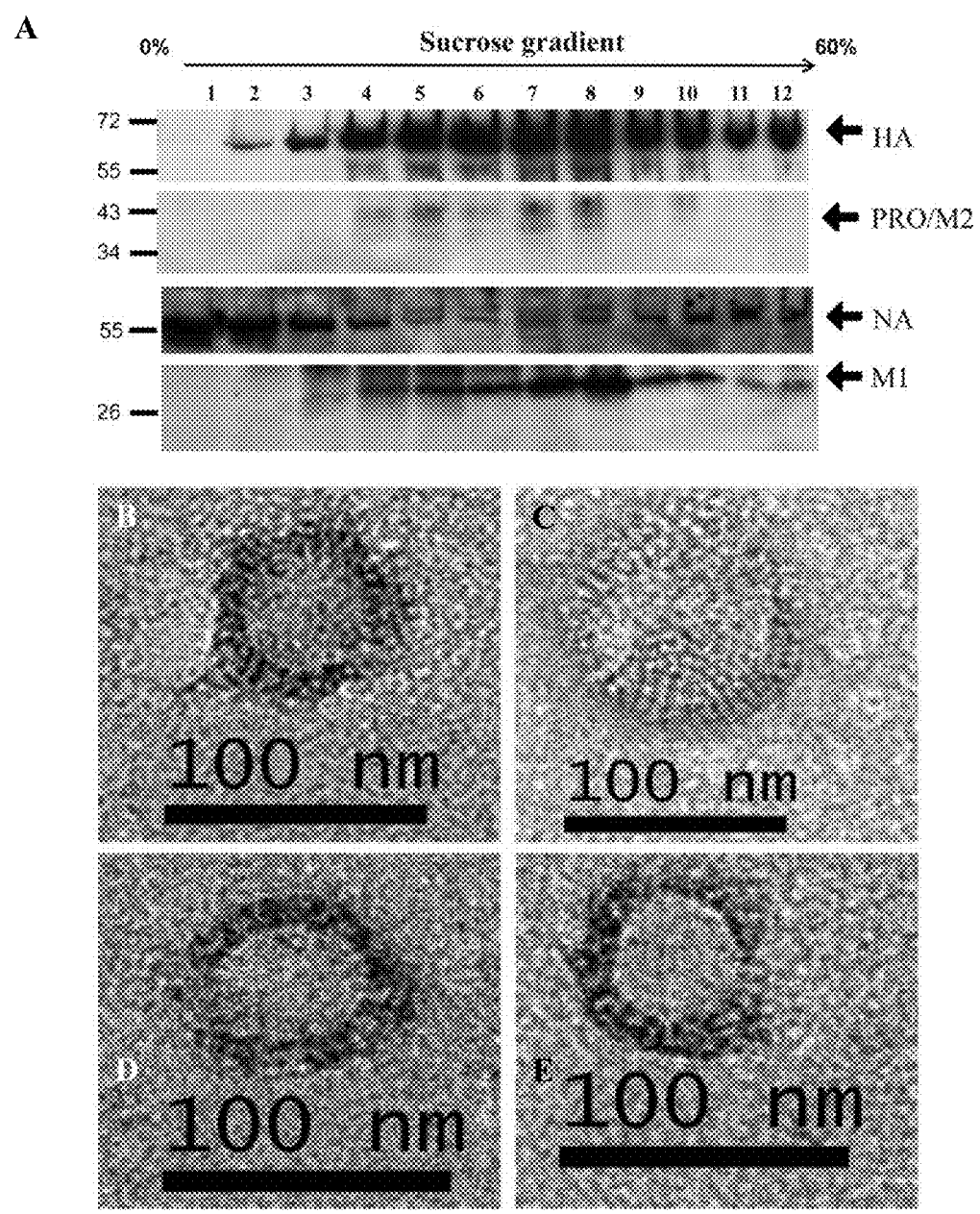
FIG. 17 shows production of influenza VLPs with PRO/M2 fusion protein. (A) Sucrose gradient analysis of the influenza VLPs reacted with anti-HA, anti-NA, anti-M1, and anti-M2 specific antibodies; and (B) TEM images of influenza PRO-VLPs that are negatively stained with uranyl acetate, showing quadruple samples.

Two molecular adjuvants, FliC and PRO, were then replaced with EGFP to generate two molecular adjuvanted VLPs, FliC-VLPs and PRO-VLPs. The full-length genes of FliC and PRO were fused in front of the M2 gene to construct the recombinant baculoviruses, BacFliC/M2-NA and BacPRO/M2-NA. Sf9 cells were co-infected with BacHA-M1 and Bac FliC/M2-NA or BacHA-M1 and BacPRO/M2-NA to yield FliC-VLPs and PRO-VLPs. Direct fusion of FliC and PRO to M2 formed FliC-VLPs (FIG. 16A) and PRO-VLPs (FIG. 17A) as evidenced by the presence of the fusion proteins and other three viral proteins HA, NA, M1 in the sucrose fractionated samples. The morphologies of FliC-VLPs and PRO-VLPs were spherical and pleomorphic, with average diameters of 94±7 nm (N=10) and 94±13 nm (N=10), respectively (FIGS. 6B-E and 17B-E). These results reveal that the molecular adjuvanted VLPs can be obtained using M2 fusion proteins.

Figure 18:
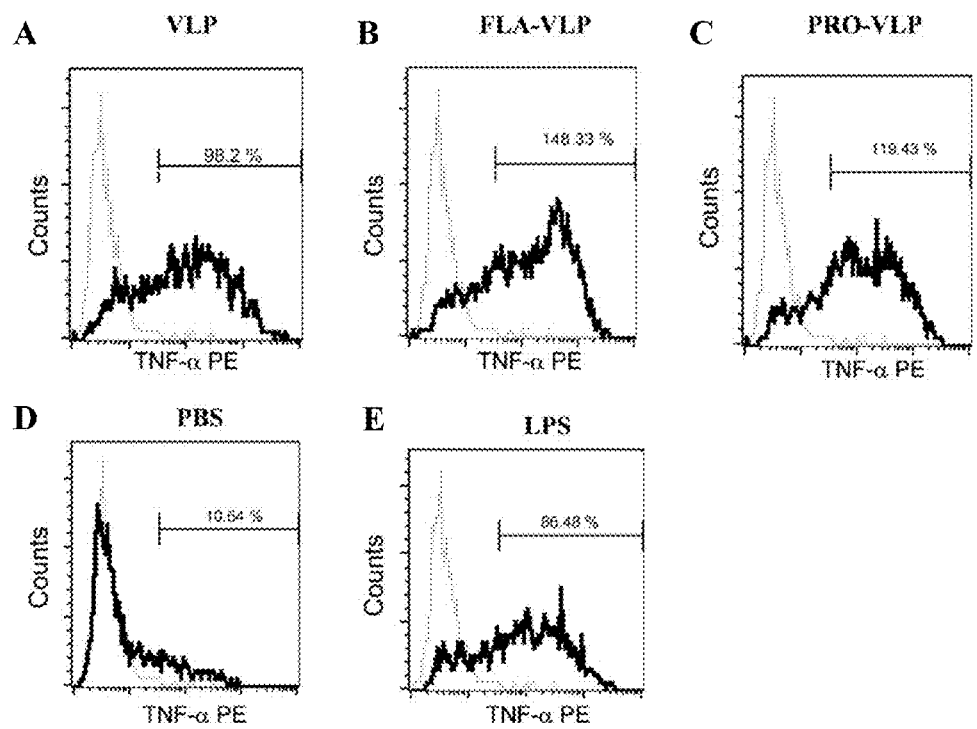
FIG. 18 shows intracellular TNF-α production of BMDCs treated with (A) non-fabricated VLPs, (B) FliC-VLPs, (C) PRO-VLPs, (D) PBS (negative control), or (E) 20 ng/mL LPS (positive control). TNF-α production was detected by FACS analysis in groups of treated (black lines) and untreated (gray lines) BMDCs. Average TNF-α+ BMDCs of gated M1 were obtained from at least three independent experiments.
Figure 19:
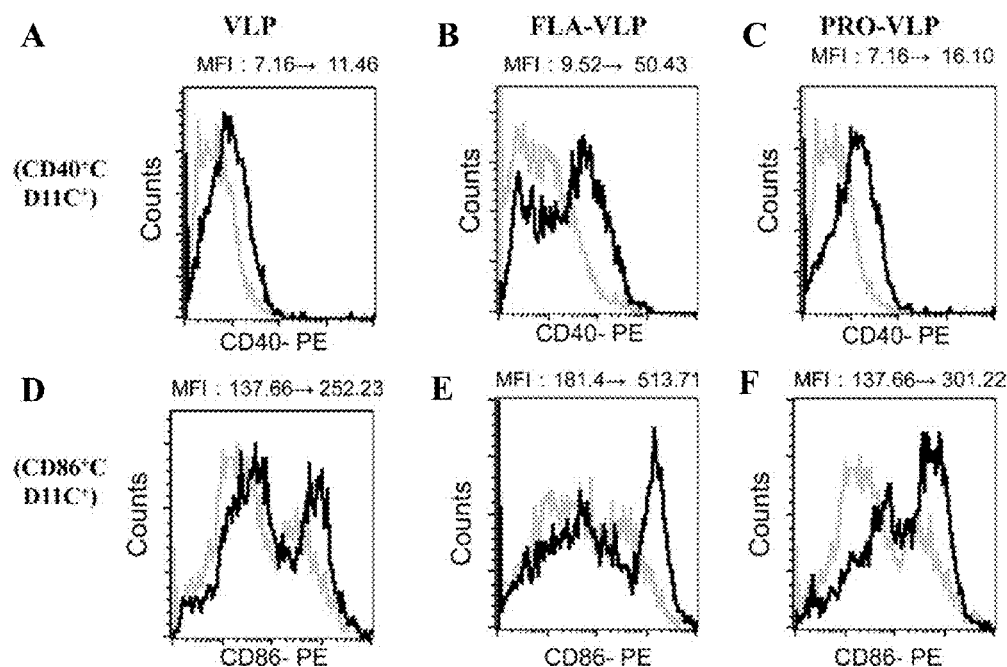
FIG. 19 shows analytic results of CD40 and CD86 surface markers on BMDCs treated with non-fabricated VLPs, FliC-VLPs and PRO-VLPs. The mean fluorescence intensity (MFI) of the groups of treated (black lines) and untreated (gray lines) BMDCs are presented in (A) $CD40^+CD11c^+$ and (B) $CD86^+CD11c^+$ phenotypes. Results are obtained from triplicate experiments.

To study the effects of molecular adjuvanted VLPs on dendritic cells, mouse BMDCs were obtained in vitro, treated with various influenza VLPs (VLPs, FliC-VLPs, PRO-VLPs) and then analyzed using FACS analysis. The results indicate that the production of TNF-$\alpha$ in BMDCs increased from 98.2% (VLP) to 148.3% (FliC-VLP) and 119.4% (PRO-VLP) than in the controls of untreated (10.6%) and LPS-treated BMDC cells (86.5%) (FIG. 18). The maturation of BMDCs that was caused by influenza VLPs was also elucidated by measuring the amount of the co-stimulatory molecules of CD40 and CD86 on the surfaces of BMDCs. The results show that since the mean fluorescence intensities (MFI) of $CD40^+CD11c^+$ and $CD86^+CD11c^+$ in BMDCs upon treatment with FliC-VLPs and PRO-VLPs increased above those in VLPs (FIG. 19), the molecular adjuvanted VLPs (FliC-VLPs and PRO-VLPs) induced BMDCs to produce more TNF-$\alpha$ and to promote more DC maturation in vitro.

Figure 20:
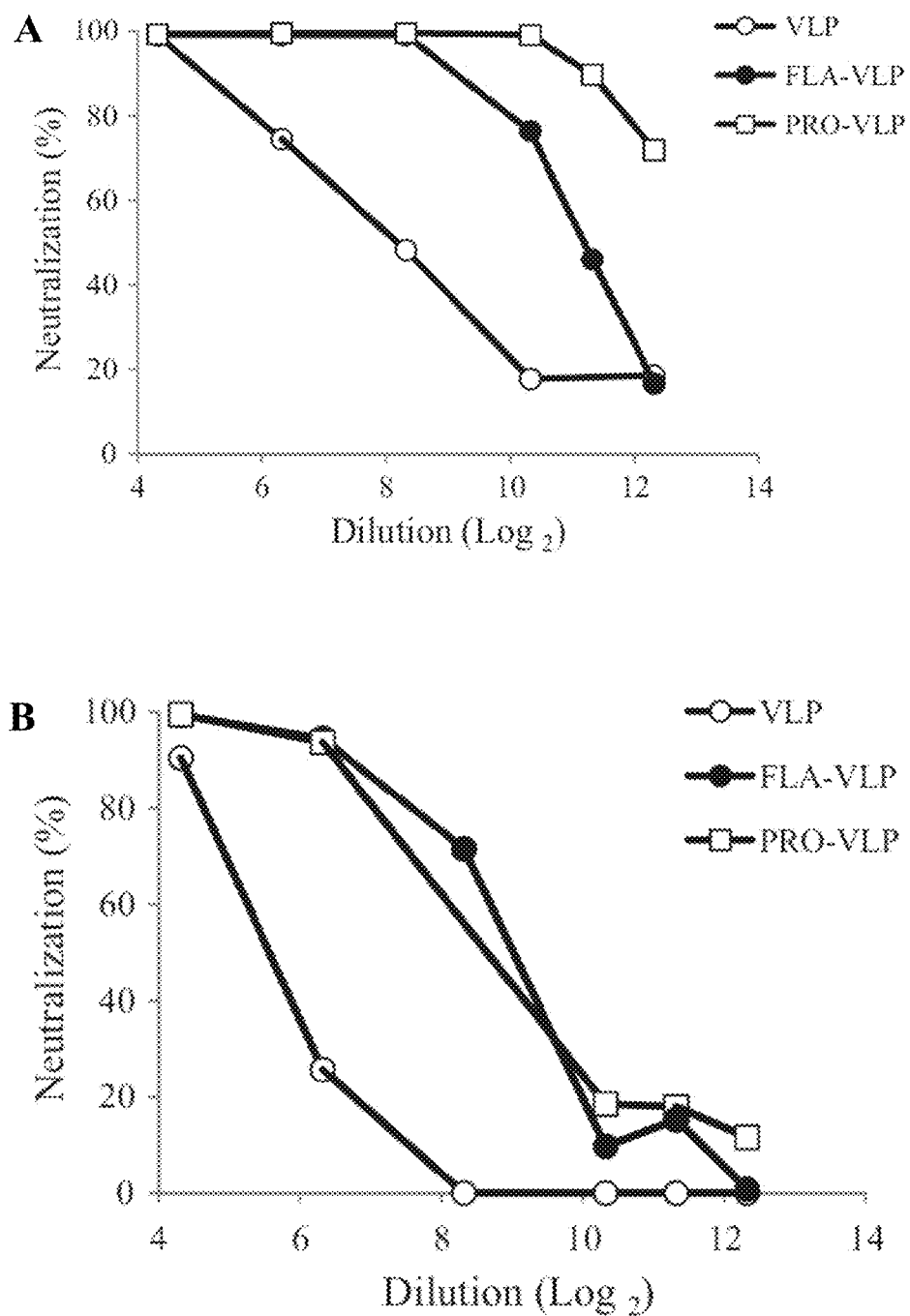
FIG. 20 shows neutralization of antisera collected from mice immunized with VLPs, FliC-VLPs and PRO-VLPs using H5 pp of (A) the homologous KAN-1 strain and (B) the heterologous Anhui strain.

To investigate whether immunization with the molecular adjuvated FliC-VLPs and PRO-VLPs can elicit more potent immune responses than the wild-type VLPs, BALB/c mice were immunized with VLPs, FliC-VLPs, and PRO-VLPs at 15 μg (total protein) per dose for three immunizations. The mouse sera were collected one week after the third immunization and analyzed for H5pp neutralization. The results show that the antisera that were collected from mice that have been immunized by VLPs, FliC-VLPs and PRO-VLPs neutralized H5pp of the homologous KAN-1 strain (FIG. 20A) and the heterologous Anhui strain (FIG. 20B) were all in a dose-dependent manner. For neutralization of the homologous strain, the 50% neutralization titers were $\log_2$ 6.5 for VLP antisera, $\log_2$ 11.2 for FliC-VLP antisera, and $\log_2$ 12.8 for PRO-VLP antisera. For neutralization of the heterologous Anhui strain, the 50% neutralization titers were $\log_2$ 5.7 for VLP antisera, $\log_2$ 8.8 for FliC-VLP antisera, and $\log_2$ 9.3 for PRO-VLP antisera. Immunization using the fabricated VLPs that contained the molecular adjuvants (PRO-VLPs and FliC-VLPs) elicited more potent neutralizing antibody responses in mice against the homologous and the heterologous H5N1 viruses than the wild-type VLPs.

Example 3

Material and Methods
Ethics Statement

The animal studies were conducted in accordance with guidelines established by the Laboratory Animal Center of National Tsing Hua University (NTHU). Animal use protocols were reviewed and approved by the NTHU Institutional Animal Care and Use Committee (approval no. 09931). Mouse challenge experiments were evaluated and approved by the Institutional Animal Care and Use Committee of Academia Sinica. Mice survived from immunization experiments were sacrificed using carbon dioxide ($CO_2$) following ISCIII IACUC guidelines to ameliorate suffering.

Recombinant H5HA Protein Construction and Purification

Soluble H5HA proteins were constructed using four HA cDNA sequences: A/Thailand/1(KAN-1)/2004 (KAN-1, clade 1) (SEQ ID NO: 1), A/Indonesia/5/2005 (Indonesia, clade 2.1) (SEQ ID NO: 29), A/bar-headed goose/Qinghai/1A/2005 (Qinghai, clade 2.2) (SEQ ID NO: 30), and A/Anhui/1/2005 (Anhui, clade 2.3.4) (SEQ ID NO: 31). The A/Thailand/1(KAN-1)/2004 HA gene was kindly provided by Prasert Auewarakul of Siriraj Hospital at Mahidol University, Thailand. The PQRERRRKKRG multibasic protease cleavage site between HA1 and HA2 was mutated to PQRETRG to prevent furin cleavage in cells. To obtain a trimeric H5HA protein, the C-terminus of the HA ectodomain was serially fused with a thrombin cleavage site, the GCN4-pII leucine zipper sequence, and a His-tag to facilitate protein purification. For large-scale production, Sf9 cells (Invitrogen) were grown in SF900-II serum-free medium (Invitrogen) at a density of $2\times10^6$ cells/ml prior to infection with recombinant baculoviruses produced by the Bac-to-Bac expression system (Invitrogen). After 2 d post-infection, supernatants were collected for trimeric H5HA purification using nickel-chelated affinity chromatography (Tosoh). Trimeric H5HA protein expression was determined by SDS-PAGE and Western blots using polyclonal anti-H5HA antibodies (ab21297; Abcam).

A glycan-masked H5HA antigen design was introduced using site-directed mutations on residues 83 ($^{83}ANP^{85}$ replaced by $^{83}NNT^{85}$ and named g83, the cDNA sequence and the mature protein product derived from the cDNA sequence of g83 mutation were shown as SEQ ID NO: 3 and SEQ ID NO: 4, respectively), 127 ($^{127}ASL^{129}$ replaced by $^{127}NSS^{129}$ and named g127, the cDNA sequence and the mature protein product derived from the cDNA sequence of g127 mutation were shown as SEQ ID NO: 9 and SEQ ID NO: 10, respectively), and 138 ($^{138}QRK^{140}$ replaced by $^{138}NGT^{140}$ and named g138, the cDNA sequence and the mature protein product derived from the cDNA sequence of g138 mutation were shown as SEQ ID NO: 32 and SEQ ID NO: 33, respectively). Double and triple mutants of glycan-masked hemagglutiinin (HA) antigens at residues 83, 127 and 138 (i.e. g83+g127, g127+g138, g83+g138 and g83+g127+g138) were also made. The cDNA sequence and the mature protein product derived from the cDNA sequence of g83+g127 mutation were shown as SEQ ID NO: 34 and SEQ ID NO: 35, respectively; the cDNA sequence and the mature protein product derived from the cDNA sequence of g127+ g138 mutation were shown as SEQ ID NO: 36 and SEQ ID NO: 37, respectively; the cDNA sequence and the mature protein product derived from the cDNA sequence of g83+ g138 mutation were shown as SEQ ID NO: 38 and SEQ ID NO: 39, respectively; and the cDNA sequence and the mature protein product derived from the cDNA sequence of g83+ g127+g138 mutation were shown as SEQ ID NO: 40 and SEQ ID NO: 41, respectively. The method for producing these glycan-masked H5HA antigens was as described in the above Examples, in which these mutations were based on the wild-type H5HA cDNA sequence (SEQ ID NO: 1) and its mature protein (SEQ ID NO: 2). It was noted that the first 16 amino acids of the protein encoded by H5HA cDNA would be cut off during protein mature process in cells. The RBS mutant H5HA protein (ΔRBS-H5HA) was constructed with the introduction of an N-glycan (E186N mutation) into the RBS 190 helix. The stem mutant H5HA protein (ΔStem-H5HA) was constructed with the introduction of an N-glycan (I375N and G377T mutations) in the mid-stem helix A. The H5HA mutants, also produced by the Bac-to-Bac expression system, were constructed as soluble trimeric forms. Purified H5HA mutants were confirmed by fetuin binding and antibody binding assays using mAbs 9E8, 10D10 and C179 (TaKaRa).

Recombinant Adenovirus Vector Preparation

The ViraPower™ Adenoviral Expression System (Invitrogen) was used to create adenovirus vectors containing codon-optimized H5HA based on the A/Thailand/1(KAN-1)/2004 strain with a cleavage site mutation to retain uncleaved proteins. Briefly, a pENTR vector containing the H5HA gene was recombined (site-directed) with a pAd/CMV/V5-DEST vector using LR Clonase Enzyme Mix (Invitrogen). Following Pac I digestion, the recombined pAd/CMV/V5-DEST vector was transfected into HEK293A cells (Invitrogen) for adenovirus production. Recombinant adenoviruses encoding H5HA were produced 7 to 10 d post-transfection, with virus titers determined by plaque assays. H5HA proteins in cells infected with recombinant adenoviruses were confirmed by SDS-PAGE and Western blots using anti-H5HA antibodies.

Mouse Immunization

Female BALB/c mice (6-8 weeks old; 5 mice per group) were intramuscularly primed with $10^8$ pfu of H5HA-encoding adenovirus vectors followed by 20 μg boosters of corresponding recombinant H5HA proteins coupled with PELC/CpG 3 weeks later. Sera were collected at week 5.

Viral Challenge

Three weeks after the second immunization, the immunized mice were anesthetized and intranasally challenged with 10 $LD_{50}$ of the reassortant H5N1 virus of RG2 (clade 2.1) or the reassortant H5N1 virus of NIBRG23 (clade 2.2) all in a final volume of 50 μl. PBS-immunized mice were used as a mock control. Mouse survival rates and weight losses were monitored daily for 14 d. According to IACUC guidelines, body weight loss over 25% was used as an end-point.

ELISA Assays

Individual wells in 96-well plates were coated with recombinant HA proteins (0.2 μg/well) and blocked with 1% BSA. 2-fold serial dilutions of individual serum samples were incubated in each plate for 1 h and removed with 3 washes using PBS with 0.05% Tween-20. Goat anti-mouse IgG-conjugated HRP (Bethyl Laboratories, Inc.) was incubated in each well for 1 h followed by 3 additional washes. TMB substrate was incubated in each well for 15 min, followed by the addition of $2NH_2SO_4$ prior to readings at 450 nm absorbance. Endpoint titers were measured as the most dilute serum concentrations giving optical density readings >0.2 above a negative control.

HI Assay

Sera were treated with receptor-destroying enzyme (Denka Seiken) for 18 h at 37° C. followed by 56° C. for 30 min to inactivate enzyme activity. Treated sera were two-fold serially diluted (starting from 1:10) and incubated with 4 HA units of H5N1pp containing HA from KAN-1 (clade 1), Indonesia (clade 2.1), Qinghai (clade 2.2), or Anhui (clade 2.3.4) strains. Next, 0.5% turkey red blood cells were added and incubated for another 30 min at room temperature. HI titer was measured as the reciprocal of the highest dilution of sera which completely inhibiting hemagglutination.

H5pp Neutralization Assay

Neutralizing antibodies were quantified as reduced luciferase expression levels following H5pp transduction in MDCK cells. 50 μl H5pp ($50TCID_{50}$) was incubated with 50 μl of antisera (two-fold serial dilution, starting dilution 1:40) for 1 h at 37° C. followed by the addition of MDCK cells ($1.5 \times 10^4$ cells/well). At 2 d post-infection, cells were lysed with Glo Lysis Buffer (Promega). Luciferase activity was measured by the addition of neolite luciferase substrate (PerkinElmer). Neutralization titers (IC50) were measured as the serum dilution required to obtain a 50% reduction in RLU compared to control wells containing the virus only.

Protein Absorption and Antibody Competition Assays

Protein absorption and antibody competition assays were performed as previously described (Wei C J, Boyington J C, McTamney P M, Kong W P, Pearce M B et al. (2010) Induction of broadly neutralizing H1N1 influenza antibodies by vaccination. Science 329: 1060-1064). For the protein absorption assays, mouse antisera was pre-absorbed with wild-type, ΔRBS, or ΔStem H5HA (40 μg/ml) for 1 h. Pre-absorbed antisera was used to measure IgG titers using ELISAs with the H5HA of the KAN-1, Indonesia, Qinghai, or Anhui strains. For the CR6261 antibody competition assays, ELISA plates coated with KAN-1, Indonesia, Qinghai, or Anhui H5HA were incubated with mAb CR6261 (10 μg/ml) for 1 h prior to the addition of antisera pre-absorbed with ΔStem H5HA; IgG titers were then measured by ELISA assays. Percentages of mAb CR6261 competition were calculated as (IgG titer with control antibody−IgG titer with CR6261)/IgG titer with control antibody×100.

Fetuin Binding and Fetuin Binding Inhibition Assays

Individual wells in 96-well plates were coated with 50 μg/ml of fetuin (Sigma), held overnight at 4° C., and blocked with 1% BSA in PBS buffer followed by three washes with 0.05% Tween 20/PBS buffer. Serially diluted soluble H5HA proteins were pre-mixed with HRP-conjugated anti-His tag antibodies (Bethyl Laboratories, Inc.) for 30 min, added to individual plates, and incubated for 60 min at room temperature. After three additional washes, H5HA binding was detected by ELISA assays (450 nm OD). For the fetuin binding inhibition assays, H5HA proteins (2 μg/ml) were pre-mixed with serially diluted antisera for 1 h prior to measuring fetuin binding activity as described above. Titers (50% reduction) were measured as the serum dilution required to obtain a 50% reduction in OD450 compared to control wells containing H5HA only.

Statistical Analyses

All results were analyzed with one-way ANOVAs and Tukey's tests using software GraphPad Prism v5.03, with $p<0.05$ indicating statistical significance. All experiments were performed at least two times.

Acknowledgments:

We thank C. J. Wei and G. Nabel at the U.S. National Institutes of Health for providing mAbs 9E8, 10D10, CR6261, and FI6v3 used in this research.

Results
Glycan-masked H5HA at Residues 83, 127 and 138

Figure 21:
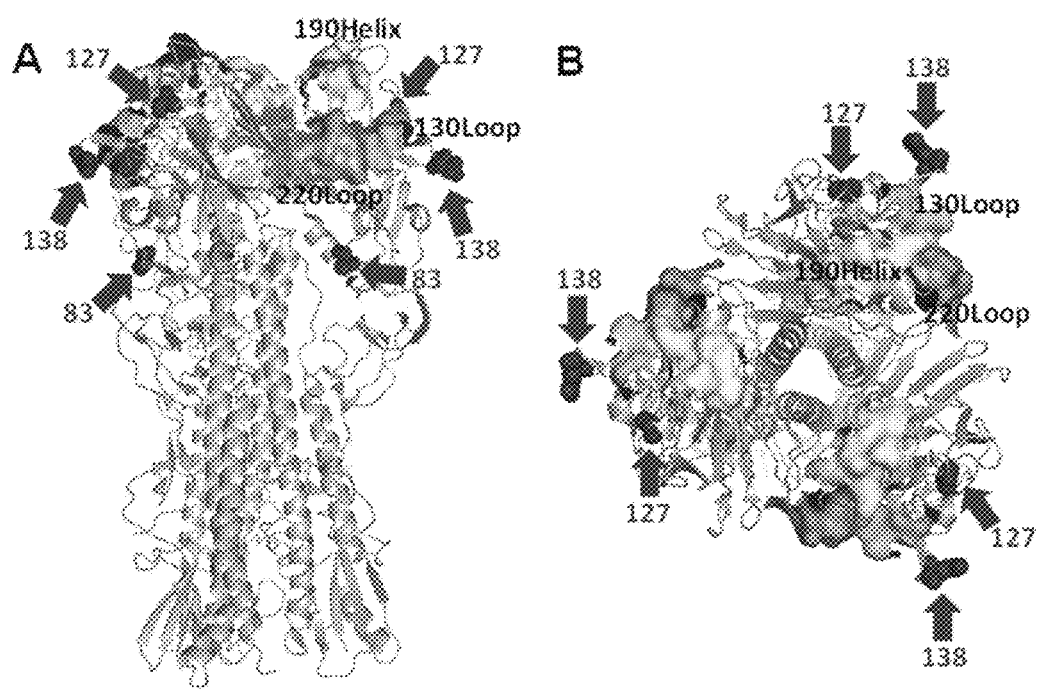
FIG. 21 shows a three-dimensional model of the KAN-1 HA structure generated by SWISS-MODEL based on the crystal structure of H5HA (A/Vietnam/1194/04, PDB ID: 2IBX). Images are created with PyMOL 1.3. RBS is composed of 130 loop, 190 helix, and 220 loop. Arrows indicate residues 83, 127 and 138.
Figure 22:
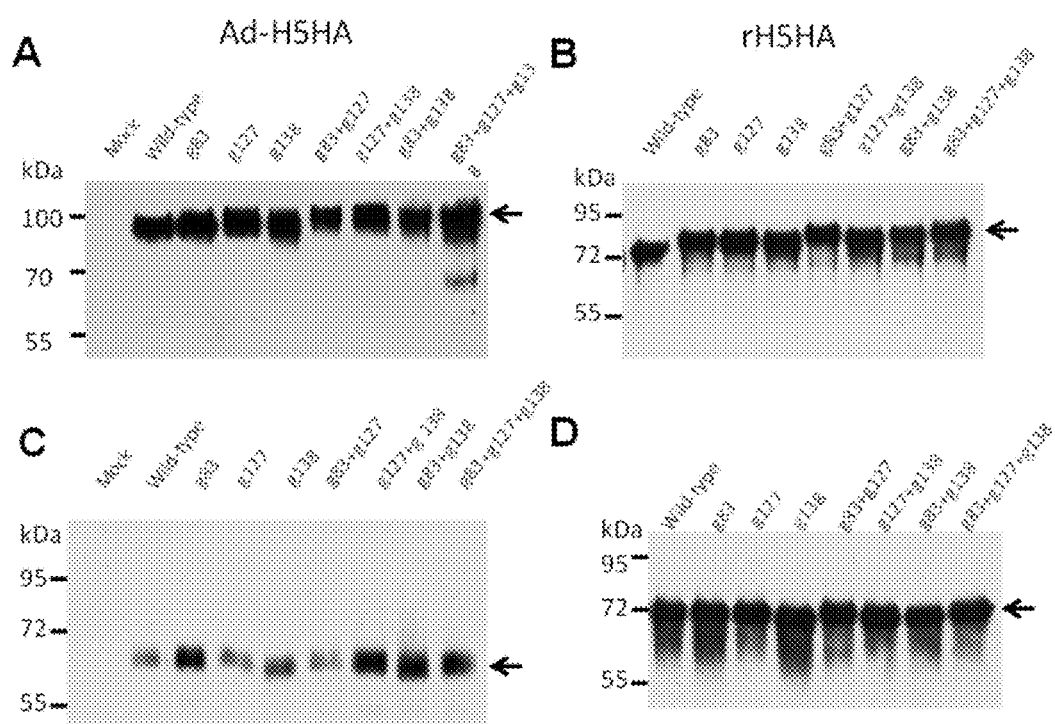
FIG. 22 shows expression of glycan-masked H5HA mutants. Single, double, and triple mutants of glycan-masked H5HA antigens at residues 83, 127 and 138 were constructed, and their corresponding HA-expressing adenovirus vectors and recombinant HA proteins were obtained. The increased molecular weights of (A) adenovirus-expressed H5HA mutants and (B) Sf9-expressed recombinant H5HA proteins were confirmed by Western blotting. Deglycosylated forms of (C) adenovirus-expressed H5HA mutants and (D) Sf9-expressed H5HA mutants were also confirmed following treatment with PNGase F.

In this example, the glycan-masked g138 mutant, which mutated to $^{138}$NGT$^{140}$ (data not shown) instead of $^{138}$NRT$^{140}$ used in the above examples, was able to induce broadly neutralizing antibodies similar to the glycan-masked g83 and g127 mutants. As elucidated in the three-dimensional H5HA structures shown in FIG. 21, residues 127 and 138 were located on the outer HA surface, close to the 130 loop of the receptor binding site (RBS). Residue 83 was located near the HA monomer interface that was observable from a side view (FIG. 1A) but not from a top view (FIG. 1B). For the example, single, double, and triple mutants of glycan-masked H5HA antigens at residues 83, 127 and 138 (i.e. g83, g127, g138, g83+g127, g127+g138, g83+g138 and g83+g127+g138) were constructed, and their corresponding HA-expressing adenovirus vectors and recombinant HA proteins were then obtained. These mutants were found to have increased molecular weights for both H5HA protein adenovirus vectors (FIG. 22A) and recombinant H5HA proteins (FIG. 22B) compared to the wild type H5HA constructs. However, molecular weights were equal following PNGase F treatment (FIGS. 2C and 2D).

H5HA-specific Total IgG Titers Elicited by Glycan-masked H5HA Mutant Antigens

Figure 23:
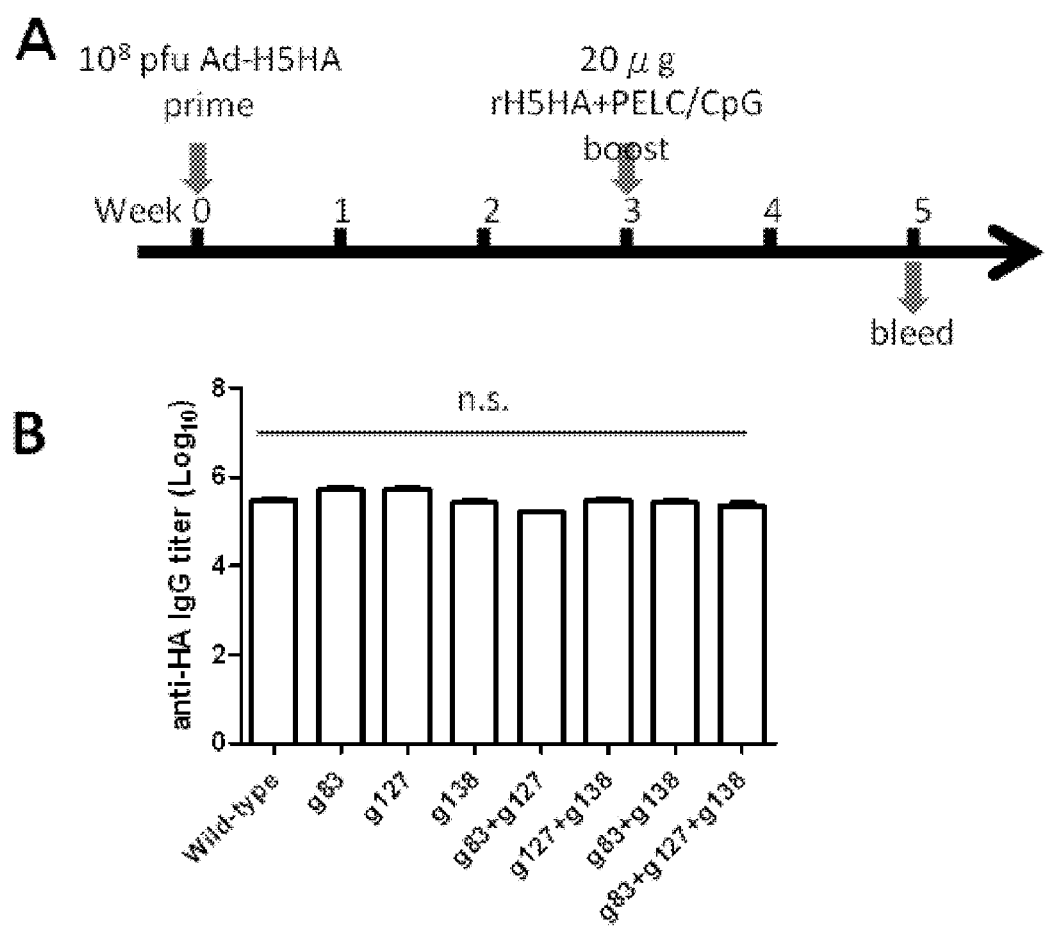
FIG. 23 shows that (A) Immunization regimen by adenovirus prime and recombinant protein booster (B) H5HA-specific IgG titers elicited by the individual glycan-masked H5HA immunizations were determined by ELISAs. Data represent geometric mean±standard deviation; one-way ANOVA and Tukey's test results indicate no significant (n.s.) differences.

It has been reported that a heterologous prime-booster immunization regimen using an adenovirus vector and recombinant HA protein elicits more potent neutralizing antibodies against homologous and heterologous H5N1 virus clades (Lin S C, Huang M H, Tsou P C, Huang L M, Chong P et al. (2011) Recombinant trimeric HA protein immunogenicity of H5N1 avian influenza viruses and their combined use with inactivated or adenovirus vaccines. PLoS One 6: e20052). To evaluate the heterologous neutralizing antibody responses elicited by glycan-masked mutant antigens groups of 6- to 8-week-old female BALB/c mice were primed with $10^8$ pfu of H5HA-encoding adenovirus vector followed by a booster of 20 μg recombinant H5HA proteins coupled with PELC/CpG 3 weeks later (FIG. 23A). According to analyses of serum samples collected two weeks following the booster doses, no significant differences were noted in the H5HA-specific IgG titers elicited by each type of glycan-masked H5HAs compared to those elicited by the wild-type immunizations (FIG. 23B).

HI and Neutralizing Antibody Titers Elicited by Glycan-masked H5HA Mutant Antigens.

Figure 24:
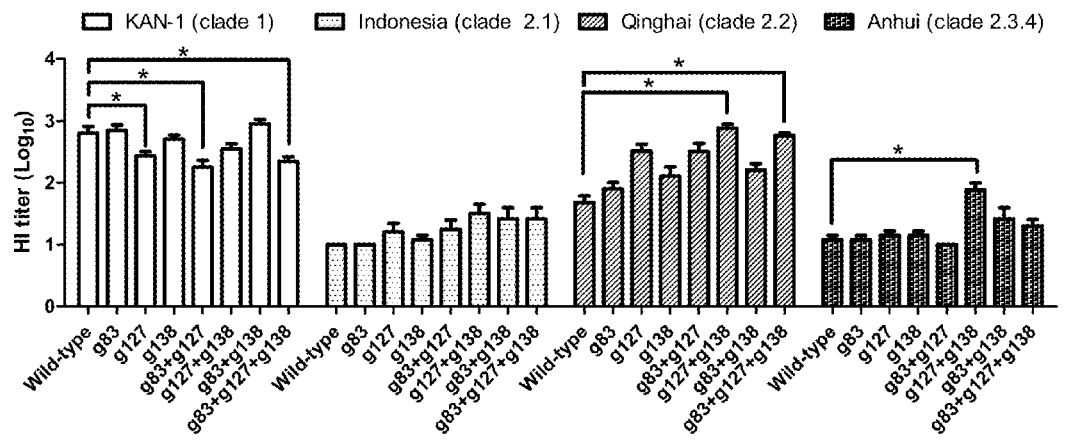

All of the glycan-masked mutants except for g127, g83+g127, and g83+g127+g138 retained similar levels of HI titers against homologous H5N1 (KAN-1, clade 1)-pseudotyped particles (H5 pp) (FIG. 24). For HI titers against three heterologous forms of H5 pp (Indonesia, clade 2.1; Qinghai, clade 2.2; Anhui, clade 2.3.4), all of the glycan-masked mutants except for g83 elicited slightly higher HI titers for the Indonesia clade 2.1 H5 pp. Titers elicited by the glycan-masked gp127+g138 and g83+g127+g138 mutants were significantly higher for the Qinghai clade 2.2 H5 pp, and titers for the glycan-masked g127+g138 mutant were significantly higher for the Anhui clade 2.3.4 H5 pp (FIG. 24).

Figure 25:
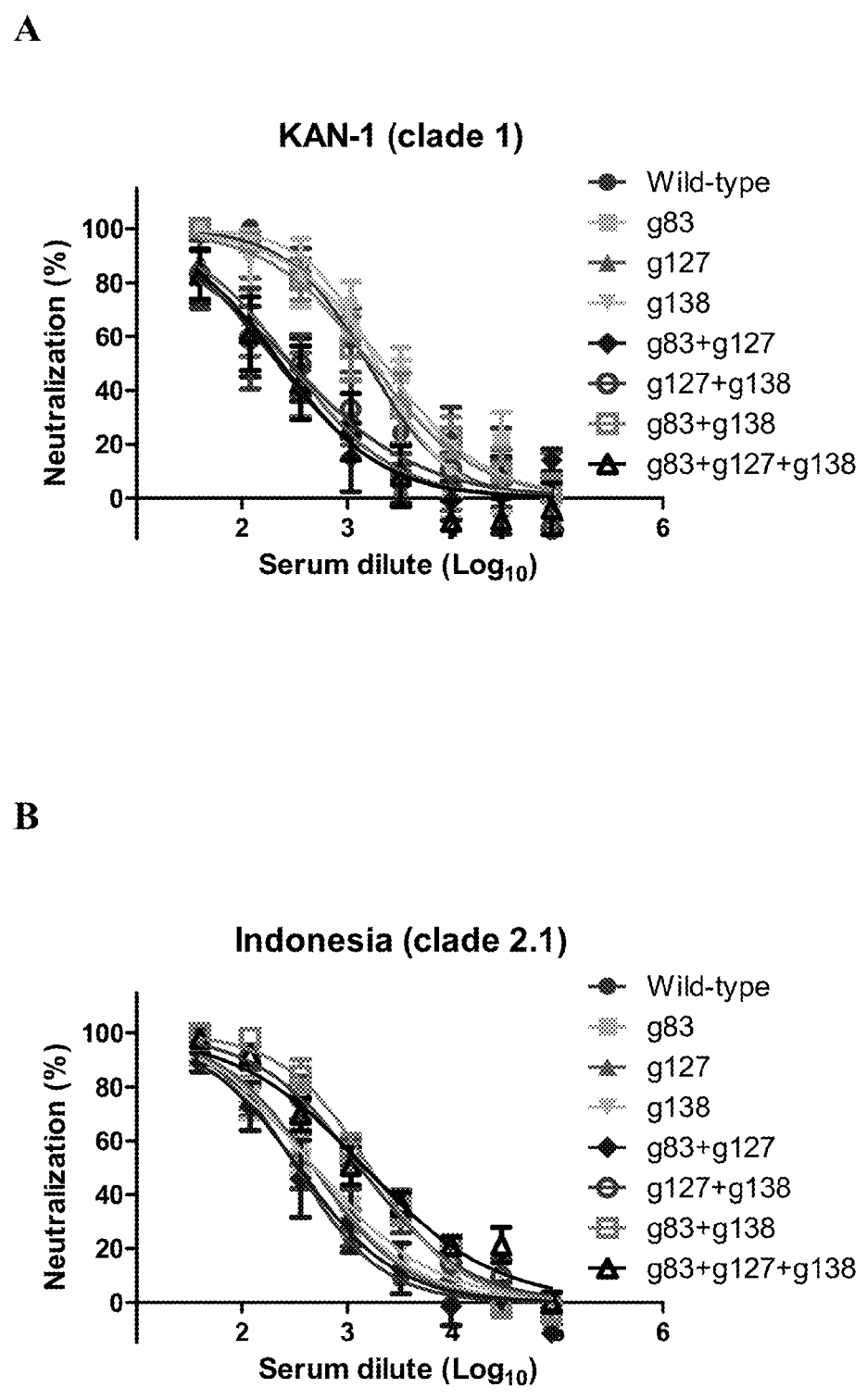
Figure 25:
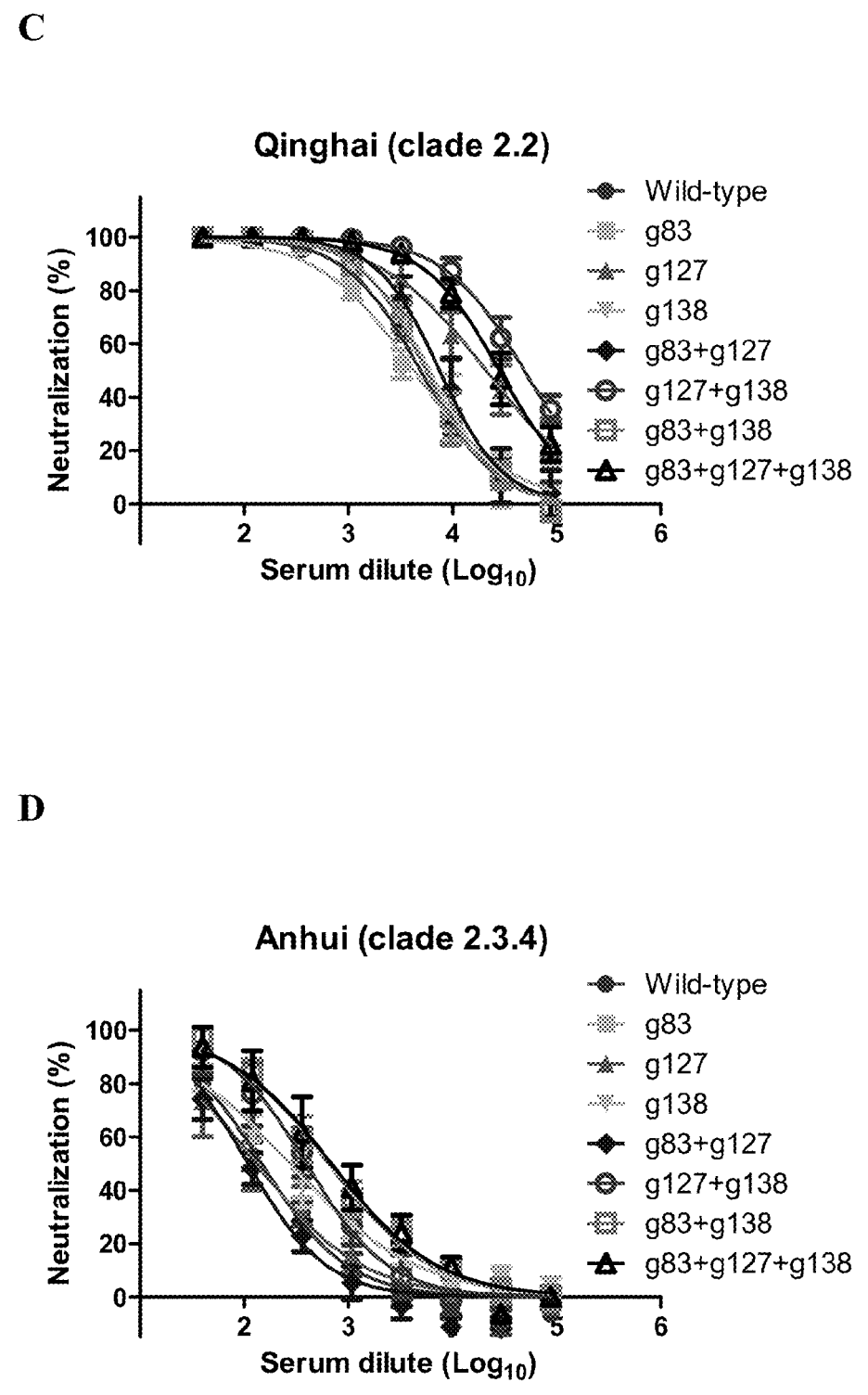
Figure 26:
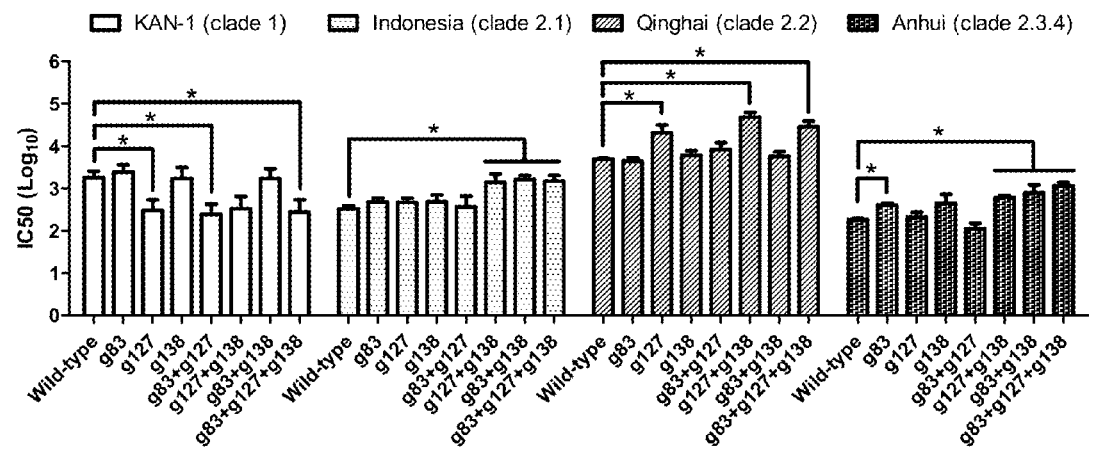

Neutralizing antibodies elicited by the immunizations of WT, single, double, and triple mutants of glycan-masked H5HA antigens against homologous and heterologous clades of H5N1 viruses were also measured. Serum-dilution neutralization curves for each immunization group were shown against H5 pp of KAN-1, clade 1 (FIG. 25A); Indonesia, clade 2.1 (FIG. 25B); Qinghai, clade 2.2 (FIG. 25C); and Anhui, clade 2.3.4 (FIG. 25D). Corresponding IC50 values were calculated from neutralization curves to give half maximal (50%) inhibition for the dilution of the sera. The results indicated that glycan-masked g127, g83+g127 and g83+g127+g138 mutants had reduced IC50 values for the homologous KAN-1, clade 1 strain of H5 pp (FIG. 26). In contrast, the glycan-masked g127+g138, g83+g138 and g83+g127+g138 mutants had increased IC50 values for the Indonesia clade 2.1 H5 pp (FIG. 26). The glycan-masked g127, g127+g138 and g83+g127+g138 mutants had increased IC50 values for the Qinghai clade 2.2 H5 pp (FIG. 26). The glycan-masked g83, g138, g127+g138, g83+g138 and g83+g127+g138 mutants had higher IC50 values for the Anhui clade 2.3.4 H5 pp (FIG. 26). All together, the data indicated that the glycan-masked g127+g138 mutant elicited significantly broader HI and neutralizing antibody responses against heterologous H5N1 virus strains. However, these sera did not elicit significant titers of HI and neutralizing antibodies against H1N1pdm09, H3N2 and H7N9 viruses (data not shown).

Mapping RBS-specific Antibodies Elicited by Glycan-masked H5HA Immunization

Figure 27:
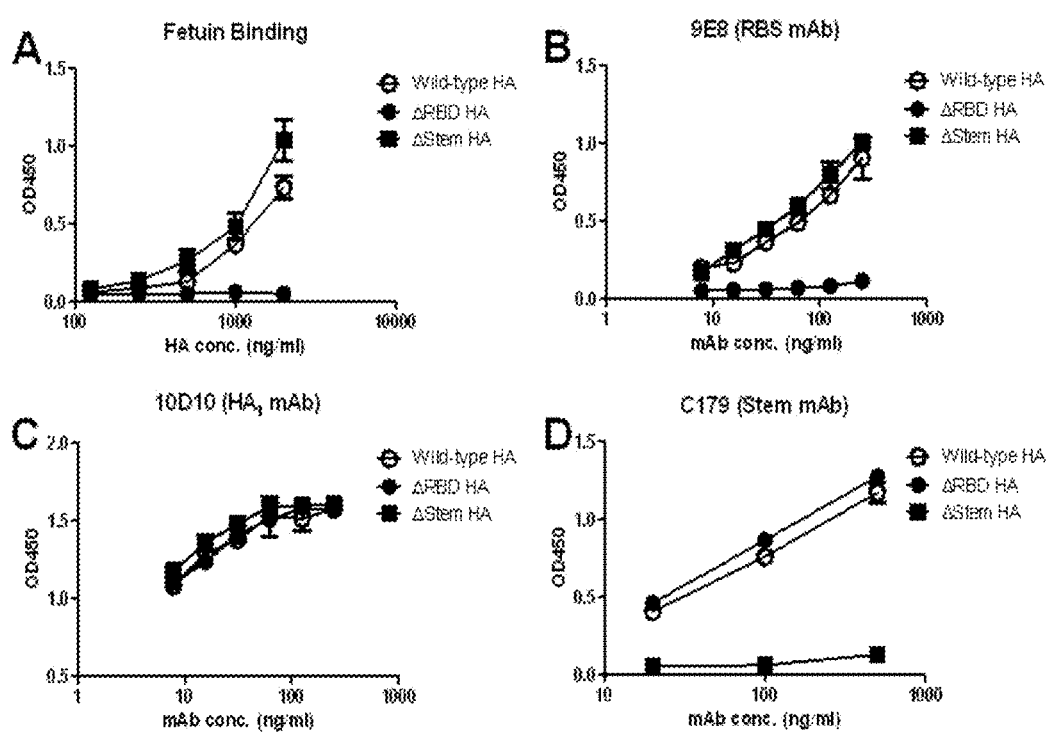
FIG. 27 shows identification of wild type-H5HA, ΔRBS-H5HA and ΔStem-H5HA proteins. (A) Serially diluted H5HA proteins (wild type, ΔRBS, ΔStem) were added to plates coated with fetuin and measured for ELISA binding. Different concentrations of (B) mAb 9E8 (targeted to the RBS 190 helix), (C) mAb 10D10 (targeted to the HA1 150 loop), and (D) mAb C179 (targeted to stem region) were reacted with each H5HA protein for ELISA binding.
Figure 28:
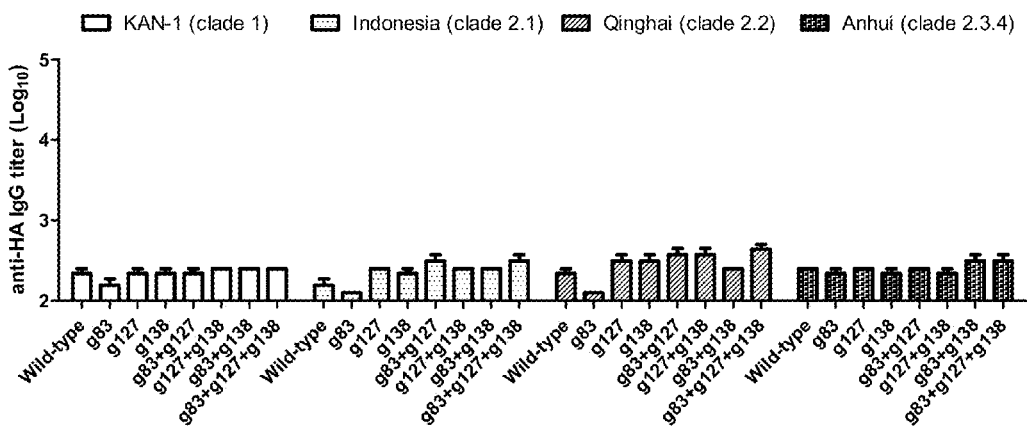
FIG. 28 shows mapping of RBS-specific antibodies elicited by glycan-masked H5HA mutants. Sera were pre-absorbed with (A) wild-type H5HA (KAN-1) protein or (B) ΔRBS-H5HA. ELISAs were performed to measure the HA-specific IgG titers of pre-absorbed sera against different HAs. (C) Pre-absorbed sera were also analyzed using fetuin-based serum inhibition assays to confirm RBS-specific antibody responses. Reduction titers (50%) of RBS-specific antibodies were measured as reduced fetuin binding to different HAs. Data represent geometric mean±standard deviation. Results were analyzed using one-way ANOVAs and Tukey's tests (*, statistical significance at $p<0.05$).
Figure 28:
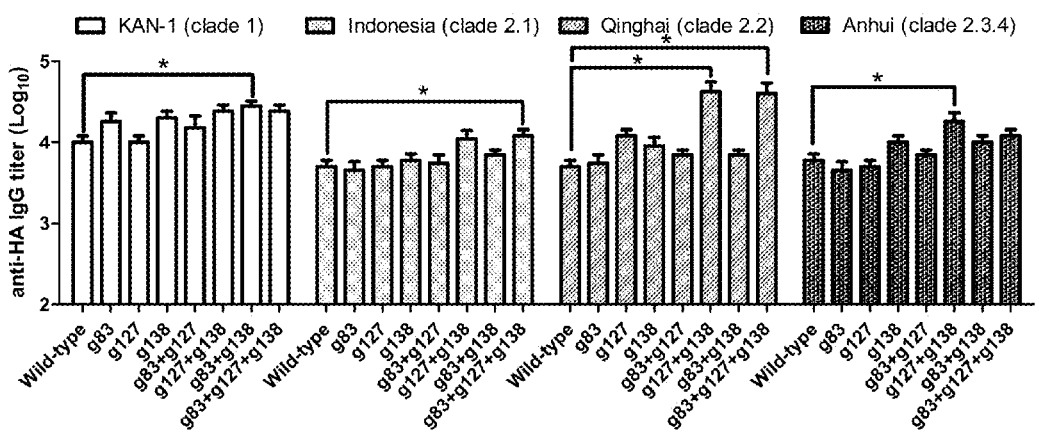

Since relatively conserved RBS represented a target for eliciting a broad spectrum of antibodies in contrast to other antigenic sites (Laursen N S, Wilson I A (2013) Broadly neutralizing antibodies against influenza viruses. Antiviral Res 98: 476-483), a H5HA mutant protein containing an additional N-glycan at residue 186 on the RBS 190 helix (ΔRBS-H5HA) (Kanekiyo M, Wei C J, Yassine H M, McTamney P M, Boyington J C et al. (2013) Self-assembling influenza nanoparticle vaccines elicit broadly neutralizing H1N1 antibodies. Nature. 499(7456): 102-6) was constructed to map RBS-specific antibody responses elicited by glycan-masked HA proteins. The E186N change in the RBS mutant (ΔRBS-H5HA) allowed for the introduction of an N-glycan into the RBS 190 helix, and I375N and a G377T changes in the stem mutant (ΔStem-H5HA) supported the introduction of an N-glycan into the mid-stem helix A. Mutant protein binding was confirmed using fetuin (FIG. 27A), mAb 9E8 (targeted to the RBS 190 helix) (FIG. 27B), mAb 10D10 (targeted to the HA1 150 loop) (Yang Z Y, Wei C J, Kong W P, Wu L, Xu L et al. (2007) Immunization by avian H5 influenza hemagglutinin mutants with altered receptor binding specificity. Science 317: 825-828) (FIG. 27C), and a stem-specific mAb C179 (Okuno Y, Isegawa Y, Sasao F, Ueda S (1993) A common neutralizing epitope conserved between the hemagglutinins of influenza A virus H1 and H2 strains. J Viol 67: 2552-2558) (FIG. 27D). Following antisera pre-absorption with the wild-type H5HA (KAN-1) protein, ELISA assays indicated relatively low levels of residual antibodies reacting with the wild-type H5HA proteins of the KAN-1, Indonesia, Qinghai, and Anhui strains (FIG. 28A), suggesting that the antibodies induced by these single, double, and triple glycan-masked HA immunizations primarily reacted with the wild-type H5HA protein. For the RBS-specific IgG titers against the KAN-1 strain (with ΔRBS-H5HA used to remove non receptor site-directed antibodies), all of the glycan-masked mutant-generated sera had similar or higher values for the KAN-1 strain compared with sera raised against wild-type KAN-1 HA. For RBS-specific IgG titers against the heterologous strains, the glycan-masked g127+g138 mutant was significantly higher for the Qinghai and Anhui strains, and the glycan-masked g83+g127+g138 mutant was significantly higher for the Indonesia and Anhui strain, all compared to the wild-type H5HA (FIG. 28B). Overall, the glycan-masked g127+g138 and g83+g127+g138 mutants were the more effective H5HA antigens in terms of inducing a broader range of RBS-specific IgG antibodies.

Fetuin-based serum inhibition assay was used to further confirm the RBS-specific antibody responses elicited by the glycan-masked H5HA immunizations. For the 50% reduction titers of RBS-specific antibodies, antisera was used to measure the reduction of fetuin binding to the recombinant H5HA proteins of the KAN-1, Indonesia, Qinghai, and Anhui strains. For reduction titers against the homologous strain, the glycan-masked g83+g127 mutant was significantly lower for the KAN-1 strain. For reduction titers against the heterologous strains, the glycan-masked g127+g138 and g83+g138 mutants were significantly higher for the Indonesia and Anhui strains, and the glycan-masked g127+g138 and g83+g127+g138 mutants were significantly higher for Qinghai strain compared to the wild-type H5HA (FIG. 28C). In other words, the glycan-masked g127+g138 mutant elicited the highest levels of RBS-specific antibodies inhibiting the receptor binding of the three heterologous H5N1 virus clades.

Mapping Stem-specific Antibodies Elicited by Glycan-masked HA Immunization

Figure 29:
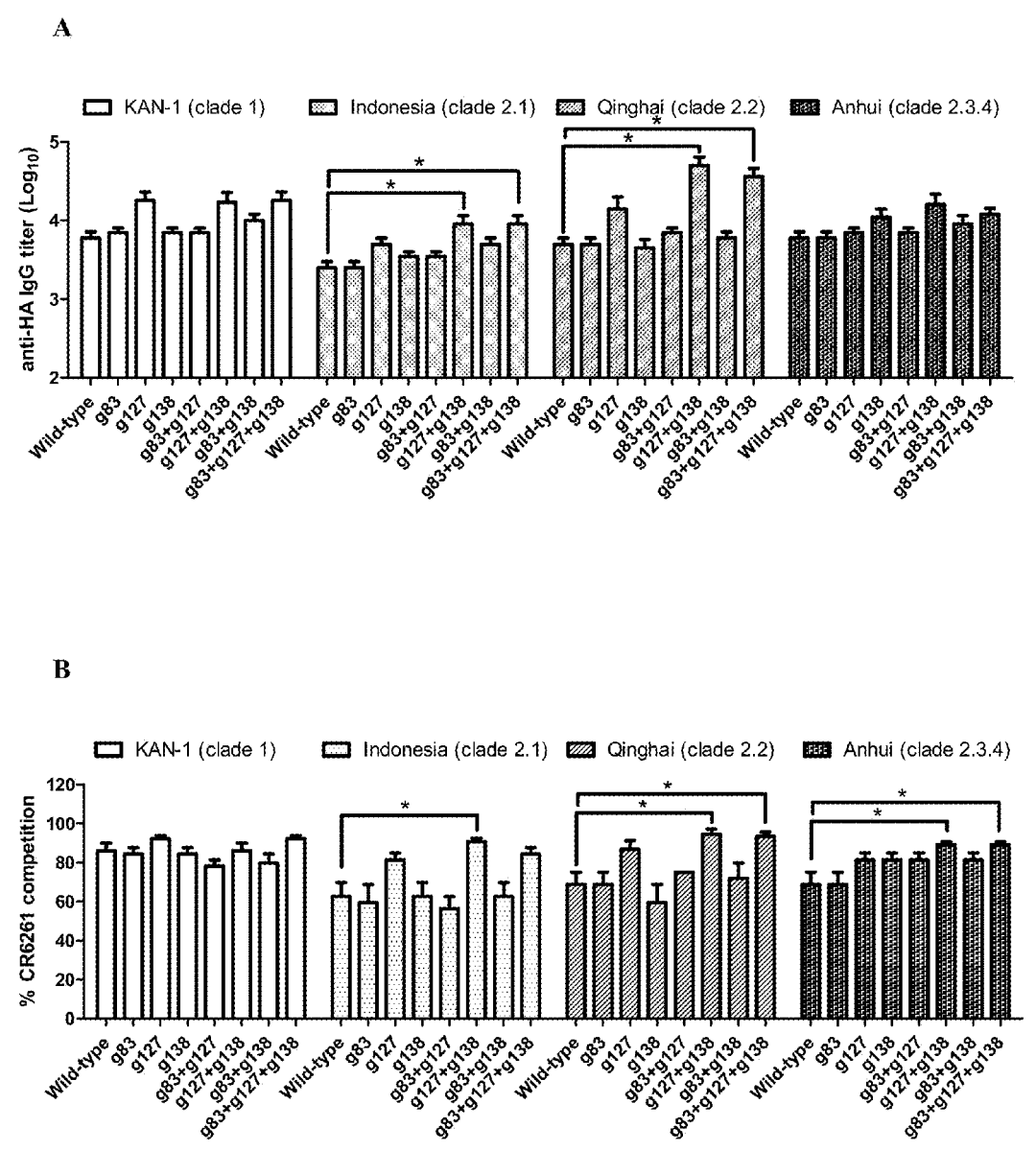
Figure 29:
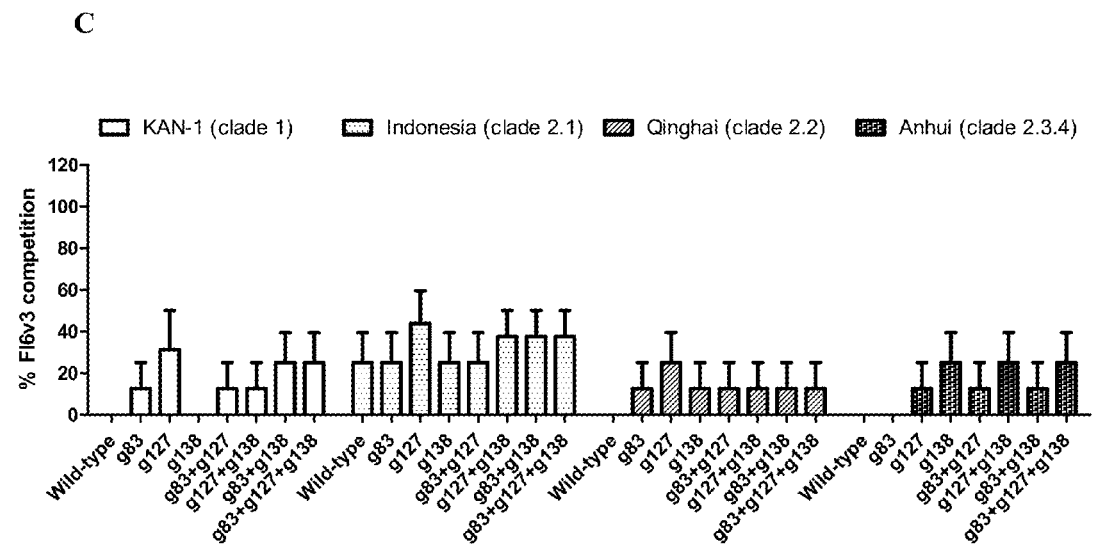

Since several stem-directed antibodies were found to neutralize viruses by binding to the highly conserved HA stem region that is essential for fusion (Laursen N S, Wilson I A (2013) Broadly neutralizing antibodies against influenza viruses. Antiviral Res 98: 476-483), a H5HA mutant protein containing an additional N-glycan at residue 375 in the conserved stem region (ΔStem-H5HA) (Wei C J, Boyington J C, McTamney P M, Kong W P, Pearce M B et al. (2010) Induction of broadly neutralizing H1N1 influenza antibodies by vaccination. Science 329: 1060-1064) was constructed to map stem-specific antibody responses elicited by glycan-masked HA proteins. Fetuin, mAb 9E8, mAb 10D10, and mAb C179 were used to confirm specific instances of binding. For stem-specific IgG titers against the homologous strain (using ΔStem-H5HA to remove non-specific antibodies), it was observed that the g127, g127+g138 and g83+g127+g138 mutants were higher for the KAN-1 strain. For stem-specific IgG titers against heterologous strains, the g127+g138 and g83+g127+g138 mutants were higher for the Indonesia and Qinghai strains, and the g127+g138 mutant was higher for the Anhui strain compared to the wild-type H5HA (FIG. 29A). According to these results, the g127+g138 mutant was the most effective H5HA protein for inducing a broad range of stem-specific antibodies.

To further investigate the bindings of different cross-reactive stem-specific antibodies, competition assays were performed using mAb CR6261 (capable of neutralizing the H1, H2, H5, H6, H8 and H9 subtypes) (Throsby M, van den Brink E, Jongeneelen M, Poon L L, Alard P et al. (2008) Heterosubtypic neutralizing monoclonal antibodies cross-protective against H5N1 and H1N1 recovered from human IgM+ memory B cells. PLoS One 3: e3942) and mAb FI6v3 (capable of neutralizing the H1, H3, H5 and H7 subtypes) (Corti D, Voss J, Gamblin S J, Codoni G, Macagno A et al. (2011) A neutralizing antibody selected from plasma cells that binds to group 1 and group 2 influenza A hemagglutinins Science 333: 850-856). The IgG titers of antisera pre-absorbed with ΔStem-H5HA were measured by ELISAs coated with different H5HA recombinant proteins blocked with mAbs, and percentages of blocked binding between pre-absorbed antisera and different H5HA proteins were calculated. Compared to the control antibody, mAb CR6261 significantly inhibited pre-absorbed antisera binding to the HA proteins of the KAN-1 (clade 1), Indonesia (clade 2.1), Qinghai (clade 2.2), and Anhui (clade 2.3.4) strains. For antibodies against the homologous strain, all glycan-masked mutants elicited similar levels of stem-specific antibodies competing with mAb CR6261 for the KAN-1 strain (FIG. 29B). For antibodies against the heterologous strains, the g127+g138 mutant elicited higher levels of stem-specific antibodies competing with mAb CR6261 for the Indonesia strain (clade 2.1), and the g127+g138 and g83+g127+g138 mutants elicited higher levels of stem-specific antibodies competing with mAb CR6261 for the Qinghai (clade 2.2) and Anhui (clade 2.3.4) strains compared to the wild-type H5HA. Unlike the mAb CR6261 competition, the stem-specific antibody titers elicited by all of the glycan-masked mutants (including g127+g138 and g83+g127+g138) were not outcompeted by mAb FI6v3 (FIG. 29C). The stem-specific antibodies elicited by the g127+g138 double mutant were CR6261-like, but not FI6v3-like.

Cross-clade Protection in Mice Following Live Virus Challenge

Figure 30:
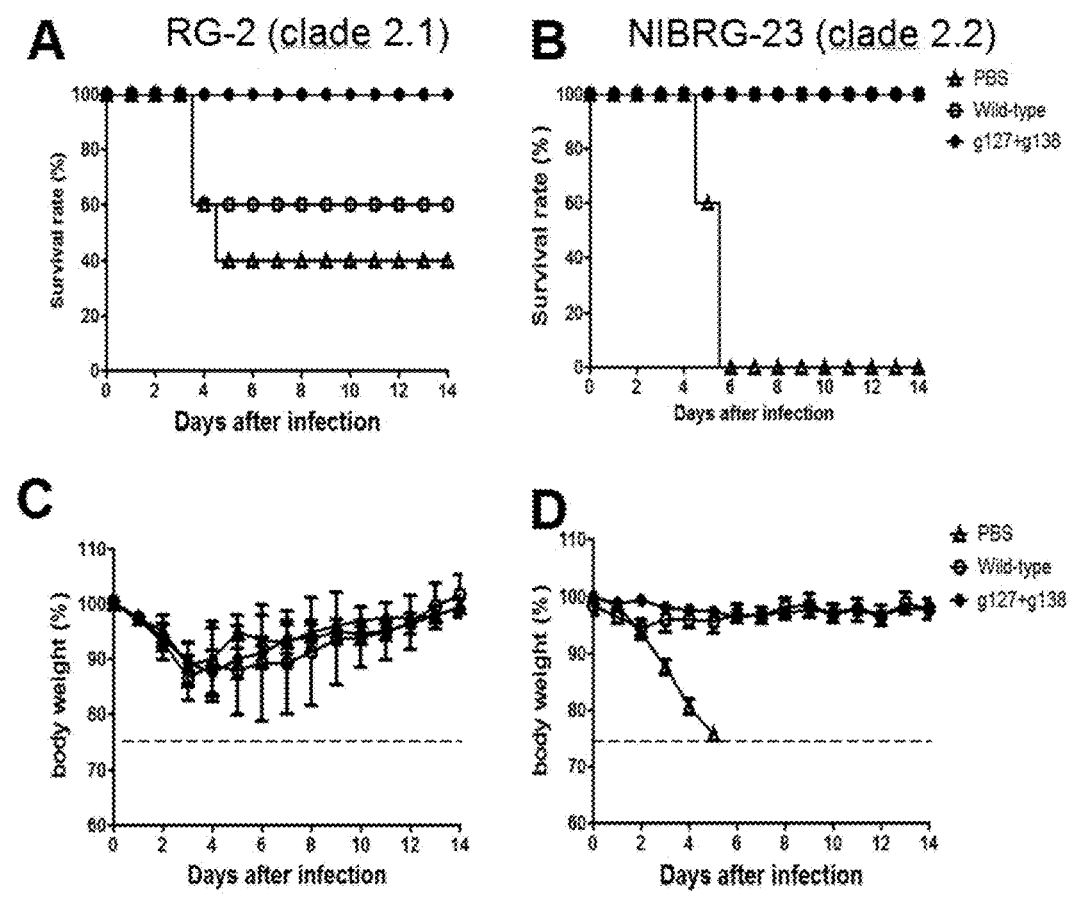

To investigate the cross-clade protection elicited by the glycan-masked g127+g138 mutant, immunized mice were challenged with heterologous clades of H5N1 live viruses (RG-2 and NIBRG-23) to assess the protective immunities. For RG2 (clade 2.1) virus challenge, a complete protection was observed for immunization with the glycan-masked g127+g138 mutant as compared to 60% survival for the wild-type H5HA and 40% for the PBS control immunizations (FIG. 30A). No significant differences in reduced body weight loss were found among these three groups (FIG. 30C). For NIBRG-23 virus (clade 2.2) challenge, the glycan-masked g127+g138 mutant and the wild-type H5HA immunizations all elicited 100% protection as compared to 0% for the PBS immunization (FIG. 30B). Again, no significant differences in reduced body weight loss were found between the wild type and the g127+g138 mutant immunizations as compared to 0% for the PBS immunization (FIG. 30D).

One skilled in the art readily appreciates that the present invention is well adapted to carry out the objects and obtain the ends and advantages mentioned, as well as those inherent therein. The vaccines, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A recombinant DNA molecule encoding a mutated influenza hemagglutinin protein, wherein the mutated influenza hemagglutinin protein consists of the amino acid sequence of SEQ ID NO: 2 comprising one or more mutations at amino acid residue selected from the group consisting of residue 83, 127, 138 of SEQ ID NO: 2 and the combination thereof.

2. The recombinant DNA molecule of claim 1, wherein the mutated influenza hemagglutinin protein consists of the amino acid sequence selected from the group consisting of SEQ ID NO: 4, 10, 33, 35, 37, 39 and 41.

3. The recombinant DNA molecule of claim 1, wherein the mutated influenza hemagglutinin protein consists of the amino acid sequence of SEQ ID NO: 37.

4. The recombinant DNA molecule of claim 1, wherein the mutated influenza hemagglutinin protein consists of the amino acid sequence of SEQ ID NO: 41.

5. A composition comprising the recombinant DNA molecule of claim 1 and a pharmaceutically or veterinarily acceptable carrier, excipient, adjuvant, or vehicle.

6. The composition of claim 5, wherein the composition elicits an immune response against a plurality of avian influenza virus subtypes in a subject.

7. A kit for prime-boost vaccination, comprising at least a composition comprising a recombinant DNA molecule of claim 1 and at least a composition for the boost-vaccination comprising a recombinant influenza hemagglutinin protein or an influenza virus-like particle, wherein the recombinant influenza hemagglutinin protein is encoded by the recombinant DNA molecule.

8. The kit of claim 7, wherein the recombinant influenza hemagglutinin protein consists of the amino acid sequence selected from the group consisting of SEQ ID NO: 4, 10, 33, 35, 37, 39 and 41.

9. A method of vaccinating a subject susceptible to avian influenza comprising administrating to the subject an effective amount of the composition of claim 5.

10. The method of claim 9, wherein the method further comprises a prime-boost administration regimen.

11. The method of claim 10, wherein the prime-boost administration regimen comprises a prime-administration of a composition of claim 5.

12. The method of claim 10, wherein the prime-boost administration regimen comprises a boost administration of a composition of claim 5.

13. The method of claim 10, wherein the prime-boost administration regimen comprises a prime-administration of a composition of claim 5 and a boost administration of a composition comprising a recombinant influenza hemagglutinin protein or an influenza virus-like particle, wherein the recombinant influenza hemagglutinin protein is encoded by the recombinant DNA molecule.

14. The method of claim 13, wherein the recombinant influenza hemagglutinin protein consists of the amino acid sequence selected from the group consisting of SEQ ID NO: 4, 10, 33, 35, 37, 39 and 41.

15. The method of claim 9, wherein the administering an effective amount of the composition of claim 5 results in an immune response against multiple avian influenza virus subtypes in the subject.

16. A recombinant influenza hemagglutinin protein consisting of the amino acid sequence of SEQ ID NO: 2 comprising one or more mutations at amino acid residue selected from the group consisting of residue 83, 127, 138 of SEQ ID NO: 2, and the combination thereof.

17. The recombinant influenza hemagglutinin protein of claim 16, wherein the protein consists of the amino acid sequence selected from the group consisting of SEQ ID NO: 4, 10, 33, 35, 37, 39 and 41.

18. The recombinant influenza hemagglutinin protein of claim 16, wherein the protein consists of the amino acid sequence of SEQ ID NO: 37.

19. The recombinant influenza hemagglutinin protein of claim 16, wherein the protein consists of the amino acid sequence of SEQ ID NO: 41.

* * * * *